United States Patent
Kirshenbaum et al.

(10) Patent No.: US 11,766,480 B2
(45) Date of Patent: Sep. 26, 2023

(54) MULTIVALENT PEPTOID OLIGOMERS, PHARMACEUTICAL COMPOSITIONS AND METHODS OF USING SAME

(71) Applicant: NEW YORK UNIVERSITY, New York, NY (US)

(72) Inventors: Kent Kirshenbaum, New York, NY (US); Paul Michael Levine, New York, NY (US); Michael John Garabedian, New York, NY (US); Justin M. Holub, Athens, OH (US)

(73) Assignee: NEW YORK UNIVERSITY, New York, NY (US)

( * ) Notice: Subject to any disclaimer, the term of this patent is extended or adjusted under 35 U.S.C. 154(b) by 172 days.

(21) Appl. No.: 15/938,418

(22) Filed: Mar. 28, 2018

(65) Prior Publication Data
US 2018/0311367 A1 Nov. 1, 2018

Related U.S. Application Data

(63) Continuation of application No. 14/394,996, filed as application No. PCT/US2013/036719 on Apr. 16, 2013, now abandoned.

(60) Provisional application No. 61/624,865, filed on Apr. 16, 2012.

(51) Int. Cl.
| | |
|---|---|
| A61K 47/54 | (2017.01) |
| C07K 5/083 | (2006.01) |
| C07K 5/103 | (2006.01) |
| C07K 7/06 | (2006.01) |
| C07K 7/64 | (2006.01) |
| A61K 47/64 | (2017.01) |
| A61K 47/55 | (2017.01) |
| C07K 7/08 | (2006.01) |
| C07K 14/00 | (2006.01) |
| A61K 47/59 | (2017.01) |
| A61K 38/00 | (2006.01) |

(52) U.S. Cl.
CPC ............ *A61K 47/554* (2017.08); *A61K 47/55* (2017.08); *A61K 47/59* (2017.08); *A61K 47/64* (2017.08); *C07K 5/0806* (2013.01); *C07K 5/1008* (2013.01); *C07K 7/06* (2013.01); *C07K 7/08* (2013.01); *C07K 7/64* (2013.01); *C07K 14/001* (2013.01); *A61K 38/00* (2013.01)

(58) Field of Classification Search
CPC ............ A61K 47/48246; A61K 47/481; A61K 47/48123; A61K 38/00; C07K 5/0806; C07K 5/1008; C07K 7/06; C07K 7/08; C07K 7/64; C07K 14/001

See application file for complete search history.

(56) References Cited

U.S. PATENT DOCUMENTS

| | | | | |
|---|---|---|---|---|
| 8,524,663 B2 * | 9/2013 | Kirshenbaum | ...... | A61K 47/641 514/9.7 |
| 2012/0122779 A1 * | 5/2012 | Kirshenbaum | ...... | A61K 47/641 514/9.7 |

FOREIGN PATENT DOCUMENTS

| | | | | |
|---|---|---|---|---|
| WO | 2009139922 | | 11/2009 | |
| WO | WO 2009/139922 | * | 11/2009 | ........... C07C 229/00 |
| WO | 2010098843 | | 9/2010 | |

OTHER PUBLICATIONS

Stover et al., Estrogen down-regulation of androgen receptors in cultured human mammary cancer cells (MCF-7) Endocrinology Jun. 1987:120(6):2597-603, Abstract only provided) (Year: 1987).*
Holub et al., Peptoids on Steroids: Precise Multivalent Estradiol-Peptidomimetic Conjugates Generated via Azide-Alkyne [3+2] Cycloaddition Reactions, QSAR Comb. Sci. 26, 2007, No. 11-12, 1175-1180 (Year: 2007).*
Handl et al., Hitting multiple targets with multimeric ligands, Expert Opin. Ther. Targets (2004) 8(6) 565-586 (Year: 2004).*
Bioconjugation to Functionalize Peptidomimetics: Peptoid-based Selective Estrogen Receptor Modulators, Justin M. Holub, Dissertation Sep. 2009, 244 pages (Year: 2009).*
Shabsigh et al., International Journal of Impotence Research (2009) 21, 9-23 (Year: 2009).*
Kampa et al., Steroids 73 (2008) 953-960 (Kampa), Papadopoulou et al., Molecular Cancer 2008, 7:88, 13 pages (Year: 2008).*

(Continued)

*Primary Examiner* — Fred H Reynolds
*Assistant Examiner* — Joseph Fischer
(74) *Attorney, Agent, or Firm* — Hoffmann & Baron, LLP

(57) ABSTRACT

Novel peptoid oligomers are disclosed that have a formula represented by the following formula Ia or Ib:

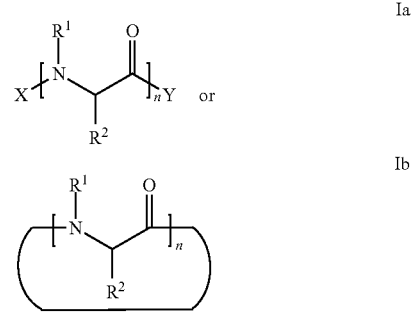

The peptoid oligomers are prepared as modulators of androgen receptor (AR), and may be prepared as pharmaceutical compositions and used for the prevention or treatment of a variety of conditions in mammals, including humans, associated with unwanted or aberrant AR activity. The present peptoid oligomers are particularly valuable for the treatment of subjects with cancer.

20 Claims, 12 Drawing Sheets

(56) References Cited

OTHER PUBLICATIONS

Papadopoulou et al., Molecular Cancer 2008, 7:88, 13 pages (Year: 2008).*
Bennett et al., Structure 1997 vol. 5 No. 6, pp. 799-812 (Year: 1997).*
Presolski et al, Curr. Protoc. Chem. Biol. 3:153-162, 2011 (Year: 2011).*
Adessi and Soto, Current Medicinal Chemistry, 2002, vol. 9, No. 9, 963-978 (Year: 2002).*
Miyamoto et al., "3β-Acetoxyandrost-1,5-diene-17-ethylene ketal functions as a potent antiandrogen With marginal agonist activity." Proc Natl. Acad. Sci., 2003, 100:4440-4444.
McGinley et al., "Circumventing anti-androgen resistance by molecular design", J. Am. Chem. Soc., 2007, 129:3822-3823.
Levine et al., "Androgen receptor antagonism by divalent ethisterone conjugates in castrate-resistant prostate cancer cells", ACS Chem Biol, 2012, 7:1693-1701.
Levine et al., "Multivalent peptidomimetic conjugates: a versatile platform for modulating androgen receptor activity", J Am Chem Soc, 2012, 134:6912-6915.
Wang et al., "Multivalent peptoid conjugates which overcome enzalutamide resistance in prostate cancer cells", Cancer Research, 2016, 76:5124-5132.
Holub, J.M., et al., "Peptoids on Steroids: Precise Multivalent Estradiol—Peptidomimetic Conjugates Generated via Azide-Alkyne [3+2] Cycloaddition Reactions", QSAR Combinatorial Science, 2007, vol. 26, No. 11-12, pp. 1175-1180.
Holub, J.M. et al., "Modulation of human estrogen receptor alpha activity by multivalent estradiol-peptidomimetic conjugates", Molecular BioSystems, 2011, vol. 7, No. 2, pp. 337-345.
Levine, P.M. et al., "Multivalent Peptidomimetic Conjugates: A Versatile Platform for Modulating Androgen Receptor Activity", Journal of the American Chemical Society, Apr. 17, 2012, vol. 134, pp. 6912-6915.
Bhasin, et al., "Testosterone Therapy in Men with Androgen Deficiency Syndromes: An Endocrine Society Clinical Practice Guideline," J Clin Endocrinol Metab 95: 2536-2559, 2010.
Centenera, et al., "The Contribution of Different Androgen Receptor Domains to Receptor Dimerization and Signaling," Molecular Endocrinology 22: 2373-2382, 2008. doi: 10.1210/me.2008-0017.
Gautier, et al., "affy—analysis of Affymetrix GeneChip data at the probe level," Bioinformatics, vol. 20 No. 3 2004, pp. 307-315. DOI: 10.1093/bioinformatics/btg405.
Gentleman, et al., "Bioconductor: open software development for computational biology and bioinformatics," Genome Biology 2004, 5:R80. http://genomebiology.com/2004/5/10/R80.
Gioeli, et al., "Androgen Receptor Phosphorylation Regulation and Identification of the Phosphorylation Sites," the Journal of Biological Chemistry, vol. 277, No. 32, Issue of August 9, pp. 29304-29314, 2002. DOI 10.1074/jbc.M204131200.
Jez, et al., "A New Nomenclature for the Aldo-Keto Reductase Superfamily," Biochem Pharmacol 54;6:639-647, 1997.
Simon, et al., "Peptoids: A modular approach to drug discovery," Proc. Natl. Acad. Sci. USA, vol. 89, pp. 9367-9371, Oct. 1992.
Yeh et al., From estrogen to androgen receptor: A new pathway for sex hormones in prostate, Proc. Natl. Acad. Sci. USA, vol. 95, pp. 5527-5532, May 1998.
Barber et al., GAPDH as a housekeeping gene: analysis of GAPDH mRNA expression in a panel of 72 human issues, Physiol Genomics 21: 389-395, 2005.
Bhasin et al., Testosterone Therapy in Men with Androgen Deficiency Syndromes: an Endocrine Society Clinical Practice Guideline, J Clin Endocrinol Metab, Jun. 2010, 95(6):2536-2559, doi: 10.1210/jc.2009-2354.
Bohl et al., Structural basis for antagonism and resistance of bicalutamide in prostate cancer, PNAS, Apr. 26, 2005, vol. 102, No. 17, 6201-6206.
Bundgard, H., Ed., Design of prodrugs, Elsevier, Amsterdam 1985, pp. 6-9.
Carboni et al., Aliphatic Amino Azides as Key Building Blocks for Efficient Polyamine Syntheses, J. Org. Chem. 1993, 58, 3736-3741.
Carlson et al., Selective Tumor Cell Targeting Using Low-Affinity, Multivalent Interactions, ACS Chemical Biology, vol. 2 No. 2, 119-127, 2007, Published online Feb. 9, 2007.
Centenera et al., The Contribution of Different Androgen Receptor Domains to Receptor Dimerization and Signaling, Molecular Endocrinology 22(11):2373-2382, 2008 doi: 10.1210/me.2008-0017.
Chang et al., Suppression of Δ5-androstenediol-induced androgen receptor transactivation by selective steroids in human prostate cancer cells, Proc. Natl. Acad. Sci., vol. 96, pp. 11173-11177, Sep. 1999.
Chen et al., Molecular determinants of resistance to antiandrogen therapy, Nature Medicine, vol. 10, No. 1, January 2004, Published online Dec. 21, 2003; doi:10.1038/nm972, pp. 33-39.
Childs-Disney et al., Using Modularly Assembled Ligands to Bind RNA Internal Loops Separated by Different Distances, ChemBioChem 2011,12, 2143-2146, DOI: 10.1002/cbic.201100298.
Culig et al., Switch from antagonist to agonist of the androgen receptor blocker bicalutamide is associated with prostate tumour progression in a new model system, British Journal of Cancer (1999) 81(2), 242-251.
Figliozzi et al., Synthesis of N-Substituted Glycine Peptoid Libraries, Methods in Enzymology, vol. 267 Copyright 1996 by Academic Press, Inc., pp. 437-447.
Fowler, Sarah A. and Blackwell, Helen E., Structure-function relationships in peptoids: Recent advances toward deciphering the structural requirements for biological function, Org Biomol Chem. Apr. 21, 2009; 7(8): 1508-1524. doi:10.1039/b817980h.
Gentleman et al., Bioconductor: open software development for computational biology and bioinformatics, Published: Sep. 15, 2004 Genome Biology 2004, 5:R80, R80.2-R80.16.
Gewirtz, David A., A Critical Evaluation of the Mechanisms of Action Proposed for the Antitumor Effects of the Anthracycline Antibiotics Adriamycin and Daunorubicin, Biochemical Pharmacology, vol. 57, pp. 727-741, 1999.
He et al., The FXXLF Motif Mediates Androgen Receptor-specific Interactions with Coregulators, The Journal of Biological Chemistry, vol. 277, No. 12, Issue of Mar. 22, p. 10226-10235, 2002.
Heinlein, Cynthia A. and Chawnshang Chang, Androgen Receptor in Prostate Cancer, Endocrine Reviews 25 (2):276-308 Copyright 2004 by The Endocrine Society doi: 10.1210/er.2002-0032.
Hjelmgaard et al., Convenient Solution-Phase Synthesis and Conformational Studies of Novel Linear and Cyclic α, β-Altemating Peptoids, Organic Letters 2009 Vol. 11, No. 18, 4100-4103.
Jones et al., AR Inhibitors Identified by High-Throughput Microscopy Detection of Conformational Change and Subcellular Localization, vol. 4 No. 3, ACS Chemical Biology 2009 199-208, 2009, Published online Feb. 23, 2009.
Kolb et al., Click Chemistry: Diverse Chemical Function from a Few Good Reactions, Angew. Chem. Int. Ed. 2001, 40, 2004-2021.
Kolev et al., Targeting Neural-Restrictive Silencer Factor Sensitizes Tumor Cells to Antibody-Based Cancer Immunotherapy In Vitro via Multiple Mechanisms, J Immunol 2010; 184:6035-6042; Prepublished online Apr. 26, 2010; doi: 10.4049/jimmunol.1000045 http://www.jimmunol.org/content/184/11/6035.
Lee, Younjoo and Sampson, Nicole S, Romping the cellular landscape: linear scaffolds for molecular recognition, Current Opinion in Structural Biology 2006, 16:544-550.
Lemus et al., 5α-Reduction of Norethisterone Enhances its Binding Affinity for Androgen Receptors but Diminishes its Androgenic Potency, J. Steroid Biochem. Molec. Biol. vol. 60, No. 1-2, pp. 121-129, 1997.
Levine, Paul M., Androgen Receptor Antagonism by Divalent Ethisterone Conjugates in Castrate-Resistant Prostate Cancer Cells, ACS Chem. Biol. 2012, 7,1693-1701.
McGinley, Paula L. and Koh, John T., Circumventing Anti-Androgen Resistance by Molecular Design, J. Am. Chem. Soc. 2007, 129, 3822-3823, Published on Web Mar. 10, 2007.
Miller et al., Comparison Of The Proteolytic Susceptibilities of Homologous L-Amino Acid, D-Amino Acid, and N-Substituted Glycine Peptide And Peptoid Oligomers, Drug Development Research 35:20-32 (1995).

(56) References Cited

OTHER PUBLICATIONS

Nickols, Nicholas G. and Dervan, Peter B., Suppression of androgen receptor-mediated gene expression by a sequence-specific DNA-binding polyamide, PNAS, Jun. 19, 2007, vol. 104, No. 25, 10418-10423.

Noren et al., A General Method for Site-Specific Incorporation of Unnatural Amino Acids into Proteins, Science, vol. 244, Apr. 14, 1989 DOI: 10.1126/science.2649980, 182-188.

Osguthorpe, D. J. and Hagler, A.T., Mechanism of Androgen Receptor Antagonism by Bicalutamide in the Treatment of Prostate Cancer, dx.doi.org/10.1021/bi102059z, Biochemistry 2011, 50, 4105-4113.

Ozers et al., The Androgen Receptor T877A Mutant Recruits LXXLL and FXXLF Peptides Differently than Wild-Type Androgen Receptor in a Time-Resolved Fluorescence Resonance Energy Transfer Assay, Biochemistry 2007, 46, 683-695, Published on Web Dec. 22, 2006.

Puffer et al., Activating B Cell Signaling With Defined Multivalent Ligands, ACS Chemical Biology, vol. 2 No. 4, 252-262, 2007, Published online Apr. 13, 2007.

Reczek et al., Multivalent Recognition of Peptides by Modular Self-Assembled Receptors, J. Am. Chem. Soc. 2009, 131, 2408-2415, Published on Web Jan. 27, 2009.

Schwefel et al., Structural Basis Of Multivalent Binding to Wheat Germ Agglutinin, J. Am. Chem. Soc. 2010, 132, 8704-8719, Published on Web Jun. 7, 2010.

Shaffer et al., Structural basis of androgen receptor binding to selective androgen response elements, 4758-4763 PNAS Apr. 6, 2004 vol. 101 No. 14 www.pnas.org/cgi/doi/10.1073/pnas.0401123101.

Shin et al., Cyclic Peptides J. Am. Chem. Soc. 2007, 129, 3218-3225, Published on Web Feb. 27, 2007.

Singh et al., Rational Design of Novel Antiandrogens for Neutralizing Androgen Receptor Function in Hormone Refractory Prostate Cancer, The Prostate 68:1570-1581 (2008).

Tan et al., High-throughput evaluation of relative cell permeability between peptoids and peptides, Bioorganic & Medicinal Chemistry 16 (2008) 5853-5861.

Tannock, et al., Docetaxel plus Prednisone or Mitoxantrone plus Prednisone for Advanced Prostate Cancer, N Engl J Med 2004;351:1502-12, www.nejm.org Oct. 7, 2004.

Tran et al., Development of a Second-Generation Antiandrogen for Treatment of Advanced Prostate Cancer, Science. May 8, 2009; 324(5928): 787-790. doi: 10.1126/science.1168175.

Waller et al., Androgen receptor localisation and turnover in human prostate epithelium treated with the antiandrogen, Casodex, Journal of Molecular Endocrinology (2000) 24, 339-351.

Wang et al., Androgen Receptor Regulates a Distinct Transcription Program in Androgen-Independent Prostate Cancer, Cell. Jul. 23, 2009; 138(2): 245-256. doi:10.1016/j.cell.2009.04.056.

Wang, Ying and Kiick, Kristi L., Monodisperse Protein-Based Glycopolymers via a Combined Biosynthetic and Chemical Approach, J. Am. Chem. Soc. 2005, 127, 16392-16393, Published on Web Nov. 5, 2005.

Xu, Xiao-Ning and Screaton, Gavin R., MHC/peptide tetramer-based studies of T cell function, Journal of Immunological Methods 268 (2002) 21-28.

Yoo et al., Peptoid Macrocycles: Making the Rounds with Peptidomimetic Oligomers, Chem. Eur. J. 2010, 16, 5528-5537, DOI: 10.1002/chem.200903549.

Yu et al., A high-throughput assay for assessing the cell permeability of combinatorial libraries, Nature Biotechnology, vol. 23 No. Jun. 6, 2005, 746-751, Published online May 22, 2005; doi:10.1038/hbt1099.

Zhang et al., Characterization of cis Elements of the Probasin Promoter Necessary for Prostate-Specific Gene Expression, The Prostate 70:934-951 (2010), Published online Mar. 5, 2010 in Wiley InterScience (www.interscience.wiley.com).

Zuckermann et al., Efficient Method for the Preparation of Peptoids [Oligo(N-substituted glycines)] by Submonomer Solid-Phase Synthesis, J. Am. Chem. Soc. 1992, 114, 10646-10647.

* cited by examiner

MULTIVALENT PEPTOID OLIGOMERS, PHARMACEUTICAL COMPOSITIONS AND METHODS OF USING SAME

CROSS REFERENCE TO RELATED APPLICATIONS

The present application is a Continuation of co-pending non-provisional application Ser. No. 14/394,996, filed Oct. 16, 2014, which in turn, is a National Stage Application claiming the priority of PCT Application No. PCT/US2013/036719 filed Apr. 16, 2013, which in turn, claims priority from U.S. Provisional Application Ser. No. 61/624,865, filed Apr. 16, 2012. Applicant claims the benefits of 35 U.S.C. § 120 as to the non-provisional U.S. application and the PCT application, and priority under 35 U.S.C. § 119 as to the said U.S. Provisional application, and the entire disclosures of all of the said applications are incorporated herein by reference in their entireties.

GOVERNMENTAL SUPPORT

This invention was made with government support under Grant No. 0645361 awarded by National Science Foundation. The government has certain rights in the invention.

FIELD OF THE INVENTION

This invention relates to novel compositions containing peptoids or synthetic oligomers (peptidomimetic oligomers or conjugates), and particularly, to the use of such peptidomimetic oligomers as androgen receptor modulators. This invention generally relates to methods for using the synthetic oligomers to prevent, treat or ameliorate medical conditions associated with androgen receptor activity. The invention further relates to the use of synthetic oligomers and compositions thereof in pharmaceutical, healthcare, and medical device applications.

BACKGROUND OF THE INVENTION

Androgens are steroid hormones that can interact with the androgen receptor (AR) to play an important role in human endocrinology and disease [1]. AR is a ligand-dependent transcription factor capable of binding the native androgen dihydrotestosterone (DHT) [2]. The classical mechanism of AR activation involves DHT displacing a chaperone protein, thus inducing a conformational change that promotes receptor dimerization [3]. Upon phosphorylation and translocation into the nucleus, AR binds to specific DNA sequences and recruits necessary transcriptional co-factors to regulate gene expression [4, 5].

Androgens functioning through the AR can also promote prostate cancer development, growth and progression [6]. The advancement of prostate cancer from an androgen-dependent disease state to one that is androgen-independent represents the disease's lethal transformation, as limited therapeutic options exist for patients with advanced disease [7]. The standard approach for treating androgen-dependent prostate cancer is androgen ablation by suppression of testosterone production. This treatment option is typically accompanied by competitive DHT antagonists, such as bicalutamide, to block AR signaling [8]. While initially effective at suppressing tumor growth, these therapies often evoke castrate-resistant (or androgen-independent) prostate cancer progression [9].

AR is expressed in both androgen-dependent and androgen-independent prostate cancer cells [10]. Two cell model systems, LNCaP (androgen-dependent) and LNCaP-abl (androgen-independent) have been established to study AR function in these different disease states. AR-based drug discovery typically focuses on the development of chemical entities that can associate with the ligand-binding domain (LBD) of the AR. Drug resistance can therefore arise through mutations within the AR-LBD. Recent evidence suggests that allosteric binding sites on AR can also regulate receptor activity through non-competitive mechanisms, providing additional targets for pharmacology [10a]. Thus, the development of noncompetitive modulators that act independently or synergistically with competitive antagonists could shift the paradigm for prostate cancer therapy.

Multivalent scaffolds may be used to design competitive or non-competitive AR modulators with potential therapeutic significance. Multivalency has been shown to be advantageous in numerous applications due to its ability to enhance the effective local concentration of low affinity ligands, compensating for weak binding to target receptors [11,12]. Additionally, multivalent displays precisely exhibiting diverse recognition components are significant in the field of bioorganic and medicinal chemistry and could potentially find wide application [13,14]. Relative to monovalent binding interactions, multivalent displays possess distinct properties that distinguish them from their monovalent counterparts [15]. Multiple ligands conjugated to a single scaffold are capable of increasing intermolecular interactions and strengthen binding avidity [16]. The multi-site binding produced by these constructs provides stability in instances such as transient unbinding occurring at single sites [17]. In addition to stronger binding interactions, it is possible to manipulate the chemical characteristics of these sequence-specific oligomers to provide precise control of ligand spacing [18]. The ability to tune the characteristics at the other positions also makes them extremely suitable candidates for enhanced cell permeability [19,20].

Peptoids can be used as scaffolds to prepare these multivalent displays. Peptoids are a novel class of peptidomimetics in which the sidechains of peptides are shifted to the adjacent amide nitrogen atoms [21,22]. They are readily synthesized on solid support and can yield monodisperse products, unlike random copolymers or dendrimers. They also have the ability to site-specifically incorporate diverse sidechain functionality along the oligomer backbone for precise ligand conjugation [21b,23]. Additionally, peptoids have been considered advantageous for therapeutic applications due to their proteolytic resistance [24].

Despite the existing wealth of evidence pointing toward the biological effects of AR modulators, there remain limited therapeutic options to effectively target the medical conditions associated with advanced prostate cancer.

Thus, there is an on-going need for development of effective therapeutic agents that target the androgen receptor.

SUMMARY OF THE INVENTION

In one aspect, the present invention introduces a versatile multivalent scaffold to design competitive or non-competitive androgen receptor (AR) modulators with potential therapeutic significance (FIG. 1).

In another aspect, the present invention provides methods for preventing, treating or ameliorating medical conditions associated with aberrant AR activity.

In yet another aspect, the present invention provides modulators of AR activity.

In yet another aspect, the present invention provides novel synthetic oligomers or conjugates.

In a particular aspect, the present invention provides methods for preventing, treating or ameliorating medical conditions in mammals, which comprises administering to the mammal an effective amount of a synthetic oligomer according to formula Ia or Ib:

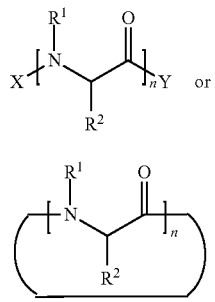

a pharmaceutically acceptable salt thereof; and stereoisomers, isotopic variants and tautomers thereof;

wherein each $R^1$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; substituted or unsubstituted cycloalkylalkyl, substituted or unsubstituted heterocycloalkylalkyl, substituted or unsubstituted aralkyl, or substituted or unsubstituted heteroarylalkyl;

each $R^2$ is independently hydrogen, or substituted or unsubstituted alkyl;

n is an integer between 2-45, when the synthetic oligomer is of formula Ia; and n is an integer between 4-45, when the synthetic oligomer is of formula Ib; and X is H, or substituted or unsubstituted acyl; Y is $NH_2$, OH, acylamino, or acyloxy;

provided that at least one monomer or up to 40 monomers comprises a androgen receptor modulator moiety.

In one embodiment, the medical condition is associated with altered hormone receptor activity. In a particular embodiment, the condition is associated with aberrant AR activity and includes, for example, age-related diseases including, but not limited to sarcopenia, conditions of cachexia and muscle loss induced by diseases including, but not limited to, cancer and AIDS, chronic obstructive pulmonary disease, chronic renal failure, thermal burns, bone and joint diseases, such as osteoporosis, reduction in libido and sexual dysfunction or anemia. In a particular embodiment, the medical condition is cancer. In one particular embodiment, the medical condition is prostate cancer or hyperplasia. In another particular embodiment, the medical condition is colon cancer.

In a further alternative embodiment, the present invention provides antagonists of AR that are thereby effective to treat or alleviate maladies or symptoms of unwanted AR activity, such as AR dependent prostate cancer, male contraception and benign hyperplasia of the prostate, ovarian and breast cancer. In one aspect an oligomer of the invention is an antagonist or partial antagonist and is of use in the prevention and/or treatment of AR dependent tumors and all the conditions in which AR stimulation could be detrimental such as acne, alopecia and hirsutism.

In one particular embodiment, the synthetic oligomer is according to formula Ia or Ib:

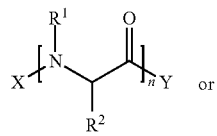

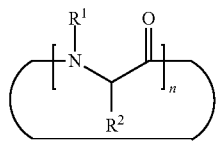

or a pharmaceutically acceptable salt thereof; and stereoisomers, isotopic variants and tautomers thereof;

wherein each $R^1$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; substituted or unsubstituted cycloalkylalkyl, substituted or unsubstituted heterocycloalkylalkyl, substituted or unsubstituted aralkyl, or substituted or unsubstituted heteroarylalkyl;

each $R^2$ is independently hydrogen, or substituted or unsubstituted alkyl;

n is an integer between 2-45, when the synthetic oligomer is of formula Ia; and n is an integer between 4-45, when the synthetic oligomer is of formula Ib; and X is H, or substituted or unsubstituted acyl; Y is $NH_2$, OH, acylamino, or acyloxy; provided that:

i) at least one monomer or up to 40 monomers are according to formula II:

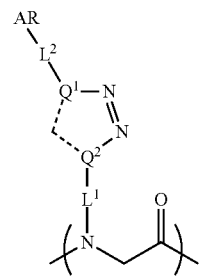

wherein
$L^1$ is $C_1$-$C_{10}$ alkylene;
$L^2$ is a single bond or $C_1$-$C_{10}$ alkylene;
$Q^1$ is N, and $Q^2$ is C; or $Q^1$ is C, and $Q^2$ is N;
one of the dotted bonds is a single bond and the other is a double bond;
AR is

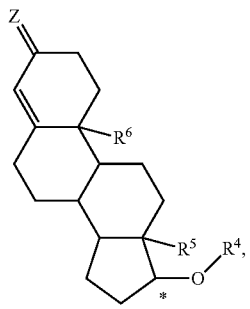

-continued

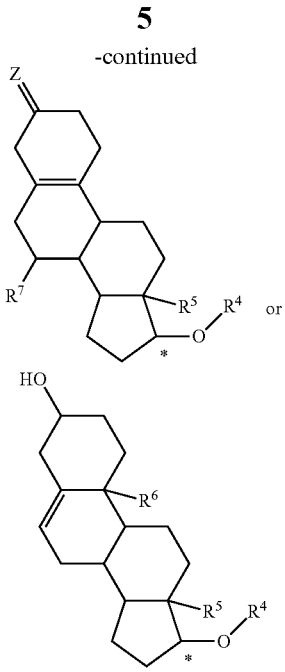

Z is O or N—O—R$^{3a}$; R$^{3a}$ is H or substituted or unsubstituted alkyl;
R$^4$ is H or acyl; R$^5$ is substituted or unsubstituted alkyl; each R$^6$ and R$^7$ is independently H or substituted or unsubstituted alkyl; and * denotes the attachment point;
and the rest of the monomers are according to formula VIa, VIb, or VIc:

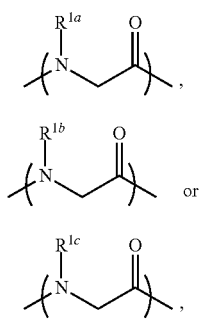

wherein
each R$^{1a}$ is independently unsubstituted alkyl, substituted alkyl, or cycloalkylalkyl;
each R$^{1b}$ is independently aminoalkyl, guanidinoalkyl (H$_2$N—C(=NH)—NH-alkyl), or N-containing heteroarylalkyl;
each R$^{1c}$ is independently substituted or unsubstituted aryl, substituted or unsubstituted aralkyl, substituted or unsubstituted heteroarylalkyl, or substituted or unsubstituted diarylalkyl.

The synthetic oligomers of the present invention are peptoid compounds wherein each monomer is attached to another monomer via a peptoid linkage. For example, the carbon of the carbonyl from the first monomer is attached to N of the second monomer via a single bond.

In a further aspect, the peptoid or synthetic oligomers of the invention may be used to treat AR related conditions. The peptoid or synthetic oligomers could be designed and assembled to include ligands pertinent for the treatment of AR related conditions, and then formulated into appropriate compositions and dosage forms for administration or application to an affected host. Moreover, such compositions may comprise a plurality of different peptoid or synthetic oligomers of the invention. Such compositions may further comprise mixtures or combinations of other therapeutic agents useful for the treatment of AR related conditions. In such formulations, the peptoid or synthetic oligomers of the invention may act synergistically with each other or other therapeutic agents, so that the resulting composition demonstrates improved effectiveness.

In a further aspect, the present invention provides pharmaceutical compositions comprising a peptoid of the invention, and a pharmaceutical carrier, excipient or diluent. In this aspect of the invention, the pharmaceutical composition can comprise one or more variant peptoid or synthetic oligomers of the invention, prepared, for example, with a differing array of peptoid linkers, to afford a more comprehensive treatment for a subject with AR related conditions. Likewise, and as stated above, the pharmaceutical compositions may comprise one or more of the peptoid or synthetic oligomers of the invention, in combination with other therapeutic agents.

In a further aspect of the invention, a method is disclosed for treating mammals, including humans, as well as lower mammalian species, susceptible to or afflicted with a condition attributable to or resulting from AR related conditions, which method comprises administering an effective amount of a pharmaceutical composition containing or comprising the peptoid or synthetic oligomers just described. In addition to the methods of treatment set forth above, the present invention extends to the use of any of the compounds of the invention for the preparation of medicaments or as medicaments that may be administered for such treatments, as well as to such compounds for the treatments disclosed and specified.

The present invention also encompasses therapeutic compositions for the treatment of AR related conditions comprising any of the compounds of the invention, a substrate comprising any of the compounds of the invention, wherein such a compound or compounds are bound to or incorporated into the substrate, and a device comprising such a substrate. Such articles include, without limitation, a medical device for transient or long term delivery of a compound or compounds of the invention.

Also encompassed herein are methods for making substrates or devices comprising any of the compounds of the invention. The present invention further extends to the use of any of the compounds of the invention for the generation of substrates or devices.

In additional aspects, this invention provides methods for synthesizing the complexes of the invention, with representative synthetic protocols and pathways disclosed later on herein.

Other objects and advantages will become apparent to those skilled in the art from a consideration of the ensuing detailed description, which proceeds with reference to the following illustrative drawings.

BRIEF DESCRIPTION OF THE DRAWINGS

FIG. 1 shows peptoid scaffolds permit design of oligomers to modulate Androgen Receptor activity through multivalent interactions. Colored circles represent sites amenable to chemical modification and ligand display. Homology model of the AR ligand binding domain dimer (green ribbon; PDB 1137) bound to native ligand (DHT-magenta).

FIG. 2 shows (A) Multivalent peptoid conjugates can compete with labeled hormone ligand and bind to AR (Veh., fluorescence polarization in absence of any competitor; DHT, 1 µM; Conjugates 1-3 and 5-7, 10 µM; Conjugate 4, 100 nM). (B) Transcriptional activation of AR in the presence of multivalent peptoid conjugates. Luciferase reporter assay performed in LB1 cells (Veh., EtOH treated cells; DHT, 10 nM; Conjugates 1-7, 1 µM). All data presented as mean+SD of triplicates.

FIG. 3 shows Effect of multivalent peptoid conjugates on cell proliferation in LNCaP-abl (A and B) and HEK293 (C) cells (Veh., EtOH treated cells; Bicalutamide (Bic.), 1 µM; Conjugates 6-8, 1 µM; Positive cytotoxic control Doxorubicin (Doxo.), 1 µM[33]. All data presented as mean+SD of triplicates. *Similar results observed for conjugate 7.

FIG. 4 shows multivalent peptoid conjugates can compete with labeled hormone ligand and bind to AR (Veh. (EtOH), fluorescence polarization in absence of any competitor; DHT, 1 µM; Conjugates 1-3 and 5-7, 100 nM; Conjugate 4, 10 nM). Data presented as mean+SD of triplicates.

FIG. 5 shows effect of multivalent peptoid conjugates on cell proliferation in LNCaP-abl cells (Veh., EtOH treated cells; Conjugates 1-3 and 5-7, 20 µM; Conjugate 4, 5 µM). Data presented as mean+SD of triplicates.

FIG. 6 shows effect of multivalent peptoid conjugates on cell proliferation in LNCaP-abl cells (Veh., EtOH treated cells; Bicalutamide (Bic.), 1 µM; Conjugates 6-8, 10 nM). Data presented as mean+SD of triplicates.

FIG. 7 shows Oligomers 6 and 7 differentially effect AR cellular localization. (A) Peptoid conjugates do not induce AR degradation. AR protein expression in treated LNCaP-abl cells with tubulin as a loading control (Veh., EtOH-treated cells; DHT, 10 nM; oligomer 6 or 7, 1 µM). Treatment times (h) are shown above the respective lanes. (B) Cellular localization of AR in treated HEK293 cells transfected with an AR fluorescent protein hybrid (Veh., EtOH-treated cells; DHT, 1 nM; oligomer 6 or 7, 1 µM). The yellow fluorescent protein (YFP) and 4,6-diamidino-2-phenylindole (DAPI) channels represent the localization of the AR fusion protein and the cell nuclei, respectively. In this figure, 1 is Oligomer 6 and 2 is Oligomer 7.

FIG. 8 shows Oligomers 6 and 7 disrupt co-activator peptide recruitment and DNA binding. Oligomer 7 also induces cell cycle arrest. (A) In vitro time resolved fluorescence resonance energy transfer (TR-FRET) analysis of the interaction between purified GST-tagged AR-LBD, terbium-labeled Arspecific anti-GST antibody, and fluorescein-labeled AR FxxLF co-activator peptide (increasing concentrations of DHT, Bicalutamide (Bic.), and Oligomer 6 or 7 were evaluated). The TR-FRET signal intensity between terbium-labeled antibody and labeled FxxLF-motif peptide is established by co-activator recruitment to the AR-LBD (520:495 nm emission ratio after excitation at 340 nm). Data presented as mean±SD of triplicates. (B) Chromatin immunoprecipitation analysis of AR in treated LNCaP-abl cells. Real-time PCR quantification of immunoprecipitated PSA enhancer is shown (R-1881, 10 nM; Oligomer 6 or 7, 1 µM). Data presented as mean+SD of triplicates. (C) Fluorescence-activated cell sorting analysis of treated LNCaP-abl cells (Veh., EtOH-treated cells; oligomer 6 or 7, 1 µM). In this figure, 1 is Oligomer 6 and 2 is Oligomer 7.

FIG. 9 shows relative mRNA expression of AR-target genes in treated LNCaP-abl cells quantified by real-time PCR (Veh., EtOH-treated cells; Oligomers 6 or 7, 10 µM). All data were normalized to the housekeeping gene GAPDH.[41] In this figure, 1 is Oligomer 6 and 2 is Oligomer 7.

FIG. 10 shows Oligomers 6 and 7 differentially effect gene expression of LNCaP-abl cells. (A) Clustering analysis of treated LNCaP-abl cells Oligomers 6 and 7 are compared to hormone-activated (DHT) and basal AR activity (siAR) states). Blue represents up-regulated genes, and gray indicates downregulated genes, as specified by the scale color bar (fold-change). (B) Gene ontology (GO) enrichment analysis of treated LNCaP-abl cells (Veh., EtOH-treated cells; Oligomers 6 or 7 (shown relative to Veh. treatment), 1 µM). Heat map showing enrichment score values for GO terms meeting the combined threshold (P≤0.05). Dark blue represents highly enriched GO terms, and light blue indicates depletion of the GO term from the indicated gene set, as specified by the scale color bar. In this figure, 1 is Oligomer 6 and 2 is Oligomer 7.

FIG. 11 shows in vitro fluorescence resonance energy transfer (FRET) analysis of the interaction between purified GST-tagged AR-LBD, terbium-labeled AR-specific anti-GST antibody and fluorescein-labeled AR FxxLF co-activator peptide [increasing concentrations of DHT, Bicalutamide (Bic.), and Oligomer 7]. FRET signal between terbium-labeled antibody and labeled FxxLF-motif peptide, indicative of co-activator recruitment to the AR-LBD, was measured by the 520:495 nm emission ratio after excitation at 340 nm. Error bars represent mean±SD. In this figure, 2 is Oligomer 7.

FIG. 12 shows chromatin immunoprecipitation analysis of AR in treated LNCaP-abl cells. Real-time PCR quantification of PSA-control [R-1881, 10 nM; Oligomers 6 or 7, 1 µM]. Error bars represent mean±SD of triplicates. In this figure, 1 is Oligomer 6 and 2 is Oligomer 7.

FIG. 13 shows fluorescence-activated cell sorting analysis of treated LNCaP-abl cells [Veh., EtOH treated cells; Oligomers 6 or 7, 1 µM]. In this figure, 1 is Oligomer 6 and 2 is Oligomer 7.

FIG. 14 shows clustering analysis of treated LNCaP-abl cells [Oligomers 6 and 7 are compared to hormone-activated (DHT) and basal AR activity (siAR) states]. In this figure, 1 is Oligomer 6 and 2 is Oligomer 7.

FIG. 15 shows Transcriptional activation of AR in the presence of divalent ethisterone conjugates quantified by luciferase activity in LB1 cells [Veh., EtOH treated cells; DHT, 10 nM; Oligomers 6 or 7, 100 nM]. All data presented as mean+SD of triplicates. In this figure, 1 is Oligomer 6 and 2 is Oligomer 7.

DETAILED DESCRIPTION OF THE INVENTION

Definitions

Figure 1:
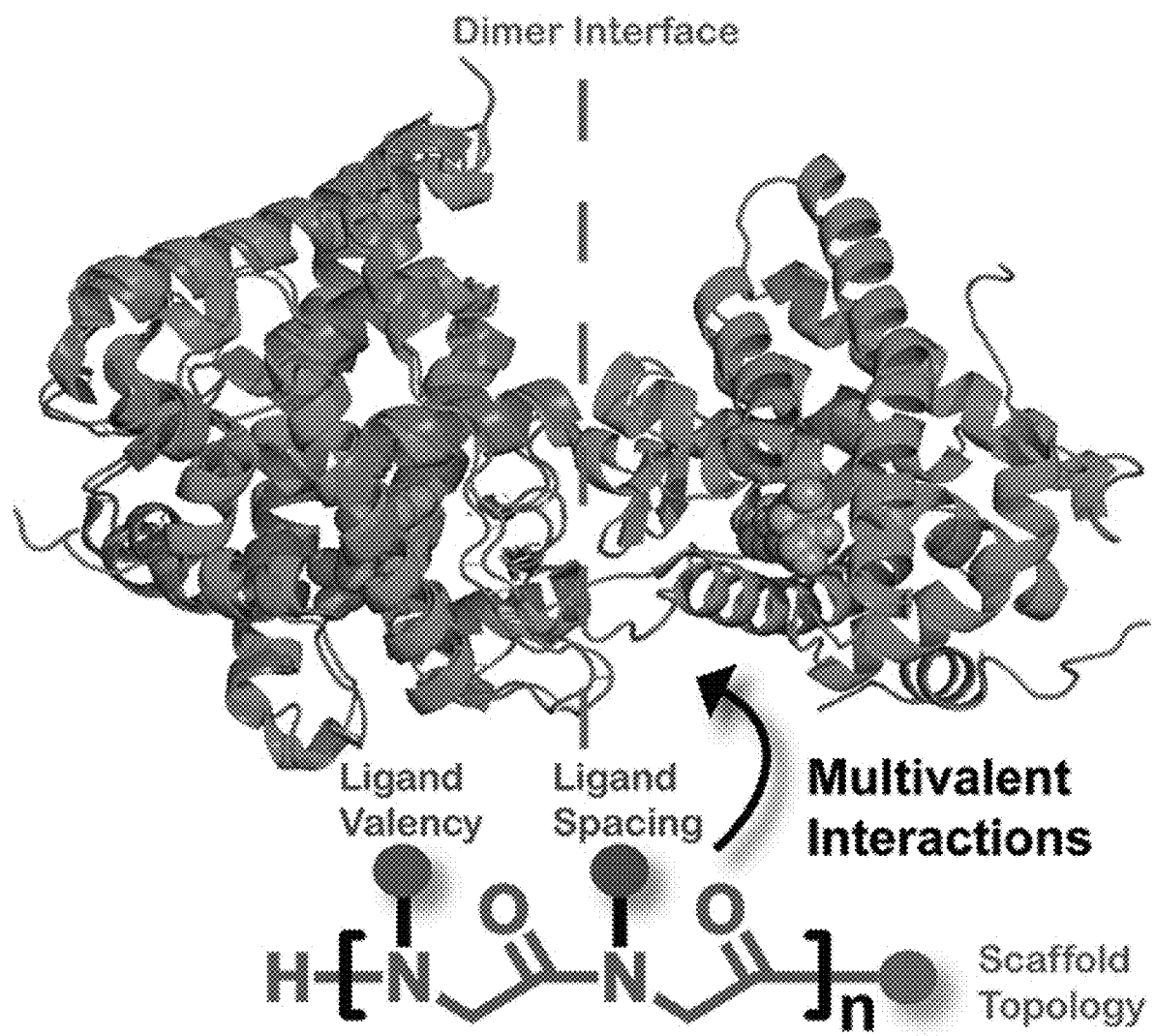
In FIGS. 1, 2, 3, 4, 5 and 6, Compounds (or Conjugates) 1, 2, 3, and 4 refer to Oligomers #1, 2, 3, and 4 (Table 1); Compounds (or Conjugates) 5 and 6 refer to Oligomers #5 and 6 (Table 2); Compound (or Conjugate) 7 refers to Oligomer #7 (Table 3); and Compound (or Conjugate) 8 refers to Oligomer #8 (Table 4).

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —OR$^{29}$ where R$^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$cyclopropyl, OCH$_2$CH$_2$OH, and OCH$_2$CH$_2$NMe$_2$.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR"SO$_2$R", —SO$_2$NR"R'", —C(O)R", —C(O)OR", —OC(O)R", —NR'"C(O)R", —C(O)NR"R'", —NR"R'", or —(CR'"R"")$_m$OR'"; wherein each R" is independently selected from H, $C_1$-$C_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R'" and R"" independently represents H or $C_1$-$C_8$ alkyl.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

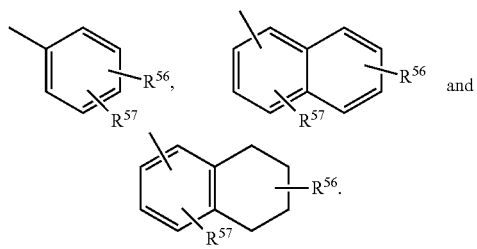

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocycloalkyl, $C_6$-$C_{10}$ aryl, substituted aryl, 5-10 membered heteroaryl.

'Heteroaryl' means an aromatic ring structure, monocyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

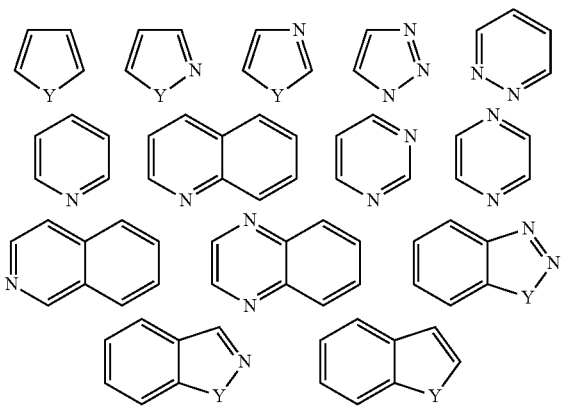

wherein each Y is selected from carbonyl, N, $NR^{65}$, O and S; and $R^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

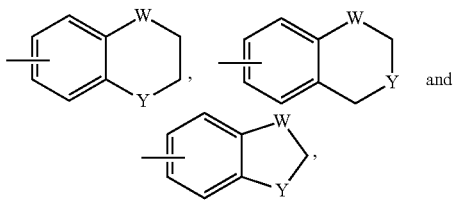

wherein each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

'Unnatural amino acids' means amino acids and corresponding peptoid or synthetic oligomers that are synthesized from single amino acid starting materials. Such unnatural amino acids may be prepared and used individually in accordance with the present invention, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989).

'Pharmaceutically acceptable' means approved by a regulatory agency of the Federal or a state government or listed in the U.S. Pharmacopoeia or other generally recognized pharmacopoeia for use in animals, and more particularly in humans.

'Pharmaceutically acceptable vehicle' refers to a diluent, adjuvant, excipient or carrier with which a compound of the invention is administered.

'Preventing' or 'prevention' refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

'Prodrugs' refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

'Subject' includes humans. The terms 'patient' and 'subject' are used interchangeably herein. Accordingly, a subject can be a mammal, in a particular embodiment a human. In other particular embodiments, a subject can be a bird, a reptile, an amphibian, or a plant.

'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Treating' or 'treatment' of any disease or disorder refers, in one embodiment, to ameliorating the disease or disorder (i.e., arresting or reducing the development of the disease or at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both.

'Compound' refers to the synthetic oligomers of the invention. The terms 'compounds' and 'synthetic oligomers' means the same and are interchangeable. Additionally, the terms oligomers, synthetic oligomers, peptoid and conjugates mean the same and are interchangeable.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term 'isotopic variant' refers to a compound that comprises an unnatural proportion of an isotope of one or more of the atoms that constitute such compound. For example, an 'isotopic variant' of a compound can comprise an unnatural proportion of one or more non-radioactive isotopes, such as for example, deuterium ($^2$H or D), carbon-13 ($^{13}$C), nitrogen-15 ($^{15}$N), or the like. It will be understood that, in a compound comprising an unnatural proportion of an isotope, any example of an atom where present, may vary in isotope composition. For example, any hydrogen may be $^2$H/D, or any carbon may be $^{13}$C, or any nitrogen may be $^{15}$N, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

The Peptoid or Synthetic Oligomers

As set forth earlier herein, the peptoid or synthetic oligomers (peptidomimetic oligomers or conjugates) of the present invention display a variety of biological activities, including the ability to modulate AR activity. Accordingly, the peptoid or synthetic oligomers may be useful therapeutic agents for the treatment of diseases or disorders associated with AR, and particularly, aberrant AR activity.

In one aspect, the present invention introduces versatile multivalent scaffolds to design competitive or non-competitive androgen receptor (AR) modulators with potential therapeutic significance.

In another aspect, the present invention provides methods for preventing, treating or ameliorating medical conditions associated with AR activity.

In yet another aspect, the present invention provides modulators of AR.

In yet another aspect, the present invention provides novel synthetic oligomers. In one embodiment, the synthetic oligomers are peptoid molecules wherein the monomers are attached to each other via a peptoid linkage (C of carbonyl of first monomer is attached to N of second monomer).

In a particular aspect, the present invention provides methods for preventing, treating or ameliorating in a mammal a medical condition, which comprises administering to the mammal an effective medical condition treating amount of a synthetic oligomer according to formula Ia or Ib:

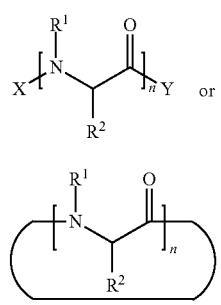

or a pharmaceutically acceptable salt thereof; and stereoisomers, isotopic variants and tautomers thereof;
wherein
each $R^1$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; substituted or unsubstituted cycloalkylalkyl, substituted or unsubstituted heterocycloalkylalkyl, substituted or unsubstituted aralkyl, or substituted or unsubstituted heteroarylalkyl;
each $R^2$ is independently hydrogen, or substituted or unsubstituted alkyl;

n is an integer between 2-45, when the synthetic oligomer is of formula Ia; and n is an integer between 4-45, when the synthetic oligomer is of formula Ib; and
X is H, or substituted or unsubstituted acyl; Y is $NH_2$, OH, acylamino, or acyloxy;
provided that at least one monomer or up to 40 monomers comprises a androgen receptor modulator moiety.

In one embodiment, the medical condition is associated with androgen receptor. In another embodiment, the medical condition is cancer. In one particular embodiment, the medical condition is prostate cancer. In another particular embodiment, the medical condition is breast cancer.

In one embodiment, the medical condition is associated with altered hormone receptor activity. In a particular embodiment, the condition is associated with aberrant AR activity and includes, for example, age-related diseases including, but not limited to sarcopenia, conditions of cachexia and muscle loss induced by diseases including, but not limited to, cancer and AIDS, chronic obstructive pulmonary disease, chronic renal failure, thermal burns, bone and joint diseases, such as osteoporosis, reduction in libido and sexual dysfunction or anemia. In a particular embodiment, the medical condition is cancer. In one particular embodiment, the medical condition is prostate cancer or hyperplasia. In another particular embodiment, the medical condition is colon cancer.

In a further alternative embodiment, the present invention provides antagonists of AR that are thereby effective to treat or alleviate maladies or symptoms of unwanted AR activity, such as AR dependent prostate cancer, male contraception and benign hyperplasia of the prostate, ovarian and breast cancer. In one aspect an oligomer of the invention is an antagonist or partial antagonist and is of use in the prevention and/or treatment of AR dependent tumors and all the conditions in which AR stimulation could be detrimental such as acne, alopecia and hirsutism.

In another aspect, the present invention provides modulators of androgen receptor.

In one particular embodiment, the modulator is a synthetic oligomer according to formula Ia or Ib:

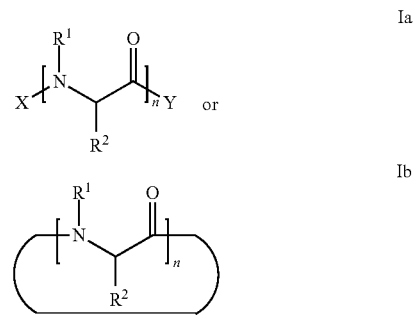

or a pharmaceutically acceptable salt thereof; and stereoisomers, isotopic variants and tautomers thereof;
wherein
each $R^1$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; substituted or unsubstituted cycloalkylalkyl, substituted or unsubstituted heterocycloalkylalkyl, substituted or unsubstituted aralkyl, or substituted or unsubstituted heteroarylalkyl;

each $R^2$ is independently hydrogen, or substituted or unsubstituted alkyl;

n is an integer between 2-45, when the synthetic oligomer is of formula Ia; and n is an integer between 4-45, when the synthetic oligomer is of formula Ib; and X is H, or substituted or unsubstituted acyl; Y is $NH_2$, OH, acylamino, or acyloxy; provided that at least one monomer or up to 40 monomers comprises a androgen receptor modulator moiety.

In yet another aspect, the present invention provides synthetic oligomers according to formula Ia or Ib.

In one embodiment, with respect to the modulator or the synthetic oligomer, the oligomer is other than

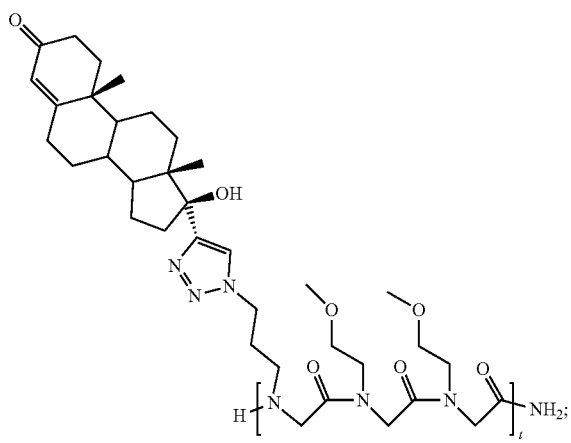

and wherein t is 2 or 3.

In one embodiment, with respect to the method, the modulator or the synthetic oligomer, the synthetic oligomer comprises at least one triazolyl moiety.

In one embodiment, with respect to the method, the modulator or the synthetic oligomer, the monomer comprising the androgen receptor modulator moiety comprises a triazolyl moiety.

In one embodiment, with respect to the method, the modulator or the synthetic oligomer the monomer comprising the androgen receptor modulator moiety comprises 5-androsten-3b,17a-dihydroxy-17a-triazolyl moiety. In another embodiment, the androgen receptor modulator moiety comprises 5-androstan-17b-hydroxy-3-oxo-17a-triazolyl moiety. In another embodiment, the androgen receptor modulator moiety comprises 4-estren-18-homo-17b-hydroxy-3-oxo-17a-triazolyl moiety. In another embodiment, the androgen receptor modulator moiety comprises 4-estren-17b-hydroxy-3-oxo-17a-triazolyl moiety. In another embodiment, the androgen receptor modulator moiety comprises 4-estren-17b-acetoxy-3-oxo-17a-triazolyl moiety. In another embodiment, the androgen receptor modulator moiety comprises 4-estren-17b-acetoxy-3-oximino-17a-triazolyl moiety. In another embodiment, the androgen receptor modulator moiety comprises 5(10)-estren-17b-hydroxy-3-oxo-17a-triazolyl moiety.

In one embodiment, with respect to the method, the modulator or the synthetic oligomer, the monomer comprising the androgen receptor modulator moiety is according to formula II:

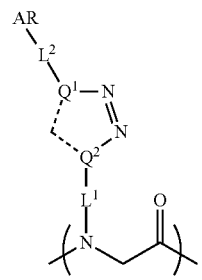

wherein
$L^1$ is $C_1$-$C_{10}$ alkylene;
$L^2$ is a single bond or $C_1$-$C_{10}$ alkylene;
$Q^1$ is N, and $Q^2$ is C; or $Q^1$ is C, and $Q^2$ is N;
one of the dotted bonds is a single bond and the other is a double bond;
AR is

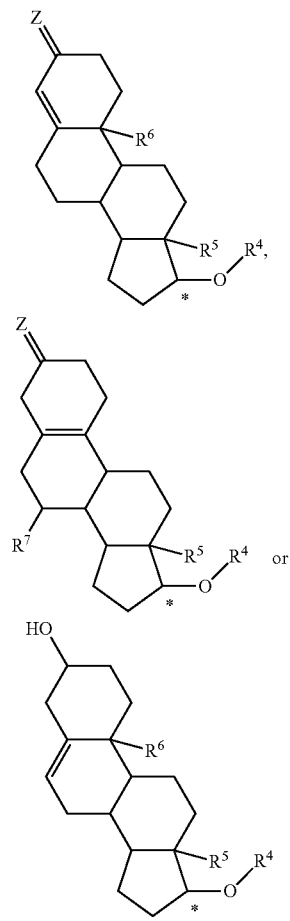

Z is O or N—O—$R^{3a}$; $R^{3a}$ is H or substituted or unsubstituted alkyl;
$R^4$ is H or acyl; $R^5$ is substituted or unsubstituted alkyl; each $R^6$ and $R^7$ is independently H or substituted or unsubstituted alkyl; and * denotes the attachment point.

In another embodiment, with respect to the method, the modulator or the synthetic oligomer, the monomer comprising the androgen receptor modulator moiety is according to formula IIIa, or IIIb:

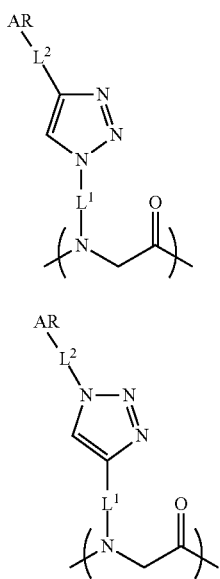

IIIa or

IIIb wherein

L$^1$, L$^2$, and AR are as described for formula II.

In one embodiment, with respect to the formula II, IIIa, or IIIb, L$^1$ is —CH$_2$—, —CH$_2$—CH$_2$—, —CH$_2$—CH$_2$—CH$_2$—, —CH$_2$—CH$_2$—CH$_2$—CH$_2$—, or —CH$_2$—CH$_2$—CH$_2$—CH$_2$—CH$_2$—.

In one embodiment, with respect to the formula II, IIIa, or IIIb, L$^2$ is —CH$_2$—, —CH$_2$—CH$_2$—, —CH$_2$—CH$_2$—CH$_2$—, —CH$_2$—CH$_2$—CH$_2$—CH$_2$—, or —CH$_2$—CH$_2$—CH$_2$—CH$_2$—CH$_2$—.

In one particular embodiment, with respect to the formula II, IIIa, or IIIb, L$^2$ is a single bond.

In another embodiment, with respect to the method, the modulator or the synthetic oligomer, the monomer comprising the androgen receptor modulator moiety is according to formula IVa, IVb, or IVc:

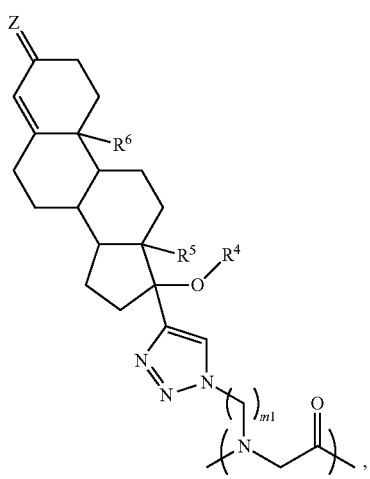

IVa

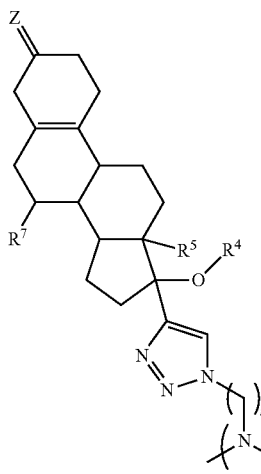

IVb or

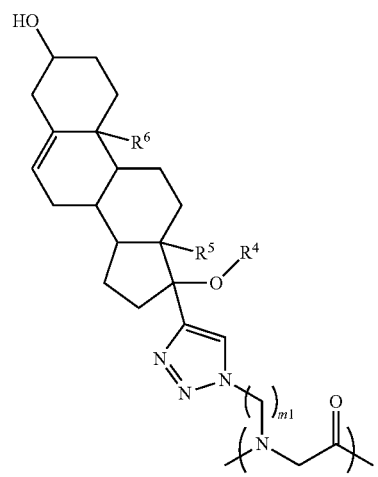

IVc wherein Z is O or N—O—R$^{3a}$; R$^{3a}$ is H or substituted or unsubstituted alkyl; R$^4$ is H or acyl; R$^5$ is substituted or unsubstituted alkyl; each R$^6$ and R$^7$ is independently H or substituted or unsubstituted alkyl; and the subscript m1 is independently an integer between 1-10.

In another embodiment, with respect to the method, the modulator or the synthetic oligomer, the monomer comprising the androgen receptor modulator moiety is according to formula Va, Vb, or Vc:

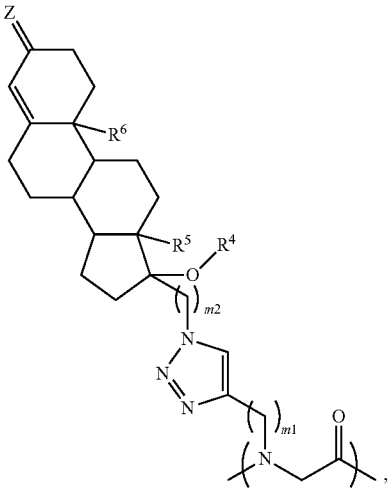

Va

-continued

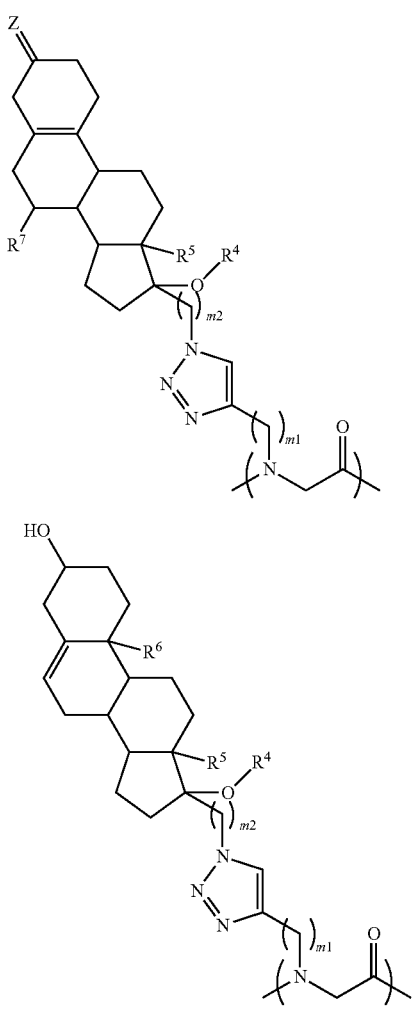

Vb or

Vc wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is independently an integer between 1-10; and the subscript m2 is independently an integer between 0-10.

In one embodiment, with respect to the method, the modulator or the synthetic oligomer, $R^1$ is alkyl, unsubstituted or substituted with halo, alkoxy, amino, guanidino, or hydroxyl.

In one embodiment, with respect to the method, the modulator or the synthetic oligomer, $R^1$ is substituted or unsubstituted aralkyl.

In one embodiment, with respect to the method, the modulator or the synthetic oligomer, $R^1$ is benzyl or phenethyl; each unsubstituted or substituted with 1-5 groups independently selected from halo, alkoxy, alkyl, amido, sulfonamido, hydroxyl, guanidino, nitro, or phenyl.

In one embodiment, with respect to the method, the modulator or the synthetic oligomer, $R^1$ is substituted or unsubstituted heteroarylalkyl.

In one embodiment, with respect to the method, the modulator or the synthetic oligomer, $R^1$ is pyridyl, pyrimidyl, pyrazinyl, indolyl, benzimidazolyl, quinolinyl, or isoquinolinyl; each unsubstituted or substituted with 1-5 groups independently selected from halo, alkoxy, alkyl, amido, sulfonamido, hydroxyl, guanidino, nitro, or phenyl.

In one embodiment, with respect to the method, the modulator or the synthetic oligomer, $R^1$ is furanyl, thiazolyl, imidazolyl, oxazolyl, isoxazolyl, or triazolyl; each unsubstituted or substituted with 1-2 groups independently selected from halo, alkoxy, alkyl, amido, sulfonamido, hydroxyl, guanidino, nitro, or phenyl.

In one embodiment, with respect to the method, the modulator or the synthetic oligomer, the synthetic oligomer is according to formula Ia or Ib:

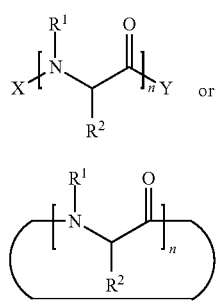

Ia or

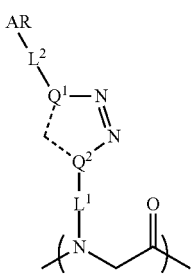

Ib or a pharmaceutically acceptable salt thereof; and stereoisomers, isotopic variants and tautomers thereof;
wherein
each $R^1$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; substituted or unsubstituted cycloalkylalkyl, substituted or unsubstituted heterocycloalkylalkyl, substituted or unsubstituted aralkyl, or substituted or unsubstituted heteroarylalkyl;
each $R^2$ is independently hydrogen, or substituted or unsubstituted alkyl;
n is an integer between 2-45, when the synthetic oligomer is of formula Ia; and n is an integer between 4-45, when the synthetic oligomer is of formula Ib; and
X is H, or substituted or unsubstituted acyl; Y is $NH_2$, OH, acylamino, or acyloxy; provided that:
i) at least one monomer or up to 40 monomers are according to formula II:

II wherein
$L^1$ is $C_1$-$C_{10}$ alkylene;
$L^2$ is a single bond or $C_1$-$C_{10}$ alkylene;
$Q^1$ is N, and $Q^2$ is C; or $Q^1$ is C, and $Q^2$ is N;
one of the dotted bonds is a single bond and the other is a double bond;

AR is

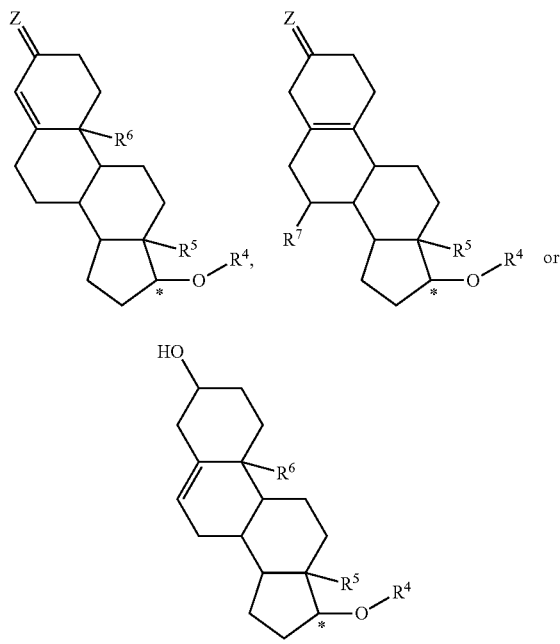

Z is O or N—O—R$^{3a}$; R$^{3a}$ is H or substituted or unsubstituted alkyl;

R$^4$ is H or acyl; R$^5$ is substituted or unsubstituted alkyl; each R$^6$ and R$^7$ is independently H or substituted or unsubstituted alkyl; and * denotes the attachment point;

and the rest of the monomers are according to formula VIa, VIb, or VIc:

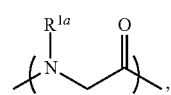

VIa

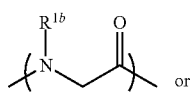

VIb or

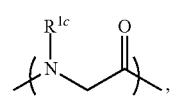

VIc wherein each R$^{1a}$ is independently unsubstituted alkyl, substituted alkyl, or cycloalkylalkyl;

each R$^{1b}$ is independently aminoalkyl, guanidinoalkyl (H$_2$N—C(=NH)—NH-alkyl), or N-containing heteroarylalkyl;

each R$^{1c}$ is independently substituted or unsubstituted aryl, substituted or unsubstituted aralkyl, substituted or unsubstituted heteroarylalkyl, or substituted or unsubstituted diarylalkyl.

In another aspect, the present invention provides synthetic oligomers according to formula Ia or Ib:

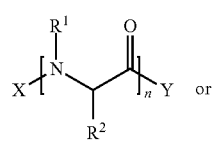

Ia or

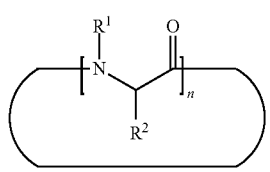

Ib or a pharmaceutically acceptable salt thereof; and stereoisomers, isotopic variants and tautomers thereof;

wherein each R$^1$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; substituted or unsubstituted cycloalkylalkyl, substituted or unsubstituted heterocycloalkylalkyl, substituted or unsubstituted aralkyl, or substituted or unsubstituted heteroarylalkyl;

each R$^2$ is independently hydrogen, or substituted or unsubstituted alkyl;

n is an integer between 2-45, when the synthetic oligomer is of formula Ia; and n is an integer between 4-45, when the synthetic oligomer is of formula Ib; and X is H, or substituted or unsubstituted acyl; Y is NH$_2$, OH, acylamino, or acyloxy; provided that:

i) at least one monomer or up to 40 monomers are according to formula II:

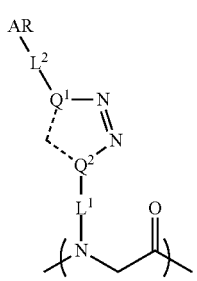

II wherein

L$^1$ is C$_1$-C$_{10}$ alkylene;

L$^2$ is a single bond or C$_1$-C$_{10}$ alkylene;

Q$^1$ is N, and Q$^2$ is C; or Q$^1$ is C, and Q$^2$ is N;

one of the dotted bonds is a single bond and the other is a double bond;

AR is

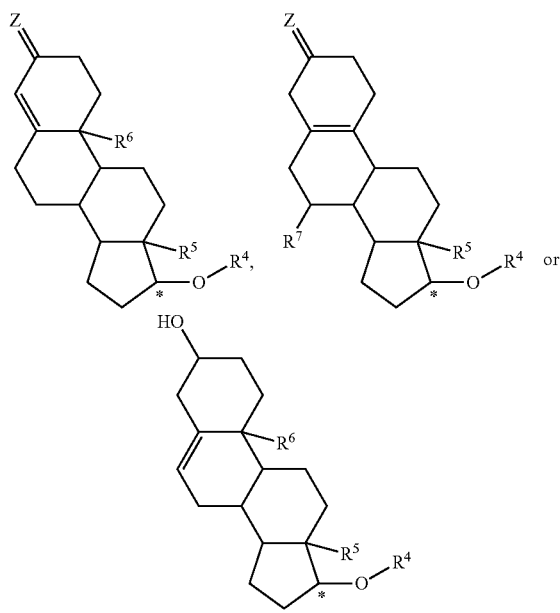

Z is O or N—O—$R^{3a}$; $R^{3a}$ is H or substituted or unsubstituted alkyl;
$R^4$ is H or acyl; $R^5$ is substituted or unsubstituted alkyl; each $R^6$ and $R^7$ is independently H or substituted or unsubstituted alkyl; and * denotes the attachment point;
and the rest of the monomers are according to formula VIa, VIb, or VIc:

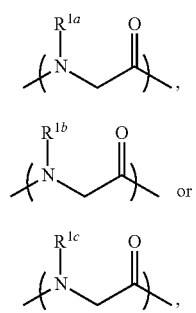

wherein
each $R^{1a}$ is independently unsubstituted alkyl, substituted alkyl, or cycloalkylalkyl;
each $R^{1b}$ is independently aminoalkyl, guanidinoalkyl ($H_2N$—C(=NH)—NH-alkyl), or N-containing heteroarylalkyl;
each $R^{1c}$ is independently substituted or unsubstituted aryl, substituted or unsubstituted aralkyl, substituted or unsubstituted heteroarylalkyl, or substituted or unsubstituted diarylalky.

In one embodiment, with respect to the method, the modulator or the synthetic oligomer, the oligomer is according to formula Ia; the subscript n is 2-45, 2-40, 2-35, 2-30, 2-25, 2-20, 2-15, 2-10, 2-5, or 2-3.

In one embodiment, with respect to the method, the modulator or the synthetic oligomer, the oligomer is according to formula Ib; the subscript n is 4-45, 4-40, 4-35, 4-30, 4-25, 4-20, 4-15, 4-10, 4-8, or 4-6.

In one embodiment, with respect to the method, the modulator or the synthetic oligomer, the oligomer is according to formula Ia; the subscript n is 3, 6, 9, or 18; 1, 2, 3, or 6 of monomers are according to formula II; Z is O, $Q^2$ is N; $R^4$ is H; each $R^5$ and $R^6$ is Me; and m is 1; then each $R^{1a}$, when present, is other than methoxyethyl.

In one embodiment, with respect to the method, the modulator or the synthetic oligomer, the monomer according to formula II is a monomer according to formula Ma, or IIIb:

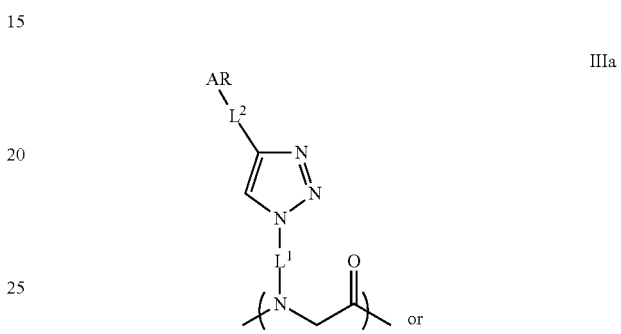

wherein $L^1$, $L^2$, and AR are as described for formula II.

In one embodiment, with respect to the method, the modulator or the synthetic oligomer, the monomer according to formula II is a monomer according to formula IVa, IVb, or IVc:

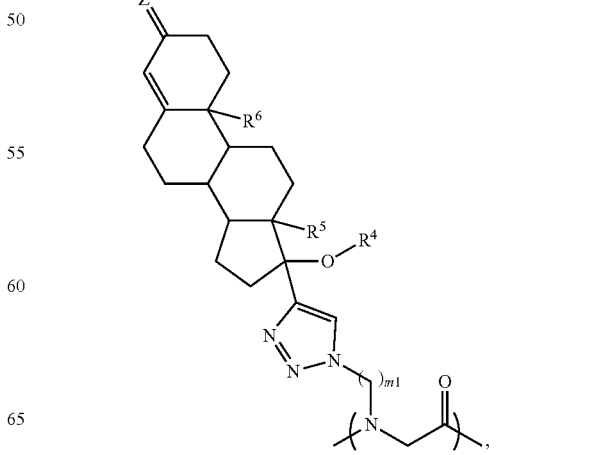

IVb

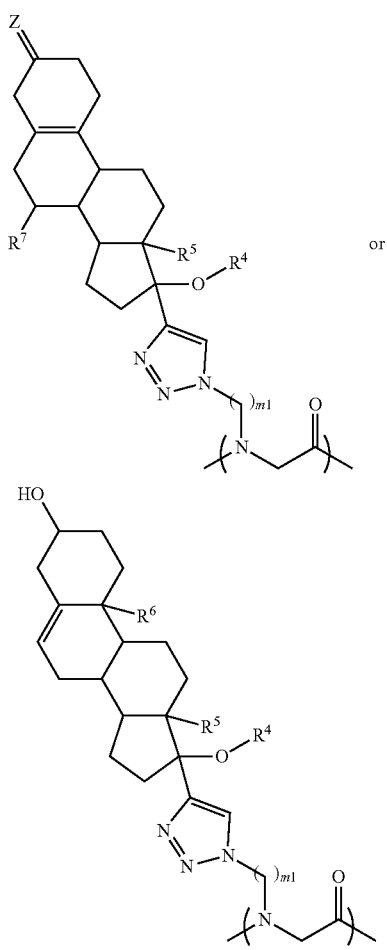

IVc wherein Z is O or N—O—R$^{3a}$; R$^{3a}$ is H or substituted or unsubstituted alkyl; R$^4$ is H or acyl; R$^5$ is substituted or unsubstituted alkyl; each R$^6$ and R$^7$ is independently H or substituted or unsubstituted alkyl; and the subscript m1 is independently an integer between 1-10.

In one embodiment, with respect to the method, the modulator or the synthetic oligomer, the monomer according to formula II is a monomer according to formula Va, Vb, or Vc:

Va

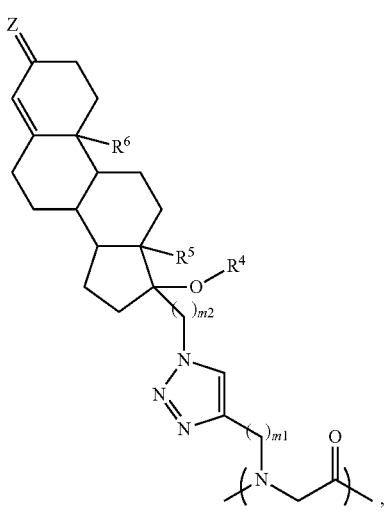

Vb

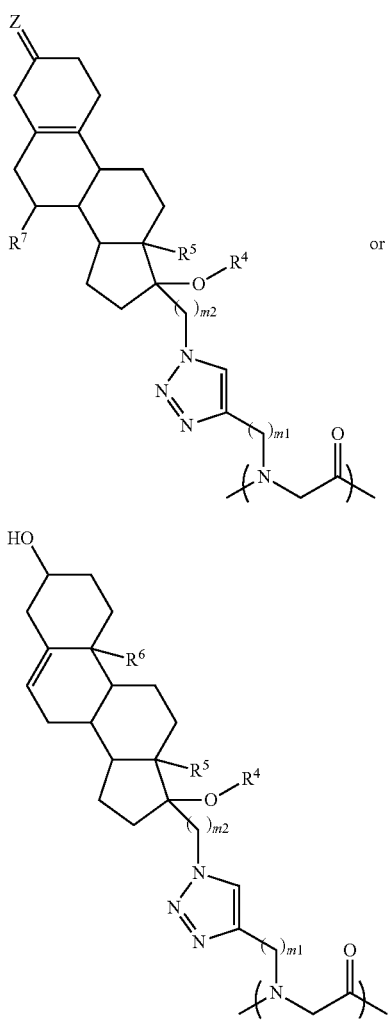

Vc wherein Z is O or N—O—R$^{3a}$; R$^{3a}$ is H or substituted or unsubstituted alkyl; R$^4$ is H or acyl; R$^5$ is substituted or unsubstituted alkyl; each R$^6$ and R$^7$ is independently H or substituted or unsubstituted alkyl; and the subscript m1 is independently an integer between 1-10; and the subscript m2 is independently an integer between 0-10.

In one embodiment, with respect to the method, the modulator or the synthetic oligomer, R$^2$ is H.

In one embodiment, with respect to the method, the modulator or the synthetic oligomer, the subscript m1 is 1, 2, 3, or 4.

In one embodiment, with respect to the method, the modulator or the synthetic oligomer, the subscript m1 is 3 or 4.

In one embodiment, with respect to the method, the modulator or the synthetic oligomer, the subscript m1 is 4.

In one embodiment, with respect to the method, the modulator or the synthetic oligomer, the subscript m2 is 0, 1, 2, 3, or 4.

In one embodiment, with respect to the method, the modulator or the synthetic oligomer, the subscript m2 is 3 or 4.

In one embodiment, with respect to the method, the modulator or the synthetic oligomer, the subscript m2 is 3.

In one embodiment, with respect to the method, the modulator or the synthetic oligomer, the oligomer is according to formula VII:

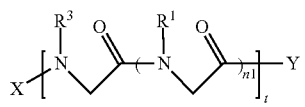

wherein X, Y and $R^1$ are as in formulae Ia and Ib; the subscript t is an integer between 1 to 15; the subscript n1 is an integer between 1-10; each $R^3$ is

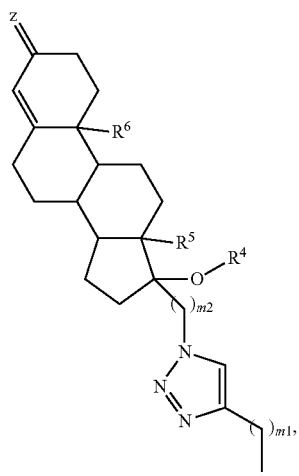

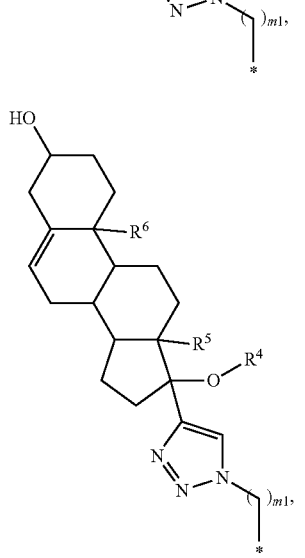

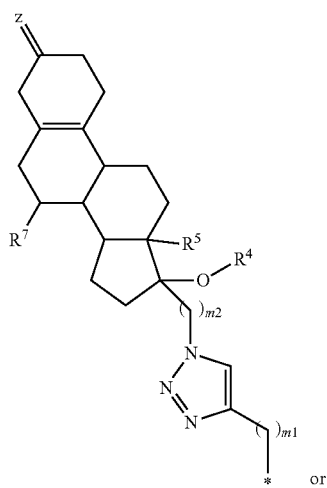

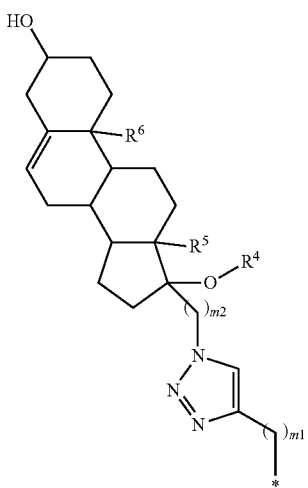

wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10 and * denotes the attachment point;

or a pharmaceutically acceptable salt thereof; and stereoisomers, isotopic variants and tautomers thereof.

In one embodiment, with respect to the method, the modulator or the synthetic oligomer, the oligomer is according to formula VII, and the subscript t is 1, 2, 3, 4, 5, or 6.

In one embodiment, with respect to the method, the modulator or the synthetic oligomer, the oligomer is according to formula VII, and the subscript t is 1, 2, 3, or 6.

In one embodiment, with respect to the method, the modulator or the synthetic oligomer, the oligomer is according to formula VIII:

VIII

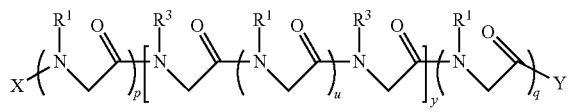

wherein X, Y and $R^1$ are as in formulae Ia and Ib; the subscript u is an integer between 0 to 15; each of the subscripts p, q, and y is an integer between 1-10; each $R^3$ is IVa'

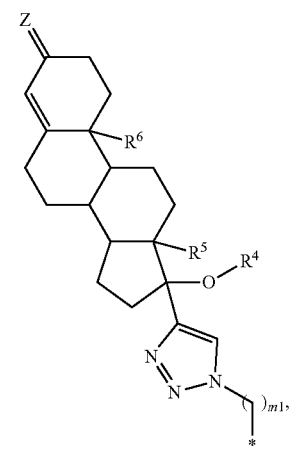

IVb'

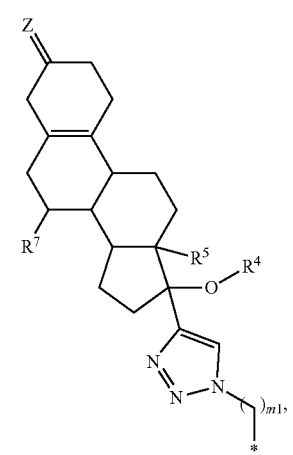

-continued

IVc'

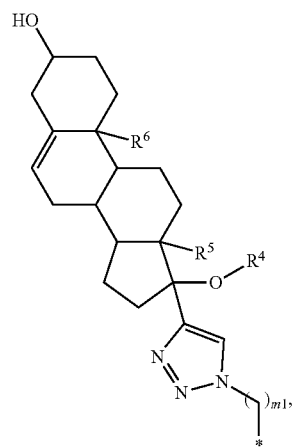

Va'

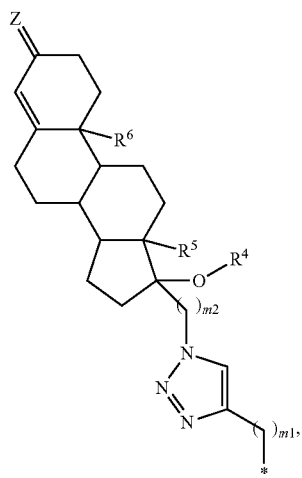

Vb'

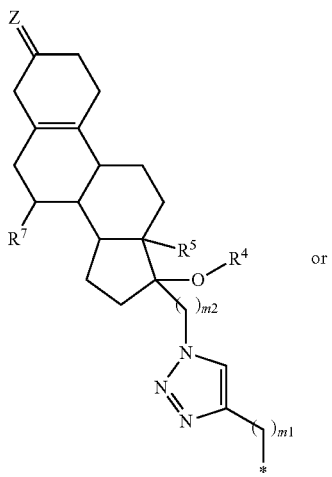

or

-continued

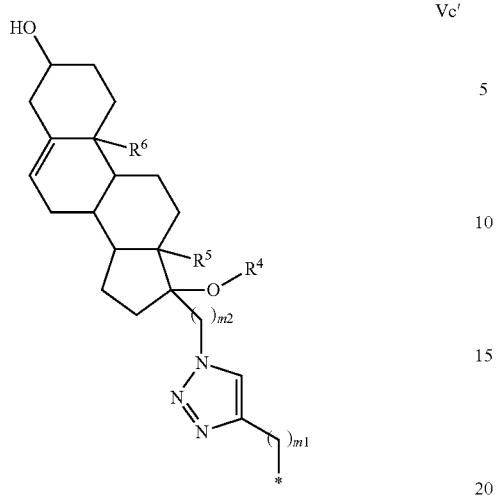
Vc'

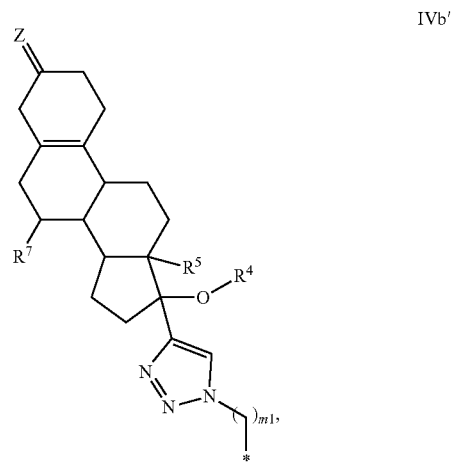
IVb' wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10 and * denotes the attachment point;
or a pharmaceutically acceptable salt thereof; and stereoisomers, isotopic variants and tautomers thereof.

In one embodiment, with respect to the method, the modulator or the synthetic oligomer, the oligomer is according to formula VIII, and the subscript u is 5, 6, 7, 8, or 14.

In one embodiment, with respect to the method, the modulator or the synthetic oligomer, the oligomer is according to formula IX:

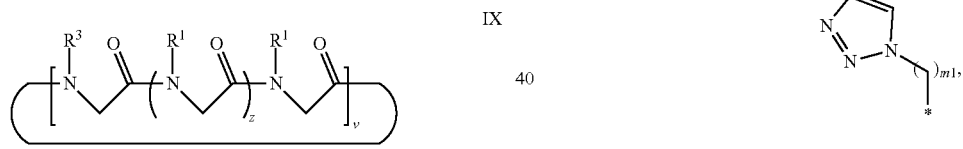
IX wherein X, Y and $R^1$ are as in formulae Ia and Ib; the subscript v is an integer between 1 to 15; the subscripts z is an integer between 1-10; each $R^3$ is

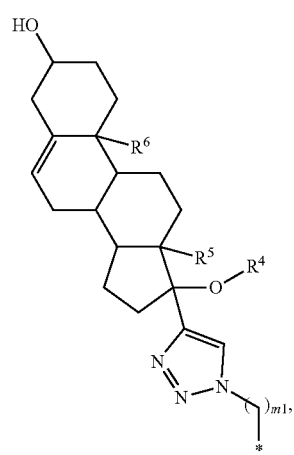
IVc'

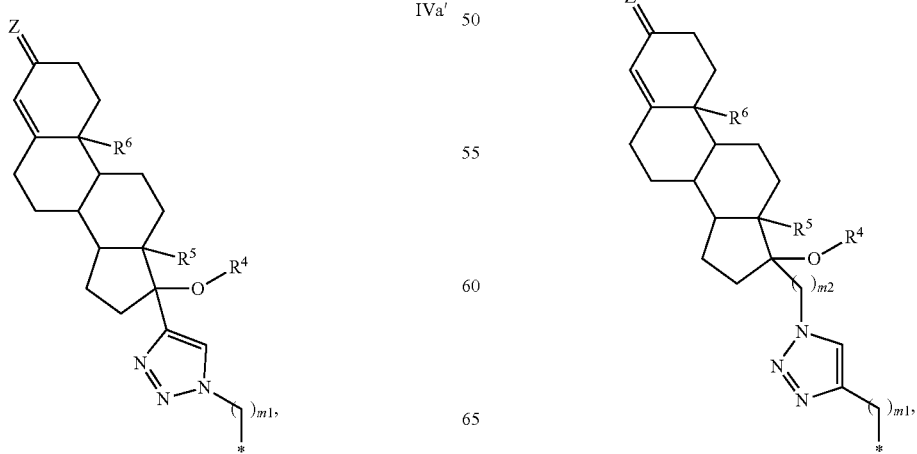
IVa'
Va'

-continued

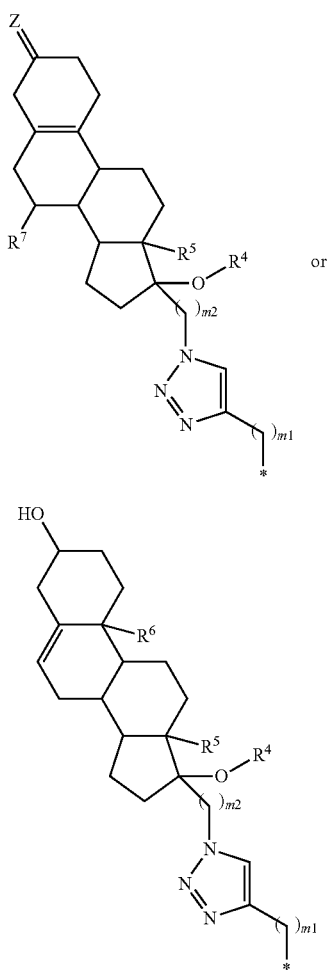

wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10; and * denotes the attachment point;
or a pharmaceutically acceptable salt thereof; and stereoisomers, isotopic variants and tautomers thereof.

In one embodiment, with respect to the method, the modulator or the synthetic oligomer, the oligomer is according to formula IX, and the subscript v is 2, 3, 4, 5, 6, 7, or 8.

In one embodiment, with respect to the method, the modulator or the synthetic oligomer, each $R^1$ or each $R^{1a}$ is independently selected from unsubstituted alkyl, substituted alkyl, cycloalkylalkyl, aminoalkyl, guanidinoalkyl ($H_2N$—C(=NH)—NH-alkyl), N-containing heteroarylalkyl; substituted or unsubstituted aryl, substituted or unsubstituted aralkyl, substituted or unsubstituted heteroarylalkyl, and substituted or unsubstituted diarylalkyl.

In one embodiment, with respect to the method, the modulator or the synthetic oligomer, each $R^1$ or each $R^{1a}$ is independently unsubstituted alkyl, substituted alkyl, or cycloalkylalkyl.

In one embodiment, with respect to the method, the modulator or the synthetic oligomer, each $R^1$ or each $R^{1a}$ is independently Me, Et, n-Pr, i-Pr, n-Bu, or i-Bu.

In one embodiment, with respect to the method, the modulator or the synthetic oligomer, each $R^1$ or each $R^{1a}$ is independently haloalkyl.

In one embodiment, with respect to the method, the modulator or the synthetic oligomer, each $R^1$ or each $R^{1a}$ is independently trifluormethyl, fluoromethyl, or chloromethyl.

In one embodiment, with respect to the method, the modulator or the synthetic oligomer, each $R^1$ or each $R^{1a}$ is independently alkoxyalkyl.

In one embodiment, with respect to the method, the modulator or the synthetic oligomer, each $R^1$ or each $R^{1a}$ is independently methoxymethyl, methoxyethyl, methoxypropyl, or methoxybutyl, ethoxymethyl, or ethoxyethyl.

In one embodiment, with respect to the method, the modulator or the synthetic oligomer, each $R^1$ or each $R^{1a}$ is independently cyclopropylmethyl, cyclobutylmethyl, cyclopentylmethyl, or cyclohexylmethyl.

In one embodiment, with respect to the method, the modulator or the synthetic oligomer, each $R^1$ or each $R^{1a}$ is independently aminoalkyl, or guanidinoalkyl.

In one embodiment, with respect to the method, the modulator or the synthetic oligomer, each $R^1$ or each $R^{1a}$ is independently aminoethyl, aminopropyl, dimethyaminoethyl, or dimethylaminopropyl.

In one embodiment, with respect to the method, the modulator or the synthetic oligomer, each $R^1$ or each $R^{1a}$ is independently aralkyl or heteroarylalkyl.

In one embodiment, with respect to the method, the modulator or the synthetic oligomer, each $R^1$ or each $R^{1a}$ is independently benzyl or phenethyl; each unsubstituted or substituted with 1-3 groups independently selected from halo, alkoxy, alkyl, amido, sulfonamido, hydroxyl, guanidino, nitro, or phenyl.

In one embodiment, with respect to the method, the modulator or the synthetic oligomer, each $R^1$ or each $R^{1a}$ is independently substituted or unsubstituted heteroarylalkyl.

In one embodiment, with respect to the method, the modulator or the synthetic oligomer, each $R^1$ or each $R^{1a}$ is independently pyridyl, pyrimidyl, pyrazinyl, indolyl, benzimidazolyl, quinolinyl, or isoquinolinyl; each unsubstituted or substituted with 1-5 groups independently selected from halo, alkoxy, alkyl, amido, sulfonamido, hydroxyl, guanidino, nitro, or phenyl.

In one embodiment, with respect to the method, the modulator or the synthetic oligomer, each $R^1$ or each $R^{1a}$ is independently furanyl, thiazolyl, imidazolyl, oxazolyl, isoxazolyl, or triazolyl; each unsubstituted or substituted with 1-2 groups independently selected from halo, alkoxy, alkyl, amido, sulfonamido, hydroxyl, guanidino, nitro, or phenyl.

In one embodiment, with respect to the method, the modulator or the synthetic oligomer, the oligomer is according to formula X:

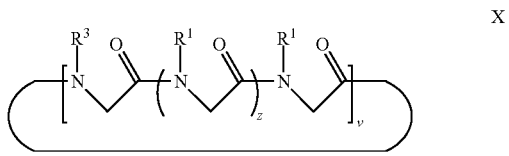

wherein $R^3$ is as described herein; each $R^1$ is independently unsubstituted alkyl, substituted alkyl, cycloalkylalkyl, aminoalkyl, guanidinoalkyl ($H_2N$—C(=NH)—NH-alkyl), or N-containing heteroarylalkyl; the subscript v is an integer between 2 to 15; and the subscript z is an integer between 1-10;
or a pharmaceutically acceptable salt thereof; and stereoisomers, isotopic variants and tautomers thereof.

In one embodiment, with respect to the method, the modulator or the synthetic oligomer, the oligomer is according to formula X, and the subscript v is 2, 3, 4, 5, 6, 7, or 8.

In one particular embodiment, with respect to the method, the modulator or the synthetic oligomer, each $R^{1a}$ is methoxyethyl.

In one particular embodiment, with respect to the method, the modulator or the synthetic oligomer, each $R^3$ is

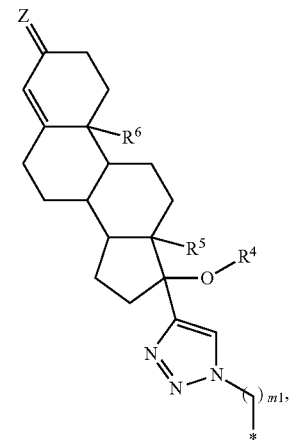

IVa'

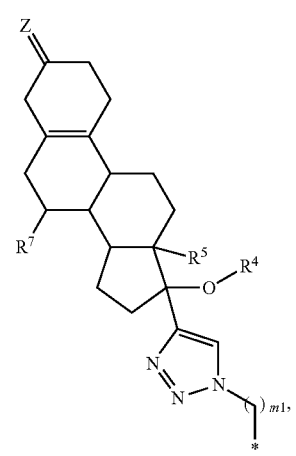

IVb'

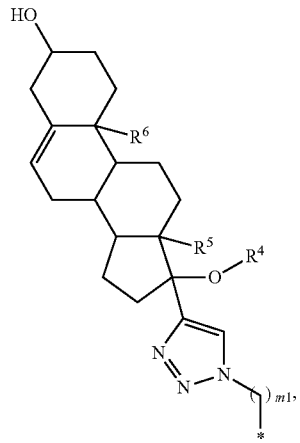

IVc'

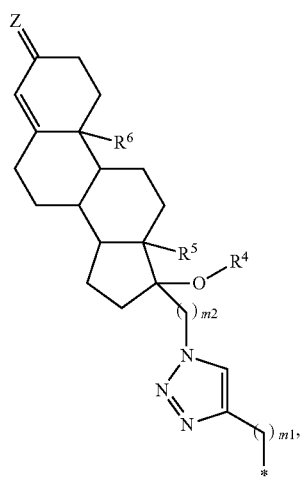

Va'

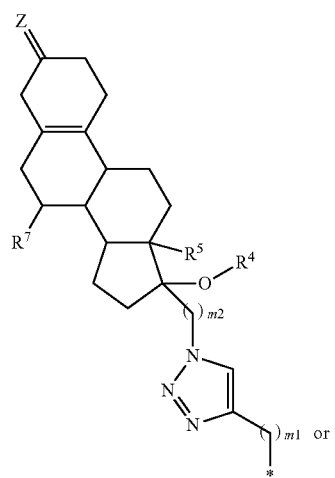

Vb'

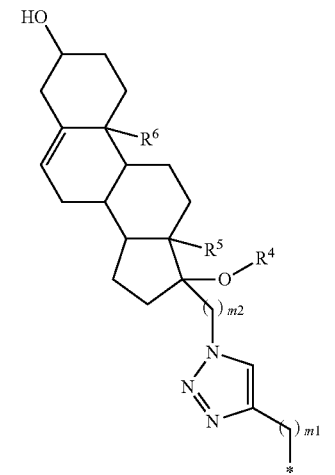

Vc' wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10; and * denotes the attachment point;

In one embodiment, with respect to the method, the method, the modulator or the synthetic oligomer, the oligomer is according to formula Ia or Ib; and $R^2$ is H.

In one embodiment, with respect to the method, the method, the modulator or the synthetic oligomer, the oligomer is according to formula Ia-X; and each $R^{1a}$, or each $R^1$, when present, is methoxyethyl.

In one embodiment, with respect to the method, the method, the modulator or the synthetic oligomer, the oligomer is according to formula Ia-X; and each $R^{1a}$, or each $R^1$, when present, is other than methoxyethyl. In one embodiment, with respect to the method, the modulator or the synthetic oligomer, the oligomer is according to formula Ia-X; and each $R^{1a}$, or each $R^1$, when present, is independently unsubstituted alkyl, substituted alkyl, or cycloalkylalkyl.

In one embodiment, with respect to the method, the modulator or the synthetic oligomer, the oligomer is according to formula Ia-X; and each $R^{1a}$, or each $R^1$, when present, is Me, Et, n-Pr, i-Pr, n-Bu, sec-Bu, i-Bu, or cyclohexylmethyl.

In one embodiment, with respect to the method, the modulator or the synthetic oligomer, the oligomer is according to formula Ia-X; and each $R^{1a}$, or each $R^1$, when present, is independently Me, Et, n-Pr, i-Pr, n-Bu, or i-Bu.

In one embodiment, with respect to the method, the modulator or the synthetic oligomer, the oligomer is according to formula Ia-X; and each $R^{1a}$, or each $R^1$, when present, is independently haloalkyl.

In one embodiment, with respect to the method, the modulator or the synthetic oligomer, the oligomer is according to formula Ia-X; and each $R^{1a}$, or each $R^1$, when present, is independently trifluormethyl, fluoromethyl, or chloromethyl.

In one embodiment, with respect to the method, the modulator or the synthetic oligomer, the oligomer is according to formula Ia-X; and each $R^{1a}$, or each $R^1$, when present, is independently alkoxyalkyl.

In one embodiment, with respect to the method, the modulator or the synthetic oligomer, the oligomer is according to formula Ia-X; and each $R^{1a}$, or each $R^1$, when present, is independently methoxymethyl, methoxyethyl, methoxypropyl, or methoxybutyl, ethoxymethyl, or ethoxyethyl.

In one embodiment, with respect to the method, the modulator or the synthetic oligomer, the oligomer is according to formula Ia-X; and each $R^{1b}$, or each $R^1$, when present, is independently cyclopropylmethyl, cyclobutylmethyl, cyclopentylmethyl, or cyclohexylmethyl.

In one embodiment, with respect to the method, the modulator or the synthetic oligomer, the oligomer is according to formula Ia-X; and each $R^{1b}$, or each $R^1$, when present, is independently aminoalkyl, or guanidinoalkyl.

In one embodiment, with respect to the method, the modulator or the synthetic oligomer, the oligomer is according to formula Ia-X; and each $R^{1b}$, or each $R^1$, when present, is independently aminoethyl, aminopropyl, dimethyaminoethyl, or dimethylaminopropyl.

In one embodiment, with respect to the method, the modulator or the synthetic oligomer, the oligomer is according to formula Ia-X; and each $R^{1c}$, or each $R^1$, when present, is independently aralkyl or heteroarylalkyl.

In one embodiment, with respect to the method, the modulator or the synthetic oligomer, the oligomer is according to formula Ia-X; and each $R^{1c}$, or each $R^1$, when present, is phenyl or benzyl, unsubstituted or substituted with one or more groups selected from alkyl, halo, hydroxy, amino, nitro, and alkoxy.

In one embodiment, with respect to the method, the modulator or the synthetic oligomer, the oligomer is according to formula Ia-X; and each $R^{1c}$, or each $R^1$, when present, is phenethyl, unsubstituted or substituted with one or more groups selected from alkyl, halo, hydroxy, amino, nitro, and alkoxy.

In one embodiment, with respect to the method, the modulator or the synthetic oligomer, the oligomer is according to formula Ia-X; and each $R^{1c}$, or each $R^1$, when present, is 2-naphthyl, unsubstituted or substituted with one or more groups selected from alkyl, halo, hydroxy, amino, nitro, and alkoxy.

In one embodiment, with respect to the method, the modulator or the synthetic oligomer, the oligomer is according to formula Ia-X; and each $R^{1c}$, or each $R^1$, when present, is 2,2-diphenylethyl, unsubstituted or substituted with one or more groups selected from alkyl, halo, hydroxy, amino, nitro, and alkoxy.

In one embodiment, with respect to the method, the modulator or the synthetic oligomer, the oligomer is according to formula Ia-X; and each $R^{1c}$, or each $R^1$, when present, $R^{1c}$ is furanyl or thienyl, unsubstituted or substituted with one or more groups selected from alkyl, halo, hydroxy, amino, nitro, and alkoxy.

In one embodiment, with respect to the method, the modulator or the synthetic oligomer, the oligomer is according to formula Ia-X; and each $R^{1b}$, or each $R^1$, when present, is aminomethyl, 2-aminoethyl, 3-aminopropyl, 4-aminobutyl, 5-aminopentyl, or 6-aminohexyl.

In one embodiment, with respect to the method, the modulator or the synthetic oligomer, the oligomer is according to formula Ia-X; and each $R^{1b}$, or each $R^1$, when present, is 3-aminopropyl.

In one embodiment, with respect to the method, the modulator or the synthetic oligomer, the oligomer is according to formula Ia-X; and each $R^{1b}$, or each $R^1$, when present, is guanidinoalkyl.

In one embodiment, with respect to the method, the modulator or the synthetic oligomer, the oligomer is according to formula Ia-X; and each $R^{1b}$, or each $R^1$, when present, is guanidinomethyl, 2-guanidinoethyl, 3-guanidinopropyl, 4-guanidinobutyl, 5-guanidinopentyl, or 6-guanidinohexyl.

In one embodiment, with respect to the method, the modulator or the synthetic oligomer, the oligomer is according to formula Ia-X; and each $R^{1b}$, or each $R^1$, when present, is 4-guanidinobutyl.

In one embodiment, with respect to the method, the modulator or the synthetic oligomer, the oligomer is according to formula Ia-X; and each $R^{1b}$, or each $R^1$, when present, is imidazolylmethyl, 2-imidazolylethyl, 3-imidazolylpropyl, 4-imidazolylbutyl, 5-imidazolylpentyl, or 6-imidazolylhexyl.

In one embodiment, with respect to the method, the modulator or the synthetic oligomer, the oligomer is according to formula Ia-X; and each $R^{1b}$, or each $R^1$, when present, is methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, with respect to the method, the modulator or the synthetic oligomer, the oligomer is according to formula Ia-X; and X, when present, is acetyl.

In one embodiment, with respect to the method, the modulator or the synthetic oligomer, the oligomer is according to formula Ia-X; and X, when present, is H.

In one embodiment, with respect to the method, the modulator or the synthetic oligomer, the oligomer is according to formula Ia-X; and Y, when present, is NH$_2$.

In one embodiment, Z is O. In another embodiment, Z is N—OH. In yet another embodiment, Z is N—O—CH$_2$CO$_2$H.

In one embodiment, R$^7$ is H or Me. In one particular embodiment, R$^7$ is H.

In one embodiment, R$^4$ is H or COMe. In one particular embodiment, R$^4$ is H.

In one embodiment, R$^5$ is Me or Et. In one particular embodiment, R$^5$ is Me.

In one embodiment, R$^6$ is H or Me. In one particular embodiment, R$^6$ is Me.

In one embodiment, the subscript m is 1.

In one embodiment, with respect to the method, the modulator or the synthetic oligomer, the oligomer is according to formula Ia-X; and R$^3$, when present, is

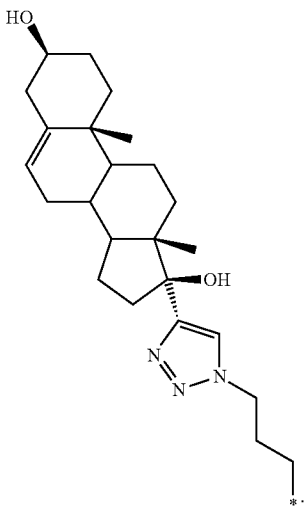

In one embodiment, with respect to the method, the modulator or the synthetic oligomer, the oligomer is according to formula Ia-X; and R$^3$, when present, is

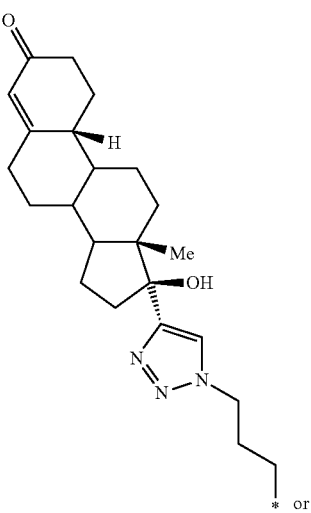

or

-continued

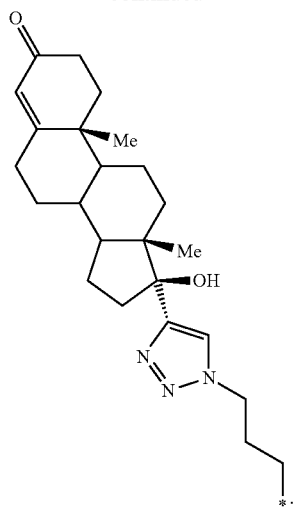

In one embodiment, with respect to the method, the modulator or the synthetic oligomer, the oligomer is according to formula Ia-X; and R$^3$, when present, is

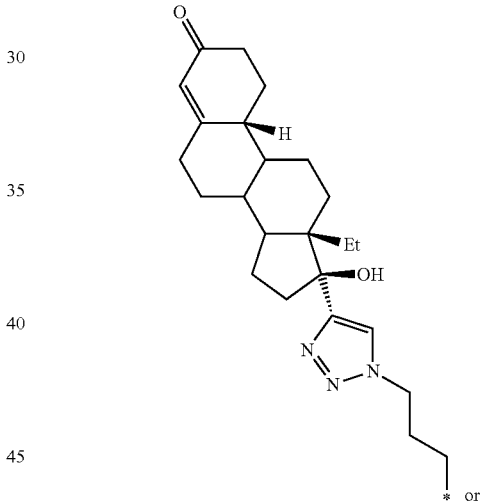

or

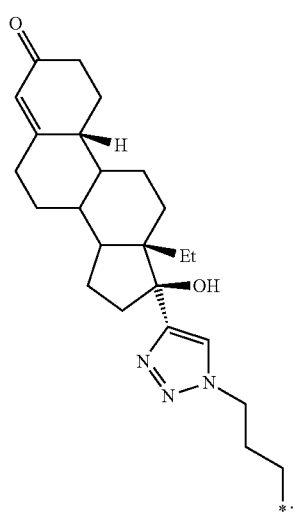

In one embodiment, with respect to the method, the modulator or the synthetic oligomer, the oligomer is according to formula Ia-X; and R³, when present, is

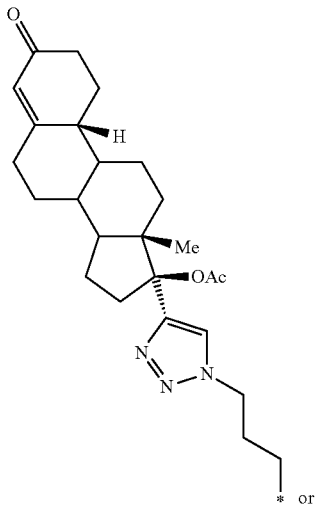

* or

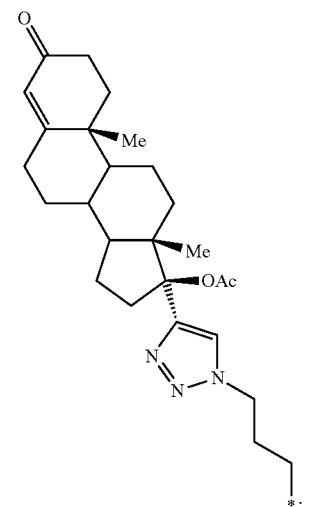

In one embodiment, with respect to the method, the modulator or the synthetic oligomer, the oligomer is according to formula Ia-X; and R³, when present, is

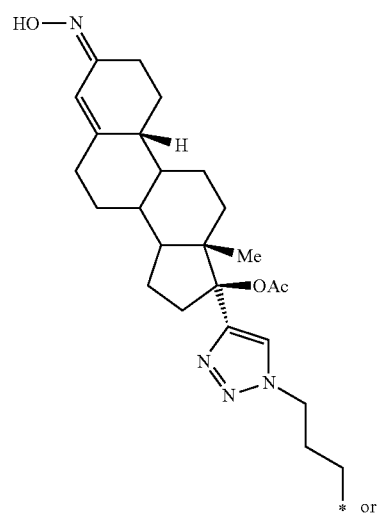

* or

-continued

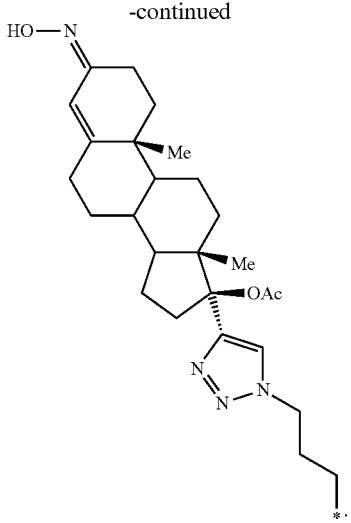

In one embodiment, with respect to the method, the modulator or the synthetic oligomer, the oligomer is according to formula Ia-X; and R³, when present, is

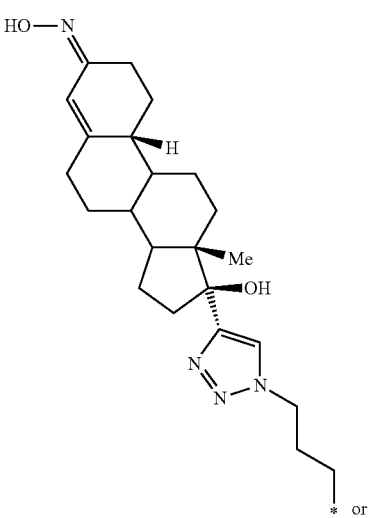

* or

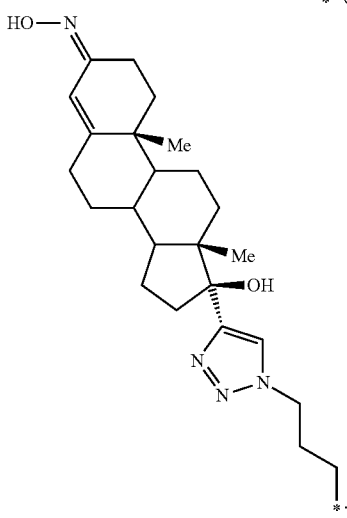

In one embodiment, with respect to the method, the modulator or the synthetic oligomer, the oligomer is according to formula Ia-X; and R³, when present, is

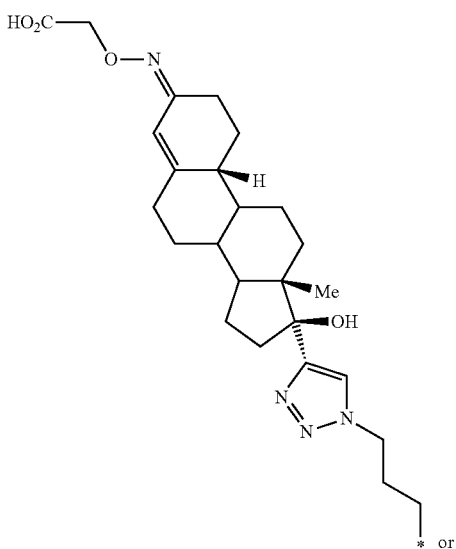

In one embodiment, with respect to the method, the modulator or the synthetic oligomer, the oligomer is according to formula Ia-X; and $R^3$, when present, is

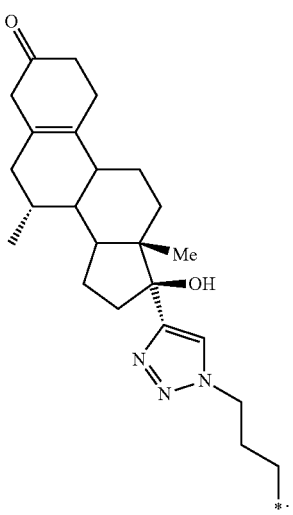

In one embodiment, 'acyl' refers to a radical —C(O)R$^{20}$, where R$^{20}$ is Me, Et, n-Pr, i-Pr, n-Bu, i-Bu, pentyl, hexyl, heptyl, octyl, nonyl, or decyl.

In one embodiment 'acyl' refers to a radical —C(O)R$^{20}$, where R$^{20}$ is $C_{11}$-$C_{20}$ alkyl.

In one particular embodiment, 'acyl' is lauroyl, tridecanoyl, myristoyl, pentadecanoyl, palmitoyl, or cetoyl.

In one embodiment, 'acyl' refers to a radical —C(O)R$^{20}$, where R$^{20}$ is $C_3$-$C_{10}$ cycloalkyl. In another embodiment, R$^{20}$ is cyclopropyl, cyclobutyl, cyclopentyl or cyclohexyl.

In one embodiment, 'acyl' refers to a radical —C(O)R$^{20}$, where R$^{20}$ is —(CH$_2$)$_{t'}$(C$_3$-C$_{10}$ cycloalkyl), and t' is 1, 2, or 3. In another embodiment R$^{20}$ is —CH$_2$—(C$_3$-C$_{10}$ cycloalkyl). In yet another embodiment R$^{20}$ is cyclopropylmethyl or cyclobutylmethyl.

In yet another embodiment, 'acyl' is acetyl unsubstituted or substituted with cycloalkyl, or phenyl.

In yet another embodiment, 'acyl' is acetyl, lauroyl, tridecanoyl, myristoyl, pentadecanoyl, palmitoyl, caproyl, benzoyl, cetyl, decyl, acetyl, phenyl acetyl, cyclohexyl acetyl, or valeroyl.

In yet another embodiment, 'acyl' is acetyl, or palmitoyl.

In yet another embodiment, 'acyl' is glucuronyl residue.

In most particular embodiment, 'acyl' is acetyl or MeCO—.

In one embodiment, with respect to the method, the modulator or the synthetic oligomer, the oligomer is according to formula Ia, and the oligomer is according to formula XI:

XI

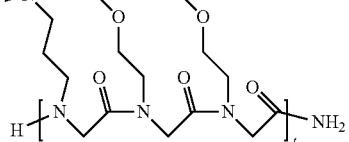

or a pharmaceutically acceptable salt thereof; and stereoisomers, isotopic variants and tautomers thereof;

and wherein the subscript t is 1, 2, 3, 4, 5, 6, 7, 8, or 9.

In one embodiment, the subscript t is 1, 2, 3, or 6.

In one embodiment, with respect to the method, the modulator or the synthetic oligomer, the oligomer is according to formula Ia, and the oligomer is according to formula XII:

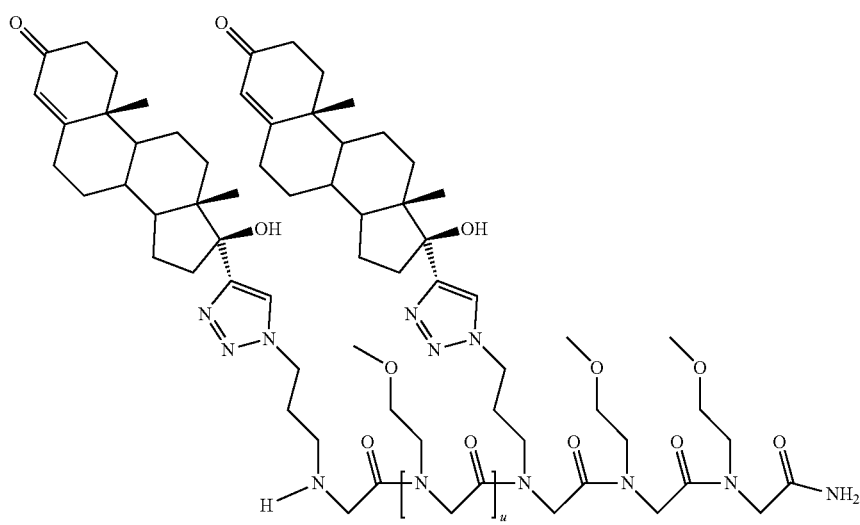

XII or a pharmaceutically acceptable salt thereof; and stereoisomers, isotopic variants and tautomers thereof;

and wherein the subscript u is 1, 2, 3, 4, 5, 6, 7, 8, 9, 10, 11, or 12.

In one embodiment, the subscript u is 5 or 8.

In one embodiment, with respect to the method, the modulator or the synthetic oligomer, the oligomer is according to formula Ia, and the oligomer is according to formula XIII:

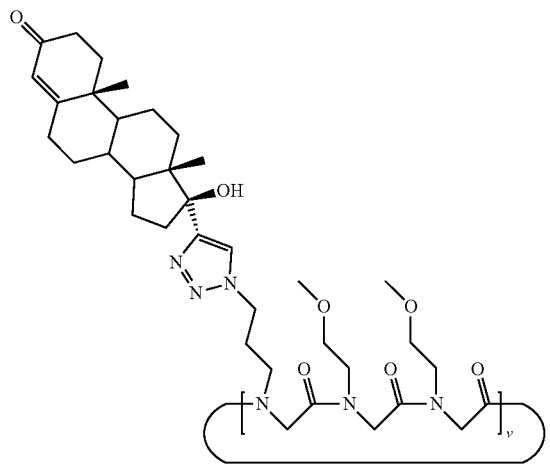

XIII or a pharmaceutically acceptable salt thereof; and stereoisomers, isotopic variants and tautomers thereof;

and wherein the subscript v is 2, 3, 4, 5, 6, 7, 8, or 9.

In one embodiment, the subscript v is 2.

In one embodiment, with respect to the synthetic oligomer of formula Ia or Ib, the oligomer is selected from the oligomers listed in Table 1, 2, or 3.

In one embodiment, with respect to the synthetic oligomer of formula Ia or Ib, the oligomer is selected from the oligomers listed in Table 4.

In a particular aspect, the present invention provides methods for modulating androgen receptor activity in a human cancer cell, in which said receptor is present, comprising contacting the cell with an effective amount of an oligomer according to formula Ia, Ib, VII, VIII, IX, X, XI, XII or XIII; or a pharmaceutically acceptable salt thereof; and stereoisomers, isotopic variants and tautomers thereof.

In one embodiment, with respect to the method, the cell is LNCaP-abl cell.

In one embodiment, with respect to the method, the cancer is prostate cancer.

In one embodiment, with respect to the method, the cancer is castrate-resistant prostate cancer.

In another particular aspect, the present invention provides methods for treating cancer comprising modulating androgen receptor activity in a human cancer cell by contacting the cell with an effective amount of an oligomer according to formula Ia, Ib, VII, VIII, IX, X, XI, XII or XIII; or a pharmaceutically acceptable salt thereof; and stereoisomers, isotopic variants and tautomers thereof.

In one embodiment, with respect to the method, the cell is LNCaP-abl cell.

In one embodiment, with respect to the method, the cancer is prostate cancer.

In one embodiment, with respect to the method, the cancer is castrate-resistant prostate cancer.

In certain aspects and where appropriate, the present invention extends to the preparation of prodrugs and derivatives of the peptoids of the invention. Prodrugs are derivatives which have cleavable groups and become by solvolysis or under physiological conditions the peptoid of the invention, which are pharmaceutically active, in vivo.

In one embodiment, the invention provides a pharmaceutical composition comprising a pharmaceutically acceptable carrier and a pharmaceutically effective amount of the peptoid of formula Ia or Ib.

In one embodiment, the invention provides a pharmaceutical composition of the synthetic oligomer of formula Ia or Ib, comprising a pharmaceutically acceptable carrier, and the carrier is a parenteral carrier, oral or topical carrier.

In one embodiment, the invention provides a method for preventing, treating, ameliorating or managing a disease or condition which comprises administering to a patient in need of such prevention, treatment, amelioration or management, a prophylactically or therapeutically effective amount of the pharmaceutical composition of the synthetic oligomer of formula Ia or Ib.

In one embodiment, the disease or condition is or results from cancer.

In one embodiment, the disease or condition is AR related condition.

In one embodiment, the invention provides a method for preventing, treating, ameliorating or managing a disease or condition, which comprises administering to a patient in need of such prevention, treatment, amelioration or management a prophylactically or therapeutically acceptable amount of a peptoid or synthetic oligomer of formula Ia or Ib, or the pharmaceutical composition thereof, wherein the disease or condition results from.

Pharmaceutical Compositions

When employed as pharmaceuticals, the peptoid compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptoid compounds in combination with one or more therapeutic compounds generally prescribed for the treatment of AR related conditions. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptoid compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, vaginal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The peptoid or synthetic oligomers may be administered as therapeutic agents to a subject afflicted with AR related conditions. Such conditions have been recited earlier herein. The ability of the peptoid or synthetic oligomers to modulate AR strongly suggests that oligomers of the invention will confer therapeutic benefit to subjects to whom the oligomers are administered.

Further to the above and in light of the results presented herein, the peptoids and compositions comprising same may be used to advantage in the prevention and/or treatment of AR related conditions.

The complexes of this invention can be administered as the sole active agent or they can be administered in combination with other agents, including like-acting agents and other active derivatives.

A skilled practitioner would appreciate that the choice as to which compound or compounds of the invention are well suited to a particular application must take into consideration such variables as the severity of the disease or condition, mode of administration, and duration of administration, and the cost:benefit ratio associated with synthesis of linear versus cyclic peptides.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptoid oligomers that have been listed hereinabove. The peptoid or synthetic oligomers of the invention may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yl-oxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); 0-Benzotriazole-N,N,N',N'-tetramethyl-uronium-hexafluoro-phosphate (HBTU).

Representative Synthetic Method

Preparation of Oligomers of the Invention

All Peptoid oligomers described herein were synthesized on Rink Amide resin (0.64 mmol g$^{-1}$) (Novabiochem, San Diego, Calif.), using either standard Fmoc solid-phase peptide synthesis or modifications of the same to incorporate 'submonomer chemistry' (Figliozzi et al, Synthesis of N-substituted glycine peptoid libraries. In *Methods Enzymol.*, Academic Press: 1996; Vol. 267, pp 437-447; Bartlett et al., *Proc. Natl. Acad. Sci. U.S.A* 1992, 89, 9367-9371) wherever needed as depicted in scheme 1. Peptoids can be synthesized in parallel using a fully automated robotic workstation (Charybdis™ Instruments) with software protocol written in-house. All peptoids oligomers are synthesized at room temperature. Fmoc Amino Acids were purchased from Novabiochem. The submonomer amines were purchased from Alfa Aesar and Sigma-Aldrich. O-Benzotriazole-N,N,N',N'-tetramethyl-uronium-hexafluoro-phosphate (HBTU) were purchased from Novabiochem and N-methyl Morpholine (Nmm) were purchased from AlfaAesar. Bromoacetic acid was purchased from Sigma-Aldrich. N,N'diisopropylcarbodiimide (DIC) was purchased from Chem-Impex International. Trifluoroacetic acid (TFA) was purchased from Fisher Scientific. Triisopropylsilane (TIPS) was purchased from Sigma-Aldrich. Other reagents and solvents were obtained from commercial sources and used without additional purification.

Peptoids can be synthesized on solid support to allow generation of monodisperse products, offering distinct advantages over other multivalent display approaches (e.g. random copolymers or dendrimers).[23] The sequence-specific assembly of peptoids enables precise tuning of ligand valency and spacing to potentially enhance affinity and specificity for corresponding biomolecular targets.[24] In addition, the peptoid scaffold can be used as a versatile platform for optimizing other properties critical for biological activity, such as the ability to alter the topology of the scaffold to achieve optimal ligand-receptor interactions.[25]

A series of peptoid-based multivalent oligomers were prepared to evaluate the influence of valency, spacing and conformational ordering on AR activity. Cu-catalyzed azide-alkyne [3+2]cycloaddition (CuAAC) 'click' reactions is or can be used to oligomer ethisterone, a 17α-ethynyl homologue of DHT, to peptoid side-chains, thus generating a family of multivalent oligomers.[28] Ethisterone was chosen as a ligand because it is known to compete for AR binding and suppresses levels of AR transcriptional activation relative to DHT.[27,28] Additionally, the ethynyl moiety provides accessibility to CuAAC reactions, a powerful synthetic tool due to its bioorthogonality, high yields and mild reaction conditions.[26]

Using modified solid-phase peptoid synthesis protocols, linear and cyclic peptoid oligomers containing azido-alkyl functionalized side chains were introduced at specific positions in the oligomer sequence.[29] Following oligomerization (and cyclization as required), the peptoid scaffolds were used as substrates for CuAAC-mediated conjugation of ethisterone ligands (Scheme 1). In order to alleviate steric congestion, the ethisterone moieties were oligomer d at least three residues apart (i, i+3) in the peptoid oligomer sequence. To enhance overall water solubility, all other intervening positions in the peptide sequence included the hydrophilic monomer N-(methoxyethyl)glycine.

A set of linear peptoid oligomer s were synthesized with 1, 2, 3 or 6 ethisterone ligands (oligomer s 1-4) displayed along the peptoid backbone. Additional divalent peptoid oligomer s containing ethisterone ligands separated by five (oligomer 5) or eight (oligomer 6) intervening monomer units were synthesized (Scheme 1). A cyclic divalent construct (oligomer 7) to constrain the spatial disposition of the ethisterone moieties was also generated.

Scheme 1: Synthesis of Peptoid oligomers of the Invention[a]

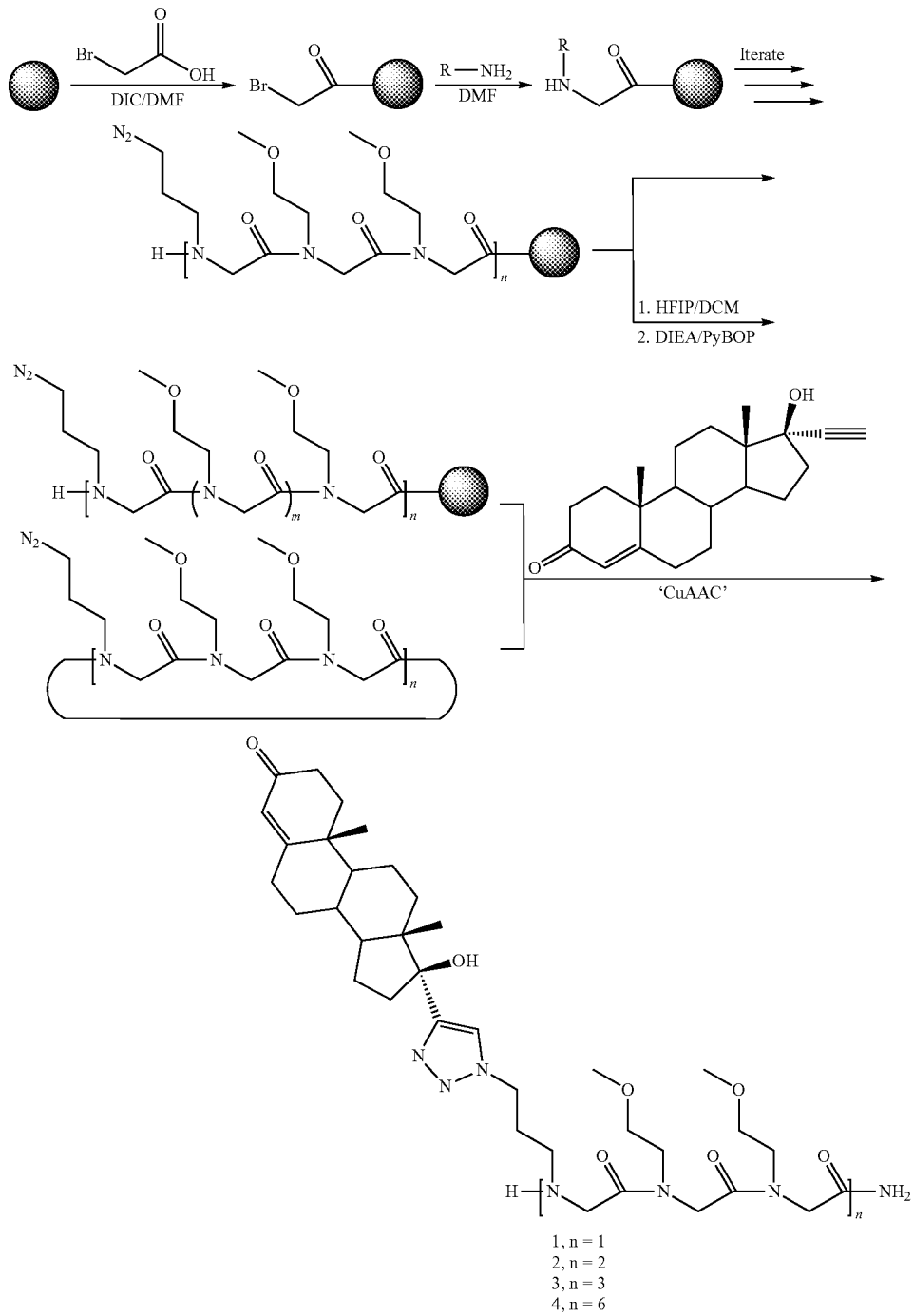

1, n = 1
2, n = 2
3, n = 3
4, n = 6

-continued

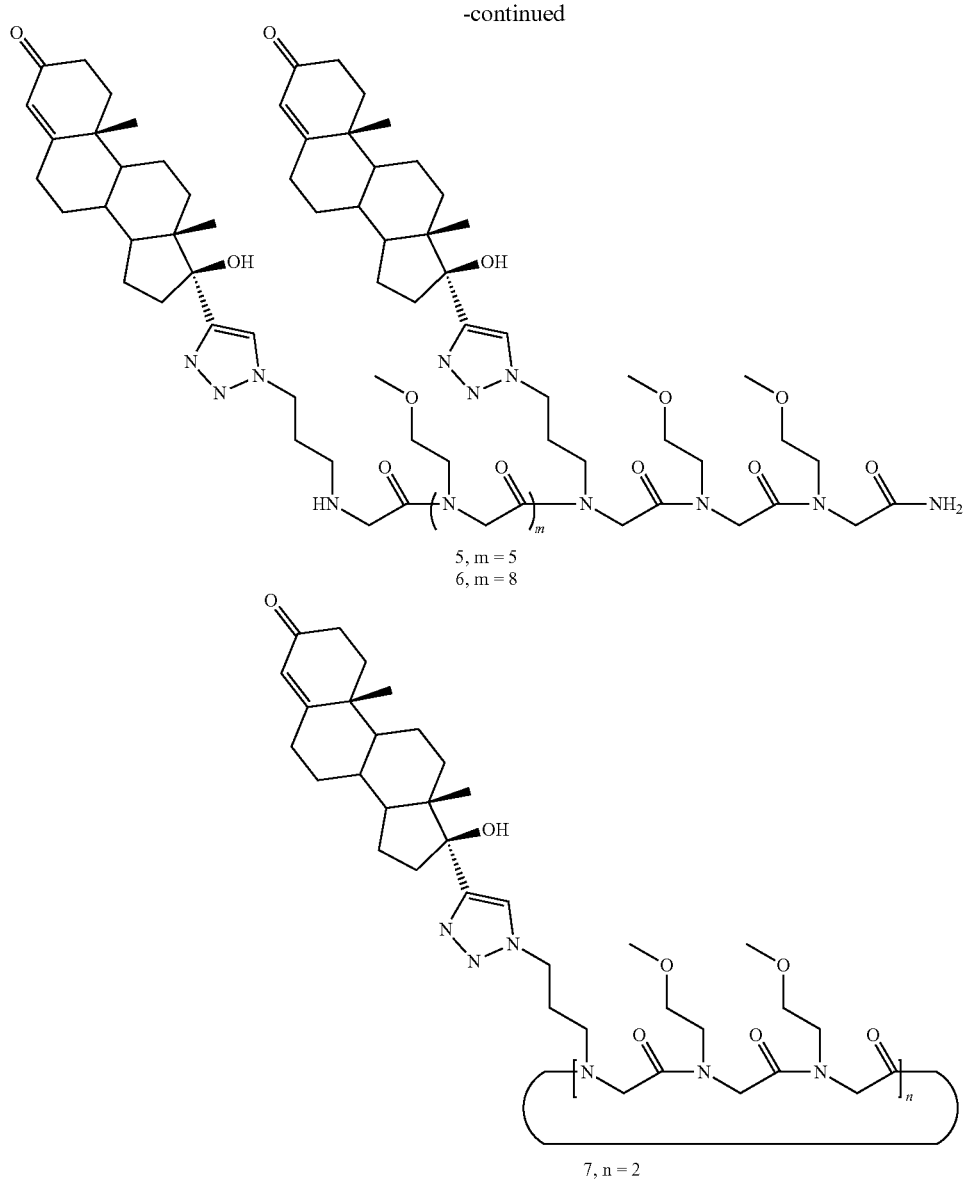

5, m = 5
6, m = 8

7, n = 2

[a] Rink Amide and 2-chlorotrityl chloride resin were used to generate linear and cyclic peptoid oligomers, respectively. Rink Amide resin was cleaved with 95% trifluoroacetic acid following conjugation reactions.

Synthesis of 3-Azido-1-Aminopropane

3-Chloro-1-aminopropane (6.5 g, 0.050 mol) and sodium azide (9.75 g, 0.150 mol) were dissolved in water (150 mL) and the solution was heated in an oil bath for 18 hours at 80° C. The reaction was removed, concentrated (50%) and cooled to 0° C. Diethyl ether (50 mL) and potassium hydroxide (4 g, 0.071 mol) were added and organic layer was separated. Aqueous layer was washed twice (20 mL ether) and combined organic layers were dried over magnesium sulfate, filtered and concentrated to yield 3-azido-1-aminopropane as a yellow liquid. $^1$H NMR (CDCl$_3$ 400 MHz) δ 1.65 (t, 2H), 2.75 (t, 2H), 3.3 (t, 2H) (Carboni, B.; Benalil, A.; Vaultier, M. *J. Org. Chem.* 1993, 58, 3736-3741).

Synthesis of Linear Peptoid Scaffolds

Peptoid oligomers were synthesized on Rink Amide resin (Novabiochem) (Zuckermann, R. N.; Kerr, J. M.; Kent, S. B. H.; Moos, W. H. *J. Am. Chem. Soc.* 1992, 114, 10646; Holub, J. M.; Garabedian, M. J.; Kirshenbaum, K. *QSAR & Comb. Sci.* 2007, 26, 1175). Resin (100 mg) was swollen in 3 mL of N,N'-dimethylformamide (DMF) for 30 min. and washed twice (3 mL, 20% v/v piperidine/DMF) for 20 min. Multiple washing steps using DMF (4×2 mL) and DCM (3×2 mL) were performed between each synthetic step. Bromoacetic acid (0.167 g/1 mL DMF) and diisopropylcarbodiimide (2 mL/g resin) in DMF were added to the resin and allowed to shake at rt for 20 min (Step A). Following washing, 1.0 mL 3-azido-1-Aminopropane or 2-methoxyethylamine in DMF (10 mL/g resin) was added and the reaction was shaken for 20 min (Step B). Steps A and B were repeated until peptoid oligomers of desired length were obtained.

Synthesis of Cyclic Peptoid Scaffolds

Peptoid oligomers were synthesized on 2-chlorotrityl resin (Novabiochem). Resin (100 mg) was swollen in 3 mL of dichloromethane (DCM) for 5 min. and washed twice (3 mL DCM) for 1 min. Bromoacetic acid (90.3 mg), 107 μL N,N-Diisopropylethylamine (DIPEA) and 1 mL DCM) were added for 40 min. Washing steps using DCM (3×2 mL) and DMF (4×2 mL) were performed and step B was implemented (see linear peptoid synthesis above). Steps A and B were then repeated until peptoid oligomers of desired length were obtained. The 2-chlorotrityl resin was cleaved with hexafluoroisopropanol in $CH_2Cl_2$ and linear precursor was then cyclized with PyBOP/DIPEA/DMF (Shin, S. B. Y.; Yoo, B.; Todaro, L. J.; Kirshenbaum, K. *J. Am. Chem. Soc.* 2007, 129, 3218).

Synthesis of Linear Multivalent Conjugates

Peptoid scaffolds were taken up in 20 mL 2-butanol/DMF/pyridine (5:3:2 by vol.) and reacted with ethisterone (0.75 g), CuI (0.80 g), ascorbic acid (0.30 g), and DIPEA (0.75 g) in a 50 mL conical vial. The vial was sealed and vigorously shaken at 45° C. for 18 h. The resin was washed with DMF (7×3 mL), Cu scavenger cocktail (DMF/pyridine 6:5 v/v, ascorbic acid 0.02 g/mL) (7×3 mL) and DCM (7×3 mL). The resin was cleaved from solid support with a 95% TFA/$H_2O$ solution and characterized by ESI-MS. The crude material was purified using RP-HPLC on a $C_{18}$ preparatory column (Peeke). HPLC chromatograms were monitored at 230 nm using a System Gold 166 detector. Linear gradients were conducted from 5 to 95% solvent B (0.1% TFA in HPLC grade acetonitrile) over solvent A (0.1% TFA in HPLC grade water) in 50 min with a flow rate of 5.0 mL/min. All conjugates were purified to >95% by RP-HPLC. Collected fractions were combined, frozen and lyophilized overnight.

Synthesis of Cyclic Multivalent Conjugates

Peptoid scaffolds were taken up in DMF (12 mL) and reacted with ethisterone (0.75 g), CuI (0.20 g), ascorbic acid (0.28 g), and DIPEA (0.75 g) in a 15 mL conical vial. The vial was sealed and vigorously shaken at room temperature for 18 h. The reaction was concentrated, dissolved in 50% ACN/$H_2O$ and centrifuged. Crude samples were transferred to conical vials, frozen and lyophilized overnight. The crude materials were purified to >95% using RP-HPLC as described above.

Scheme 2: Synthesis of Peptoid oligomers of the Invention

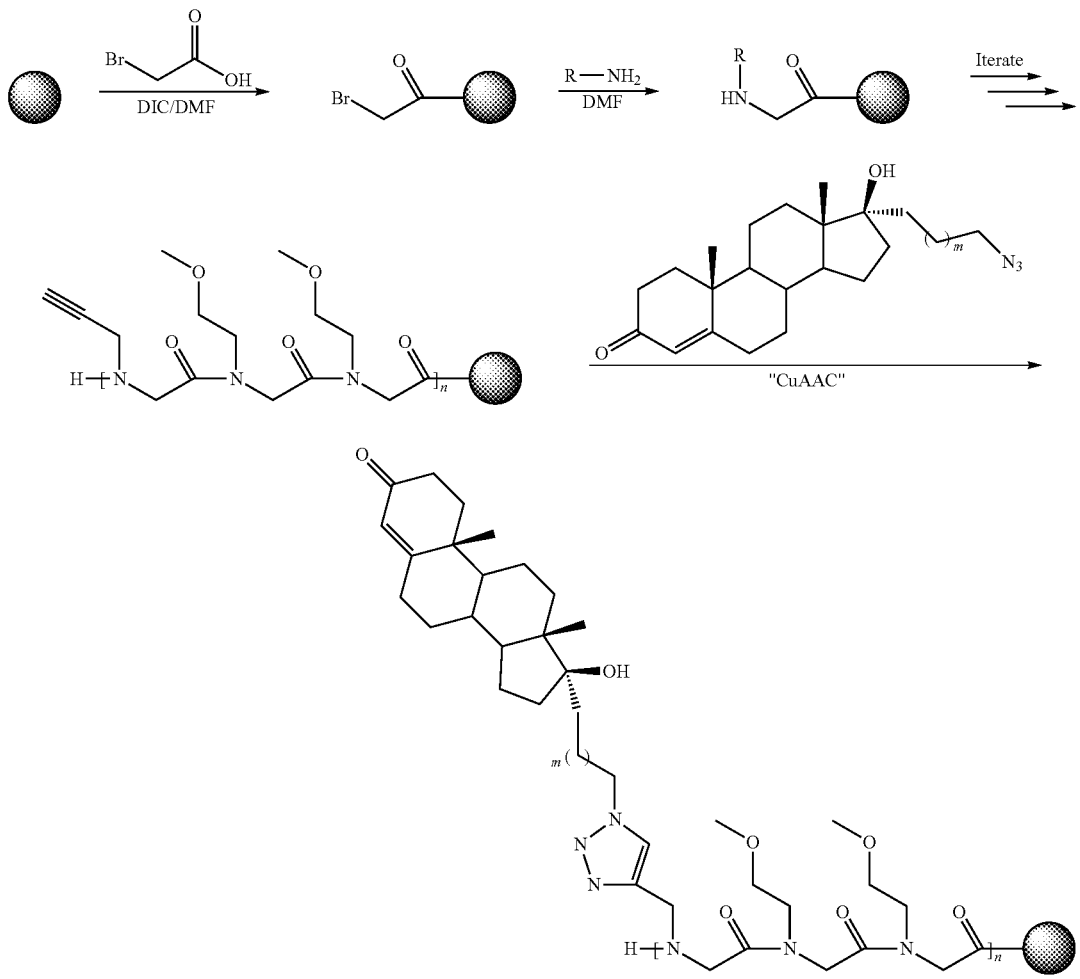

for the purpose of Scheme 2, the subscript m is an integer between 1-8; and the subscript n is 1-15.

The following oligomers are prepared following the method described herein.

TABLE 1

Representative Synthetic Oligomers of the Invention

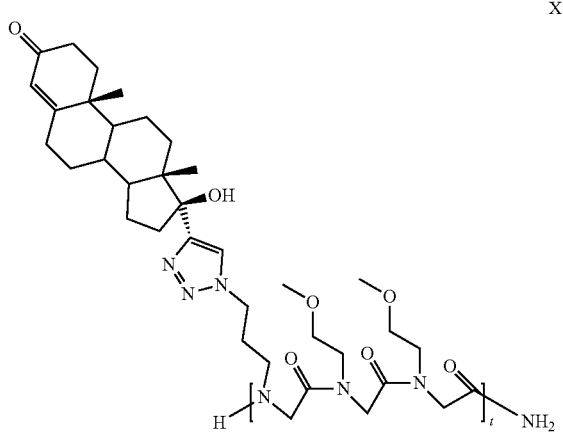

XI

TABLE 1-continued

| # | Oligomer | Calc. m/z | Obs. m/z [M + H] |
|---|---|---|---|
| 1 | t = 1 | 699.4 | 700.4 |
| 2 | t = 2 | 1,381.8 | 1,382.9 |
| 3 | t = 3 | 2,064.4 | 2,065.7 |
| 4 | t = 6 | 4,110.6 | 4,111.6 |
| 4a | t = 4 | 2749.1 | |
| 4b | t = 5 | 3431.5 | |
| 4c | t = 7 | 4797.16 | |
| 4d | t = 8 | 5480.03 | |
| 4e | t = 9 | 6162.8 | |
| 4f | t = 10 | 6845.7 | |

TABLE 2

Representative Synthetic Oligomers of the Invention

XII

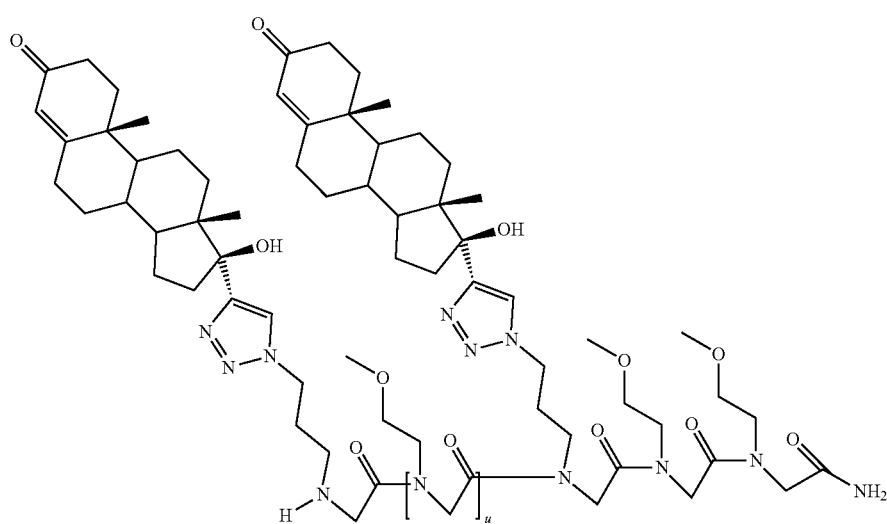

| # | Oligomer | Calc. m/z | Obs. m/z [M + H] |
|---|---|---|---|
| 5 | u = 6 | 1,727.6 | 1,728.8 |
| 6 | u = 8 | 2,072.2 | 2,073.1 |
| 6a | u = 5 | 1612.47 | |
| 6b | u = 4 | 1497.34 | |
| 6c | u = 3 | 1382.21 | |
| 6c | u = 1 | 1151.95 | |

TABLE 3

Representative Synthetic Oligomers of the Invention

XIII

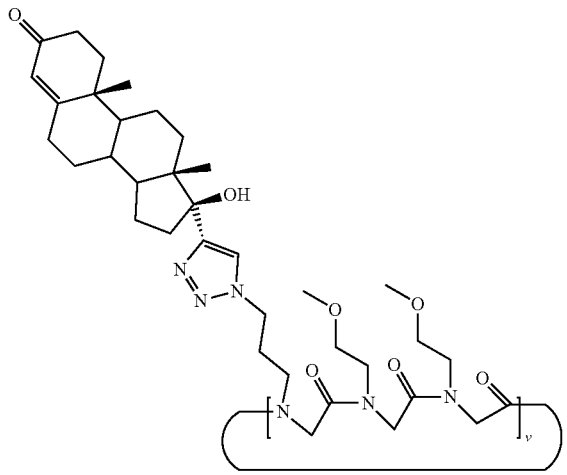

| # | Oligomer | Calc. m/z | Obs. m/z [M + H] |
|---|---|---|---|
| 7 | v = 2 | 1,364.8 | 1,365.8 |
| 7a | v = 3 | 2047.2 | |
| 7b | v = 4 | 2729.6 | |
| 7c | v = 5 | 3412.0 | |
| 7d | v = 6 | 4094.4 | |
| 7e | v = 7 | 4776.8 | |
| 7f | v = 8 | 5459.2 | |

TABLE 4

Representative Synthetic Oligomers of the Invention

XIV

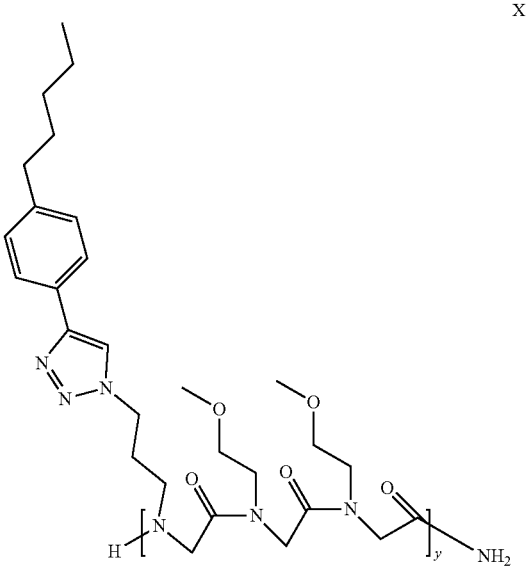

| # | Oligomer | Calc. m/z | Obs. m/z [M + H] |
|---|---|---|---|
| 8 | y = 3 | 1,643.9 | 1,644.8 |
| 8a | y = 4 | 2186.2 | |
| 8b | y = 5 | 2128.5 | |
| 8c | y = 6 | 3270.8 | |
| 8d | y = 7 | 3813.1 | |
| 8e | y = 8 | 4355.4 | |

EXAMPLES

The following examples are presented in order to more fully illustrate the preferred embodiments of the invention. They should in no way be construed, however, as limiting the broad scope of the invention.

Example 1

In Vitro Ligand-Binding Studies
Competitive AR Binding Assay:

Competitive binding of multivalent conjugates for AR was evaluated using the PolarScreen AR fluorescence polarization assay (Invitrogen) according to the manufacturer's instructions. Final concentration of AR-ligand complex was 50 nM. Dilutions of each conjugate were plated in triplicate on a 96-well plate (Greiner) and allowed to compete for approximately four hours before fluorescence polarization was quantified using a microplate reader (Beckman Coulter DTX 880). All data were processed using GraphPad Prism.

Cell Culture:

All cell lines were maintained at 5% $CO_2$ in a 37° C. incubator and cultured in appropriate media (refer to assay for conditions). Typically, cells were grown on 10 cm tissue-culture dishes (BD Falcon) to approximately 80% confluence before subculture.

Figure 2:
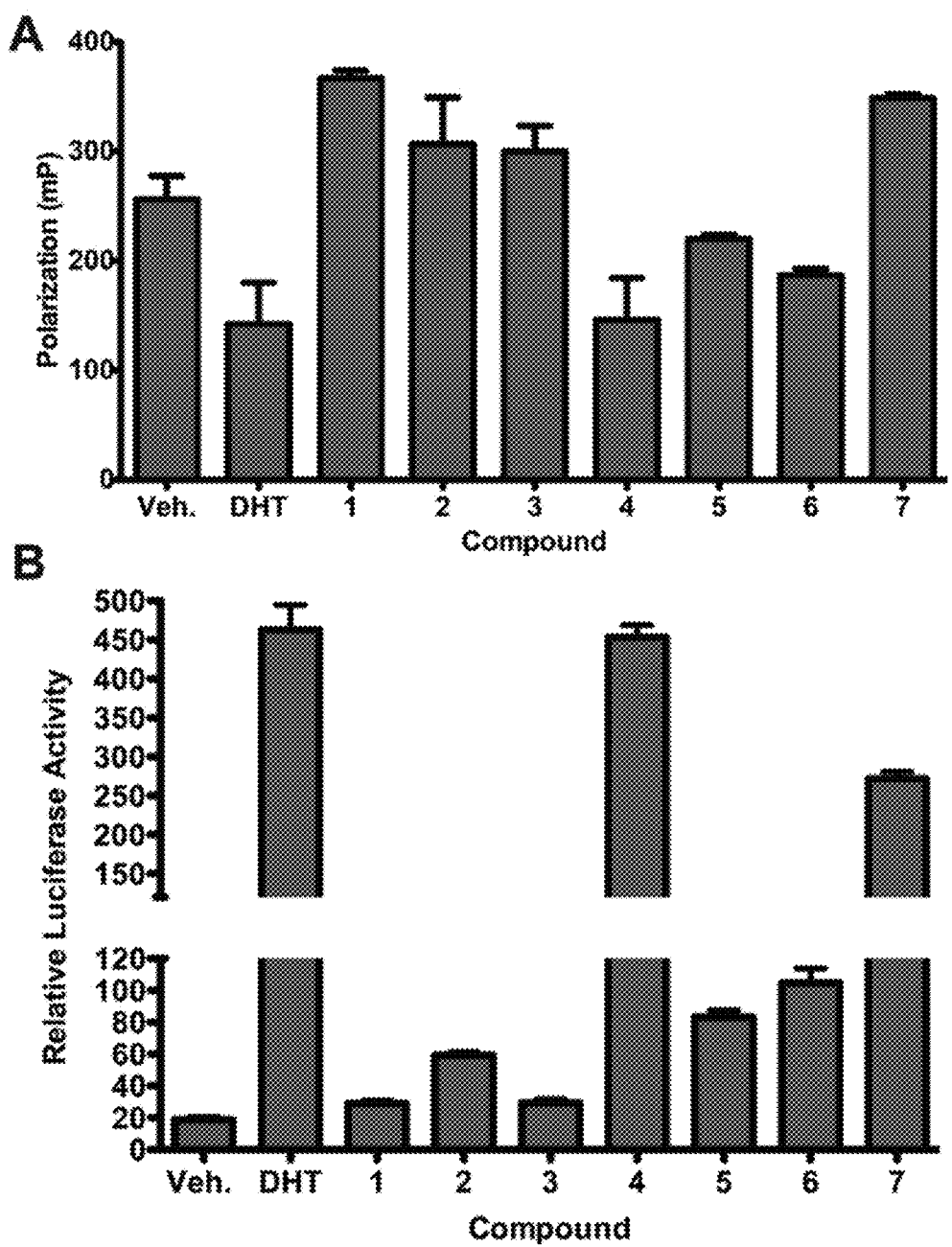
Figure 4:
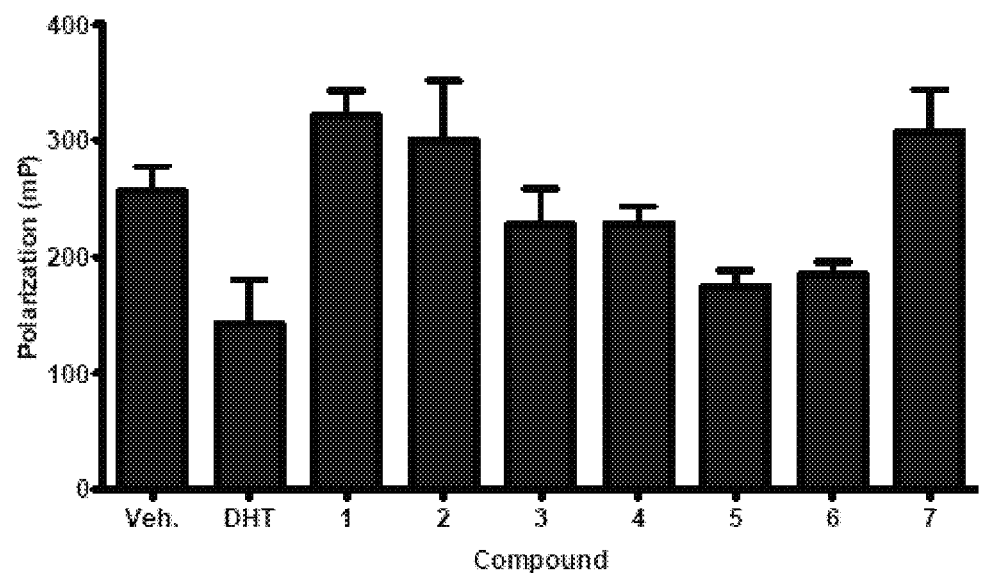

An in vitro ligand-binding assay was used to evaluate binding of the multivalent peptoid oligomers to the AR. In this assay, competitive binding was detected by a change in fluorescence polarization that occurs upon displacement of a fluorescently-labeled hormone ligand from AR by a competitive ligand (Kolev, M. V.; Ruseva, M. M.; Morgan, B. P.; Donev, R. M. J. Immunol. Res. 2010, 184, 6035). Oligomers 1, 2, 3 and 7 do not compete against DHT for binding at concentrations up to 10 µM (FIG. 2A and FIG. 4). Oligomers 4-6 compete for binding, indicated by a decrease in fluorescence polarization relative to vehicle treatment. Increasing the valency and spacing of the ethisterone moieties along the peptoid backbone enhances AR binding.[30]

To determine if the oligomers function as AR agonists, the ability of the oligomers to induce AR-mediated transcriptional activation in LNCaP cells was evaluated. For this study, a LNCaP cell line that stably expresses the AR-responsive luciferase reporter gene under the probasin promoter was used.[31] These cells, termed LB1, were treated with oligomers 1-7 at a concentration of 1 µM for 24 hours, and AR-mediated transcriptional activation was measured (FIG. 2B). As a positive control for full AR-mediated transcriptional activation, cells were also treated with DHT. Compared to DHT, which resulted in a 23.5-fold induction of the reporter gene over baseline, oligomers 1, 2 and 3 were weak activators of AR, displaying only a 1.5- to 3-fold induction of the reporter gene. In contrast, hexavalent oligomer 4 produced a robust induction of the reporter gene to levels similar to DHT. Divalent oligomer 6 showed greater reporter gene induction as compared to 5 (6-fold vs. 4.5-fold). This is consistent with the competitive AR binding data observed for oligomers 1-6. Oligomer 7 displayed a strong 11-fold induction of reporter gene activity despite its inability to compete with DHT for binding to the AR. These results indicate that different multivalent oligomers can operate through either competitive or non-competitive mechanisms to regulate AR-mediated transcriptional activation.

Figure 3:
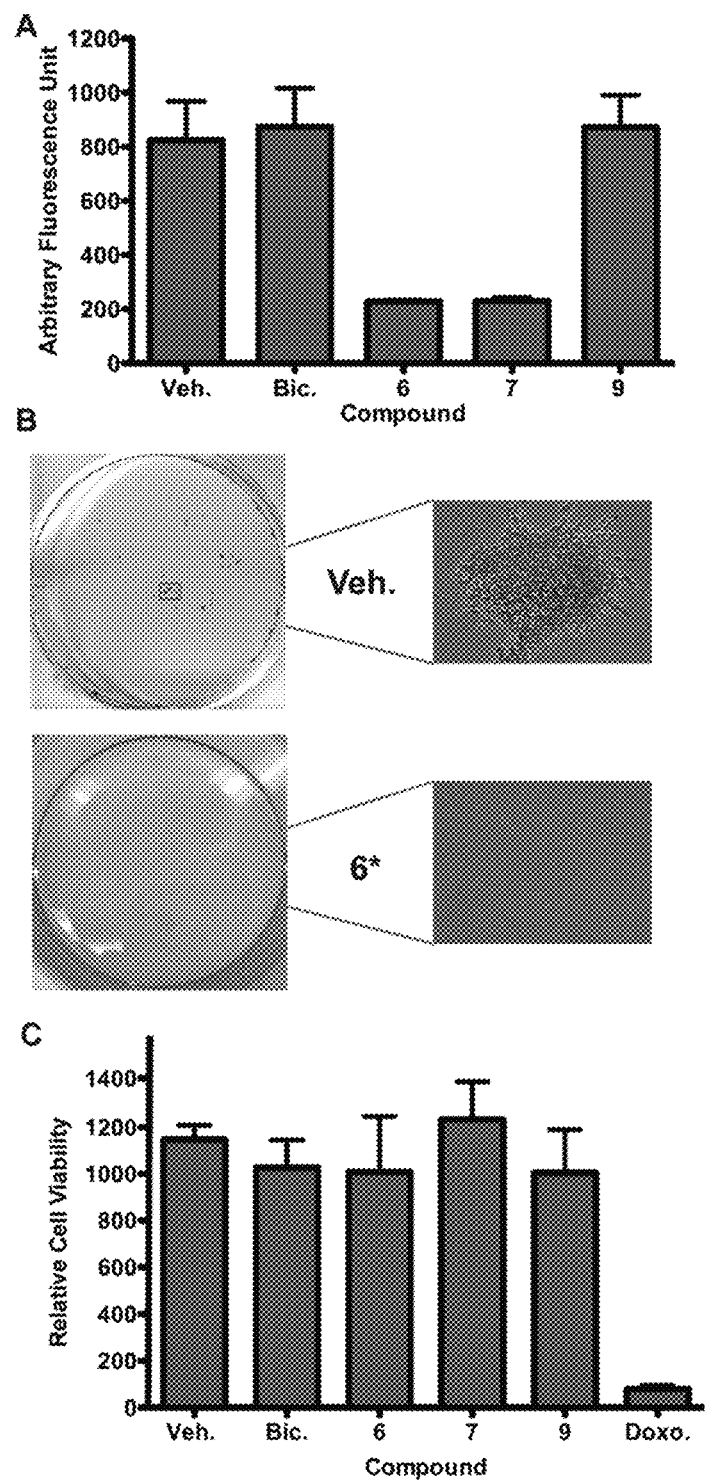
Figure 5:
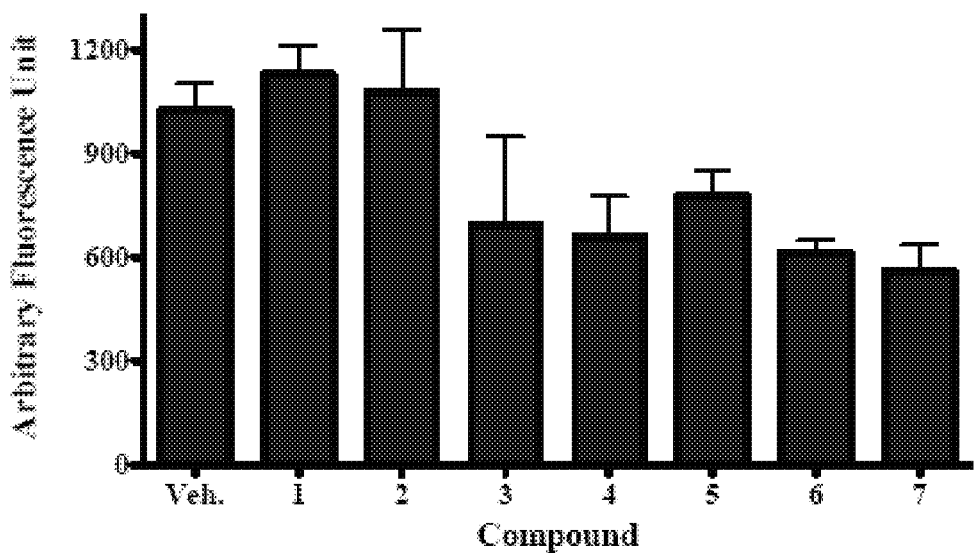
Figure 6:
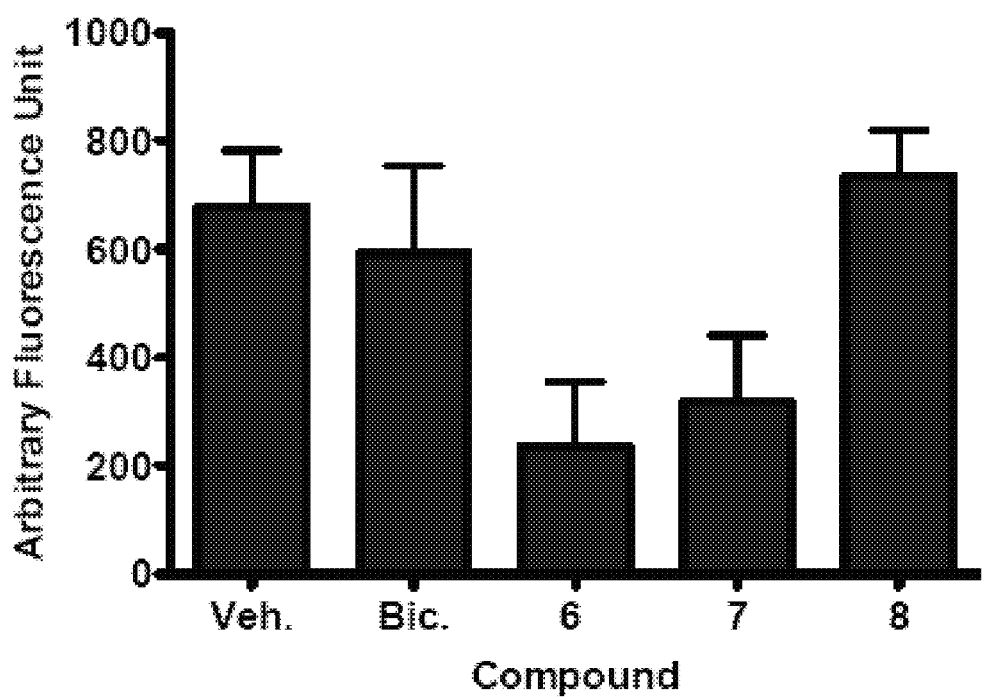

The inventors next evaluated if oligomers 1-7 were able to suppress the proliferation of LNCaP-abl cells. These cells are models of advanced disease that express AR, and proliferate in the absence of hormone. LNCaP-abl cells were treated with oligomers 1-7 for 72 hours, and cellular proliferation was measured utilizing the CyQUANT assay (FIG. 5).[32]. Oligomers 1 and 2, which fail to competitively bind AR or activate AR gene expression, had little impact on the proliferation of the LNCaP-abl cells. In contrast, oligomer 3, which elicited only a 3-fold induction of AR reporter gene activity, suppressed the proliferation of the LNCaP-abl cells. This suggests that oligomer 3 is likely functioning as an AR antagonist. Oligomer 4, which induced a potent AR transcriptional response, inhibited cell proliferation to the same extent as oligomer 3. Oligomers 6 and 7 displayed the greatest levels of inhibition of cell proliferation. Although oligomers 3-7 suppress the proliferation of LNCaP-abl cells, they do so through different mechanisms, given the distinctive profiles for competitive binding elicited by the oligomers. Oligomers 6 and 7 were further evaluated for their ability to inhibit LNCaP-abl cell proliferation. At concentrations of 1 µM or 10 nM, oligomers 6 and 7 evoke a potent reduction in cell proliferation, relative to vehicle treatment (FIG. 3A and FIG. 6). To demonstrate that suppression of proliferation can be specifically attributed to the presence of the steroid ligands, an additional trivalent control compound (oligomer 8) was synthesized. Oligomer 8, lacking the ethisterone moieties, had no effect on cell proliferation. The standard AR monotherapy bicalutamide also had no effect on cell proliferation. In addition, LNCaP-abl cells were treated with oligomers 6 and 7 at a concentration of 1 µM for 14 days, and stained with crystal violet to detect differences on long-term proliferation and colony-formation. Oligomers 6 and 7 inhibited the number and size of colonies formed relative to vehicle treatment (FIG. 3B). These results highlight the potential biomedical significance of multivalent peptoid oligomers for advanced prostate cancer.

To evaluate the general cell toxicity of oligomers 6 and 7, a cell viability assay was utilized. Oligomers 6 and 7 did not exhibit cytotoxic effects in human embryonic kidney (HEK293) cells or AR-deficient prostate cancer (PC3) cells (FIG. 3C). These results suggest that oligomers 6 and 7 are selectively active and exert anti-proliferative activity in LNCaP-abl cells.

Additionally, as disclosed in inventors' own publication [Kirshenbaum, K. (2012) Androgen Receptor Antagonism by Divalent Ethisterone Conjugates in Castrate-Resistant Prostate Cancer Cells. *ACS Chem. Biol.* 7: 1693-1701, incorporated herein by reference], initial screening of oligomers 6 and 7 revealed that they modulate AR activity through competitive and non-competitive mechanisms, respectively. Moreover, oligomers 6 and 7 displayed anti-proliferative activity in LNCaP-abl cells, a cell culture model of castrate-resistant prostate cancer that proliferates in low hormone conditions. The oligomers exhibited potent anti-proliferative effects at a concentration of 1 µM. Importantly, cytotoxicity was not observed in non-AR expressing human embryonic kidney (HEK293) cells or AR deficient prostate cancer (PC3) cells, suggesting oligomers 6 and 7 selectively target the AR in LNCaP-abl cells. These results highlighted the potential biomedical significance of multivalent peptoid conjugates for castrate-resistant prostate cancer.

The peptoid-based oligomers described herein represent the first multivalent constructs designed to specifically target the AR. The oligomeric scaffold provides a versatile platform that can be utilized to modulate AR activity. This study demonstrates that multivalent ethisterone oligomers can compete for AR binding and modulate AR-mediated transcription. A linear and a cyclic oligomer exhibit potent anti-proliferative activity in therapy-resistant prostate cancer cells through competitive and non-competitive mechanisms, respectively. Cytotoxicity was not observed in non-AR expressing HEK293 or PC3 cells. Recent evidence suggests that bivalent ligands tethered by flexible linkers are capable of bridging the hormone binding pockets of steroid hormone receptors. Future studies will evaluate the mechanism of action of these compounds, and explore their potential applications in AR pharmacology and chemical biology.

AR-Mediated Transcription Assay:

LB1 cells were seeded in triplicate on 24-well plates (Corning) at a density of approximately $7.5 \times 10^4$ cells/well in RPMI media supplemented with 10% fetal bovine serum (FBS), 1% L-Glutamine (L-Gln) and 1% Penicillin/Streptomycin (PS). Following attachment, cells were starved with RPMI media for 48 hours supplemented with 10% charcoal-stripped FBS, treated with conjugates to a final concentration of 1 µM and incubated at 37° C. for 24 hours. Following incubation, cells were washed with PBS and lysed in 1× luciferase cell culture lysis reagent (Promega) according to the manufacturer's instructions. Luciferase activity was quantified in a reaction mixture containing 10 µL cell lysate and 50 µL luciferase assay reagent (Promega) using a microplate luminometer (LMax). Data were normalized to protein concentration quantified by a standard colorimetric Bradford assay (Bio-Rad). All data were processed using GraphPad Prism.

Cell Proliferation Assay:

LNCaP-abl cells were seeded in triplicate on 96-well plates (Corning) at a density of $5.0 \times 10^3$ cells/well in RPMI media supplemented with 10% charcoal-stripped FBS, 1% L-Gln and 1% PS. Following attachment, cells were treated with conjugates and allowed to incubate at 37° C. for 72 hours. Following treatment, cells were centrifuged (2,000 rpm) for 2 min. and treated with the CyQUANT reagent (Invitrogen) according to the manufacturer's instructions. CyQUANT binds DNA and is a surrogate measure for cell proliferation. Fluorescence activity was quantified using a microplate reader (Molecular Devices) and SoftMax Pro® software. All data were processed using GraphPad Prism.

Colony Forming Assay:

LNCaP-abl cells were seeded on 6-well plates (Corning) at a density of $2.0 \times 10^3$ cells/well in RPMI media supplemented with 10% charcoal-stripped FBS, 1% L-Gln and 1% PS. Following attachment, cells were treated to a final concentration of 1 µM and allowed to incubate at 37° C. for 13-17 days. Media was changed every 3-4 days. Following treatment, cells were fixed with methanol and stained with crystal violet (Sigma) for visual detection. Cell colony images were acquired on a TE2000-U inverted microscope (Nikon Instruments Inc.) using a Sony Cool Snap ES camera controlled by MetaMorph software.

Cell Toxicity Assay:

HEK293 and PC3 cells were seeded in triplicate on 96-well plates (Corning) in DMEM and HAM'S—F media supplemented with 10% FBS, 1% L-Gln and 1% PS, respectively. HEK293 and PC3 cells were then treated with conjugates (1 µM and 20 µM, respectively) and allowed to incubate at 37° C. for 72 hours. Following treatment, relative cell viability was measured using the CyQUANT reagent according to the manufacturer's instructions. Fluorescence intensity was quantified as described above. All data were processed using GraphPad Prism.

Example 2

Time Resolved Fluorescence Resonance Energy Transfer

LanthaScreen TR-FRET Androgen Receptor Co-activator Assay (Invitrogen) was used according to the manufacturer's instructions. Assay samples were prepared in triplicate on 384-well plates (Corning no. 3676) as recommended by the manufacturer and incubated at 25° C. for 2 h before data collection. The fluorescence emission values at 520 and 495 nm, evaluated using excitation at 340 nm, were obtained using a SpectraMax M5 plate reader (Molecular Devices) and SoftMax Pro software. All data were processed using GraphPad Prism.

Cell Culture.

All cell lines were maintained at 5% CO2 in a 37° C. incubator and cultured in appropriate media (refer to assay for conditions). Typically, cells were grown on 10 cm tissue-culture dishes (BD Falcon) to approximately 80% confluence before subculture.

Protein Expression.

LNCaP-abl cells were grown on 10 cm culture dishes (BD Falcon) in RPMI media supplemented with 10% fetal bovine serum (FBS), 1% L-glutamine (L-Gln) and 1% penicillin/streptomycin (PS). Cells were treated with conjugate 1 or 2 to a final concentration of 1 μM and allowed to incubate at 37° C. for 48-72 h. Following treatment, cells were harvested in PBS buffer, centrifuged and lysed with RIPA buffer (10 mM Tris (pH 8.0), 1 mM EDTA (pH 8.0), 140 mM NaCl, 5% glycerol, 0.1% Deoxycholate, 0.1% SDS, and 1% Triton X-100) containing 1 mM Na3VO4 and 1× protease inhibitor to obtain cellular extracts. Protein concentration was quantified by a standard colorimetric Bradford assay (Bio-Rad), and samples were subjected to SDS-PAGE (25 μg protein well-1). The separated proteins were then transferred onto Immobilon membranes (Millipore) and probed with anti-AR (441, Santa Cruz Biotechnology) or anti-tubulin (Covance) primary antibodies followed by horseradish peroxidase-conjugated goat anti-mouse or anti-rabbit IgG secondary antibodies.

Cellular Localization.

HEK293 cells were seeded on pretreated (poly-D-lysine) 8-well chamber slides (Nunc) at a density of 3.0×10$^4$ cells well-1 in DMEM media supplemented with 10% FBS, 1% L-Gln, and 1% PS. Following attachment, cells were transfected with an AR fluorescent protein hybrid (kind gift of Jeremy Jones, City of Hope, Calif.) and starved in DMEM media supplemented with 10% charcoal stripped FBS for 72 h. Following starvation, cells were treated with peptoid conjugate 1 or 2 (1 μM) or DHT (1 nM) and allowed to incubate at 37° C. for 4 h. Cells were fixed for 20 min in PBS containing 4% formaldehyde and stained with DAPI mounting solution. Images were analyzed and acquired using a Leica TCS SP5 II Confocal Microscope.

Chromatin Immunoprecipitation.

LNCaP-abl cells were grown on 10 cm culture dishes (BD Falcon) to approximately 70% confluence in RPMI media supplemented with 10% charcoal-stripped FBS, 1% L-Gln, and 1% PS. Following attachment, cells were treated with conjugates 1 or 2 (1 μM) plus R-1881 (10 nM) and allowed to incubate at 37° C. for 4 or 16 h. Following treatment, proteins were double cross-linked with DSP (Pierce) for 20 min and 1% formalin for 10 min. Cells were lysed, and nuclei were collected, lysed in buffer (1% SDS, 50 mM Tris-HCl (pH 8.0), 10 mM EDTA), and sonicated for 12 min (30 s on, 30 s off) utilizing a Bioruptor sonicator (Diagenode, model XL). Sonicated lysates were precleared for 2 h with Protein A/G agarose beads blocked with salmon sperm DNA (Millipore). Supernatants were then incubated overnight with a mixture of antibodies to AR (2 μg AR-441 and 2 μg AR-N20, Santa Cruz Biotechnology). Control ChIP was concurrently performed with the same quantity of normal mouse and rabbit IgG sera. Immunocomplexes were then washed and cross-linking was reversed. DNA was isolated with a PCR purification kit (Qiagen) according to the manufacturer's instructions, and real-time PCR was performed. Relative enrichment of indicated genomic locus was calculated as a percentage of 4% input normalized to IgG. All data were processed using GraphPad Prism.

Flow Cytometry.

LNCaP-abl cells were grown on 10 cm culture dishes (BD Falcon) to approximately 70% confluence in RPMI media supplemented with 10% charcoal-stripped FBS, 1% L-Gln, and 1% PS. Cells were then treated with conjugate 1 or 2 to a final concentration of 1 μM and allowed to incubate at 37° C. for 48 h. Following treatment, cells were fixed and suspended in 2 mL of 1:3 HBSS:Phosphate-Citrate Buffer (pH 8.0) containing 0.1% Triton X-100. Cells were centrifuged (2,000 rpm for 5 min) and suspended in 1 mL of propidium-iodide solution (1 mg propidium iodine, 10 mg EDTA, 250 μL Igepal, and 2.2 μg μL-1 RNAase in 50 mL of PBS). Cells were then harvested for cell-cycle analysis by filtration (CellTrics, 100 μm) into conical tubes (Falcon) and analyzed by flow cytometry (Becton-Dickinson FACScalibur). All data were analyzed using FlowJo software.

AR Target Gene Expression.

LNCaP-abl cells were grown on 6 cm culture dishes (BD Falcon) at a density of approximately 1.0×10$^6$ cells well-1 in charcoal-stripped RPMI supplemented with 10% FBS, 1% L-Glu, and 1% PS. Cells were then treated with conjugate 1 or 2 to a final concentration of 10 μM and allowed to incubate at 37° C. for 24 h. Following treatment, cells were harvested, and RNA was extracted utilizing the RNeasy mini kit (Qiagen) according to the manufacturer's instructions. RNA concentration was quantified by UV absorbance via NanoDrop (Thermo-Scientific). Complementary DNA was then prepared by PCR (MJ Research PTC-200 Thermo Cycler) and relative mRNA levels for G2/M-phase cell-cycle regulatory genes were determined by real-time PCR (Bio-Rad MyiQ) using the SYBR Green PCR kit (Applied Biosystems) according to the manufacturer's instructions. All data were processed using GraphPad Prism.

Microarray Analysis.

LNCaP-abl cells were grown on 10 cm culture dishes (BD Falcon) to approximately 70% confluence in RPMI media supplemented with 10% charcoal-stripped FBS, 1% L-Gln, and 1% PS. Cells were then treated with conjugate 1 or 2 to a final concentration of 1 μM and allowed to incubate at 37° C. for 24 h. Following treatment, cells were harvested, and RNA was extracted and quantified as described above. The final RNA concentration for each sample was >1 μg μL-1. Microarray experiments were carried out at the Memorial Sloan-Kettering Cancer Center Genomics Core Facility using Affymetrix Human Genome U133 plus 2.0 expression arrays. Normalization of the raw data was conducted using R BioConductor and the "affy" data processing package (Gautier et al, Bioinformatics, 2004, 20, 307-315; Gentleman et al, Bioconductor: Open Software Development for Computational Biology and Bioinformatics. Genome Biol. 2004, 5, R80).

Effect on AR Protein Expression and Cellular Localization.

Figure 7:
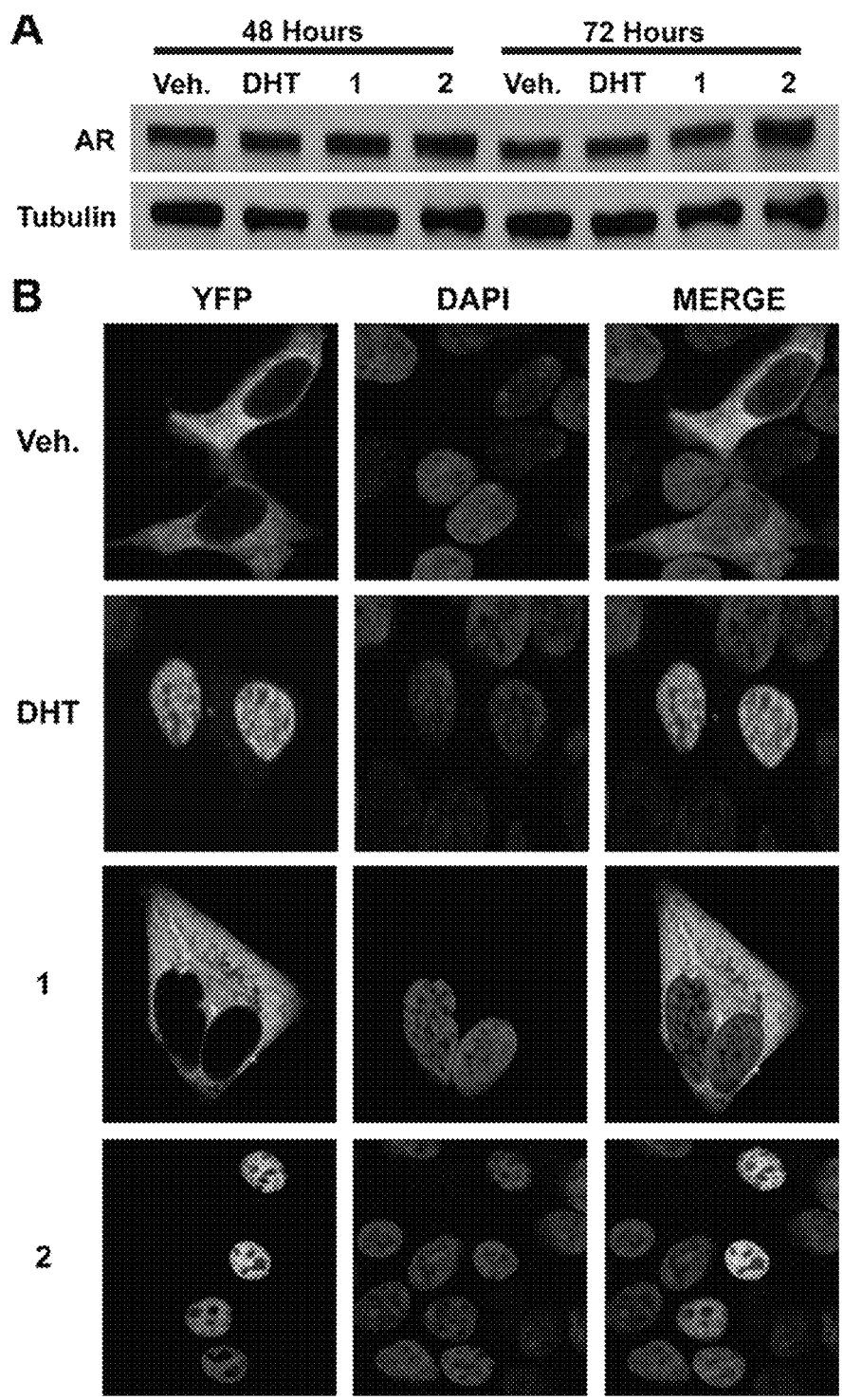
In FIGS. 7-15, compound 1 refers to Oligomer #6 (Table 2); and compound 2 refers to Oligomer #7 (Table 3).

The inventors first evaluated if oligomer 6 or 7 can induce AR degradation within the cell, as previous studies of AR antagonists have reported the induction of receptor degradation in vivo.[34] Cellular extracts of LNCaP-abl cells treated with either oligomer 6 or 7 were prepared and immunoblotted for AR (FIG. 7A, 1 is Oligomer 6 and 2 is Oligomer 7). Oligomers 6 and 7 exhibited no significant effect on AR protein levels, relative to control treatments. Thus, oligomers 6 and 7 do not induce AR degradation. To explore the cellular localization of AR in the presence and absence of oligomers 6 or 7, confocal microscopy was conducted utilizing an AR fluorescent protein hybrid (FIG. 7B, 1 is Oligomer 6 and 2 is Oligomer 7).[35] In the absence of native ligand, AR was diffusely distributed in the cytoplasm. Upon treatment with DHT, AR accumulates in the nucleus as expected. Unlike DHT, oligomer 6 does not promote AR nuclear localization. Interestingly, and in contrast to oligomer 6, oligomer 7 evokes AR nuclear localization. This suggests oligomers 6 and 7 are eliciting distinct modes of AR antagonism.

Modulation of AR Nuclear Function.

Figure 8:
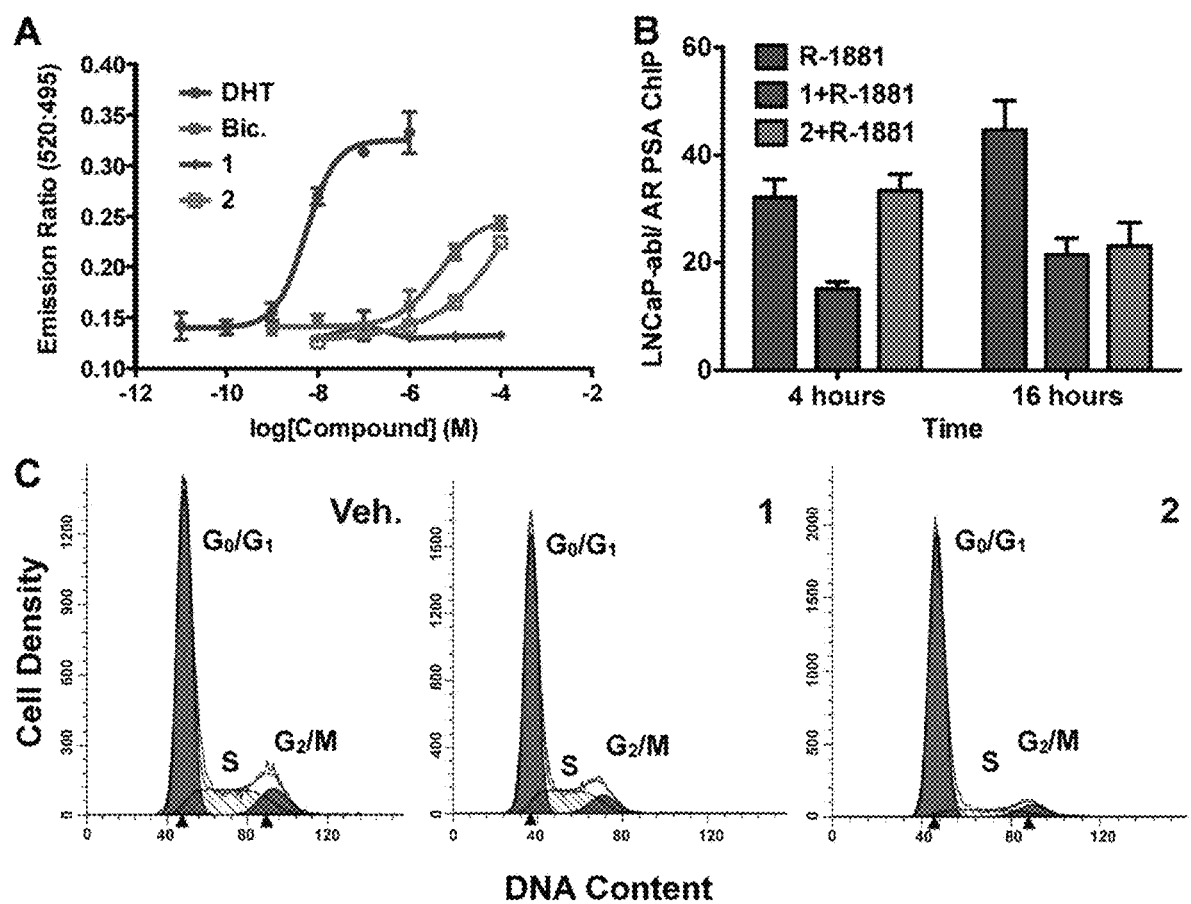
Figure 11:
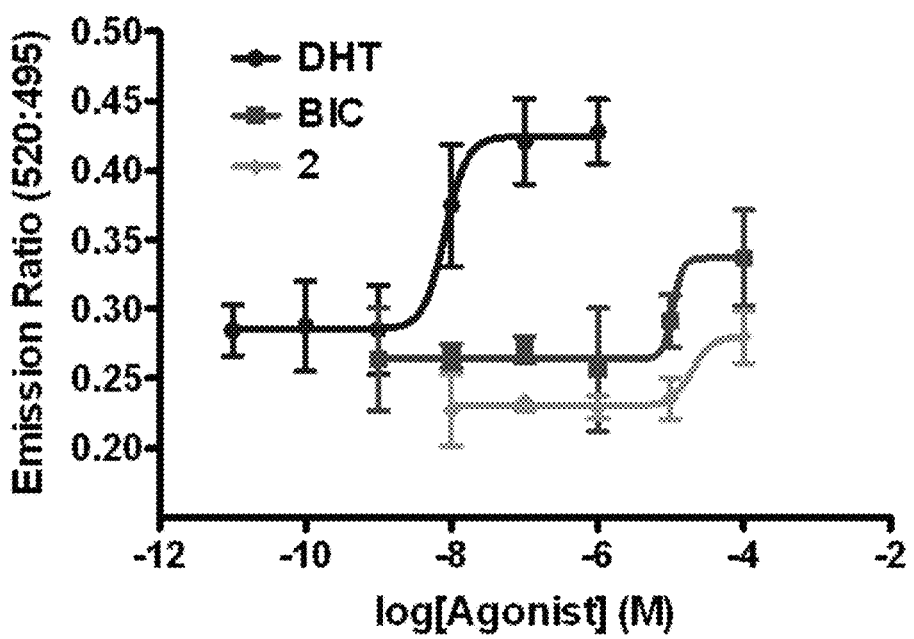

An in vitro time resolved fluorescence resonance energy transfer (TR-FRET) assay was utilized to determine if oligomers 6 or 7 promote binding between AR and co-activator proteins. In this assay, the interaction between GST-tagged AR-LBD and a FxxLF co-activator peptide (VESGSSRFMQLFMANDLLT) is monitored in the presence of ligand by a TR-FRET signal between a terbium-labeled AR-specific anti-GST antibody and a fluorescein-labeled AR FxxLF co-activator peptide.[36] Binding of agonist to the AR-LBD induces a conformational change to helix 12 (a co-activator protein binding site), resulting in the high affinity recruitment of the FxxLF co-activator peptide. Upon excitation, energy is transferred from the terbium-labeled anti-GST antibody to the fluorescein-labeled co-activator peptide, and a TR-FRET signal is detected. In the presence of anti-androgens, helix 12 can adopt a conformation that impairs co-activator peptide binding, resulting in a decrease of the TR-FRET signal. The inventors confirmed that DHT promotes a dose-dependent interaction between AR and the FxxLF motif containing peptide, indicative of high affinity co-activator binding (FIG. 8A, 1 is Oligomer 6 and 2 is Oligomer 7). As expected for an antiandrogen, the standard AR monotherapy bicalutamide partially promotes binding between AR and the co-activator peptide.[37] Oligomer 7 induced a similar dose response to bicalutamide, suggesting partial recruitment of the co-activator peptide (FIG. 8A and FIG. 11; 1 is Oligomer 6 and 2 is Oligomer 7). Oligomer 6 does not promote binding between AR and the fluorescein-labeled co-activator peptide.

Figure 12:
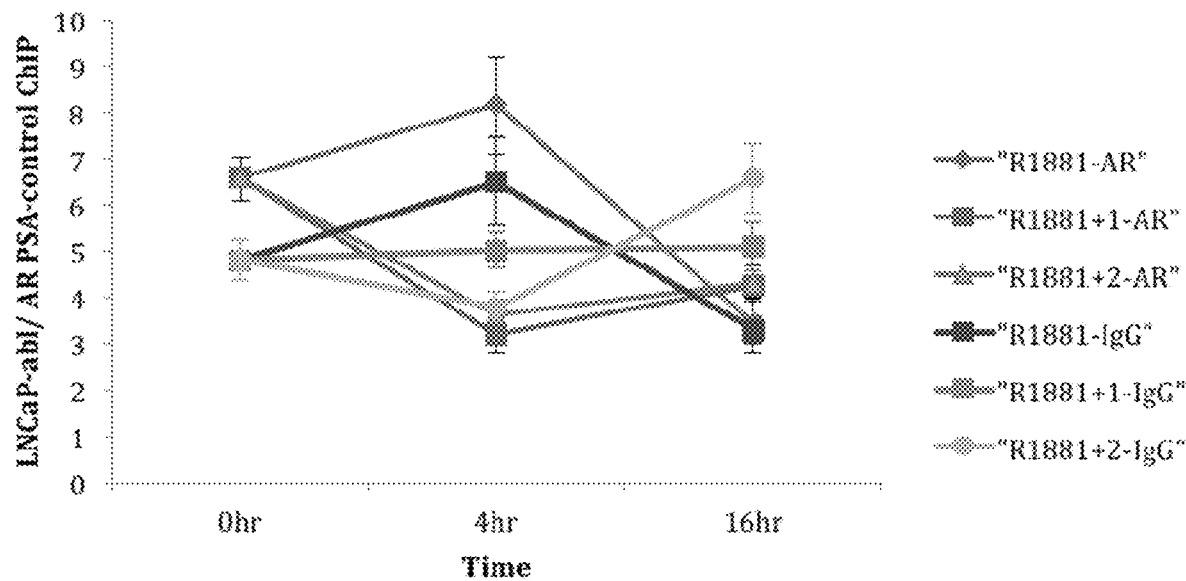

To assess whether oligomers 6 or 7 disrupt binding between AR and DNA, chromatin immunoprecipitation (ChIP) experiments were conducted. In a positive control experiment, the synthetic competitive AR agonist R-1881 promoted AR recruitment to the prostate-specific antigen (PSA) enhancer, a well characterized androgen-regulated gene (FIG. 8B).[56] Upon co-treatment with R-1881 and either oligomer 6 or 7, the occupancy of AR to the PSA enhancer was reduced, indicating that oligomers 6 and 7 inhibit binding between AR and DNA. Oligomer 6 likely inhibits AR recruitment to the PSA enhancer because it does not promote AR nuclear localization or co-activator binding. Oligomer 6 blocked AR recruitment to the PSA enhancer at both 4 and 16 h, whereas this effect was only observed at the 16 h time point for oligomer 7. Oligomer 7 does not compete directly with R-1881 for binding, and thus the time-course of oligomer 7 in the presence of R-1881 may be slow to elicit a biological response. This is consistent with previous studies using ChIP analysis with non-competitive antagonists.18 As expected in control ChIP experiments, specific binding of AR in response to R-1881 is not observed upstream of the PSA enhancer, confirming the specificity of AR binding at the PSA enhancer (FIG. 12, 1 is Oligomer 6 and 2 is Oligomer 7).

Cell-Cycle Distribution.

Figure 13:
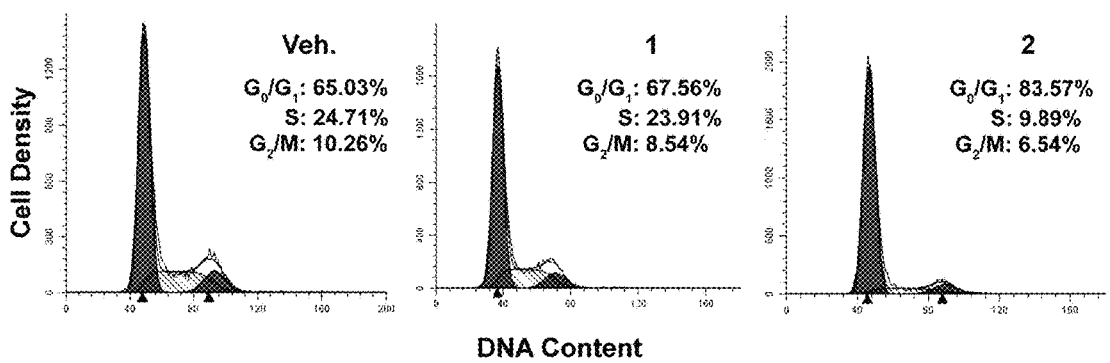

The inventors analyzed cell-cycle distribution of LNCaP-abl cells treated with either oligomer 6 or 7 utilizing fluorescence-activated cell sorting (FACS) analysis. These studies provide a quantitative assessment of normal and apoptotic nuclei along with cell distribution in the G0/G1, S, and G2/M phases of the cell-cycle. Oligomer 6 showed a modest increase in the G0/G1 phase, relative to vehicle treatment (FIG. 8C and FIG. 13, 1 is Oligomer 6 and 2 is Oligomer 7). In contrast, oligomer 7 significantly decreased the cell population in the G2/M and S phases and enhanced the G0/G1 cell population, relative to vehicle treatment. In addition, no increase in the apoptotic cell population was detected for cells treated in the presence of oligomer 6 or 7. These results suggest that oligomer 7 induces cell-cycle arrest in the G0/G1 phase into the S phase transition, while oligomer 6 does not appear to induce growth arrest by influencing a particular stage of the cell cycle in LNCaP-abl cells.

Gene Expression Analysis.

Figure 9:
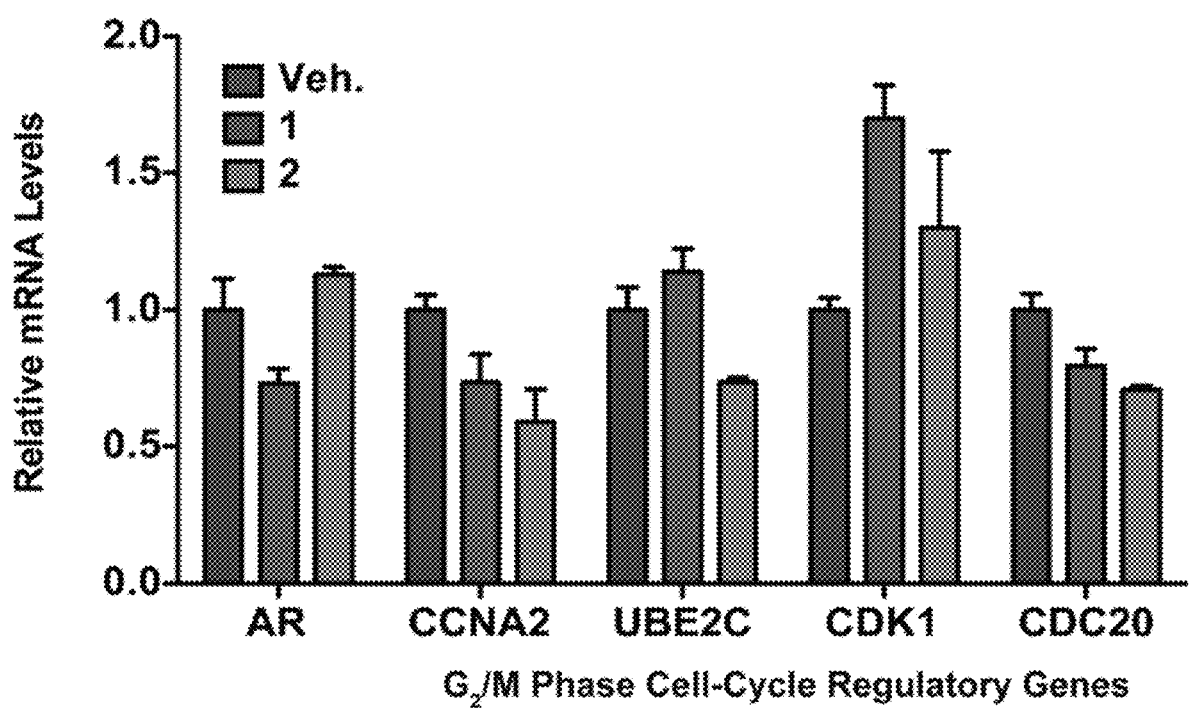

Recently, it has been shown that the AR is responsible for regulating a unique set of target genes in LNCaP-abl cells involved in cell-cycle progression including UBE2C, CCNA2, CKD1 and CDC20.57 In particular, UBE2C has been shown to play a critical role in LNCaP-abl cell proliferation. Therefore, the inventors examined if oligomers 6 and 7 were capable of affecting mRNA expression of these target genes in LNCaP-abl cells utilizing real-time PCR (FIG. 9, 1 is Oligomer 6 and 2 is Oligomer 7). Oligomers 6 and 7 modestly inhibit the expression of CCNA2 and CDC20, but not CDK1. In addition, oligomer 7, but not 1, reduced the expression of UBE2C. These results indicate that oligomers 6 and 7 differentially affect AR target gene expression in LNCaP-abl cells. This likely reflects the distinct mechanisms of AR antagonism exhibited by peptoid oligomers 6 and 7 (vide supra).

Genome-wide expression profiles of LNCaP-abl cells were obtained in the presence and absence of oligomers 6 or 7 and analyzed utilizing gene expression microarrays to identify global effects upon treatment in castrate-resistant prostate cancer cells. Relative to vehicle treatment, oligomer 6 affected 108 transcripts (10 up-regulated and 98 down-regulated) by at least 2-fold (P≤0.05, Table 5).

TABLE 5

Number of Gene Transcripts Affected by Divalent Peptoid Oligomers 6 and 7 Relative to Vehicle Treatment (P ≤ 0.05)

| Oligomer | Up-regulated (fold change ≥ 1.5) | Down-regulated (fold change ≤ −1.5) | Up-regulated (fold change ≥ 2.0) | Down-regulated (fold change ≤ −2.0) |
|---|---|---|---|---|
| 6 | 89 | 247 | 10 | 98 |
| 7 | 998 | 1545 | 386 | 700 |

Figure 10:
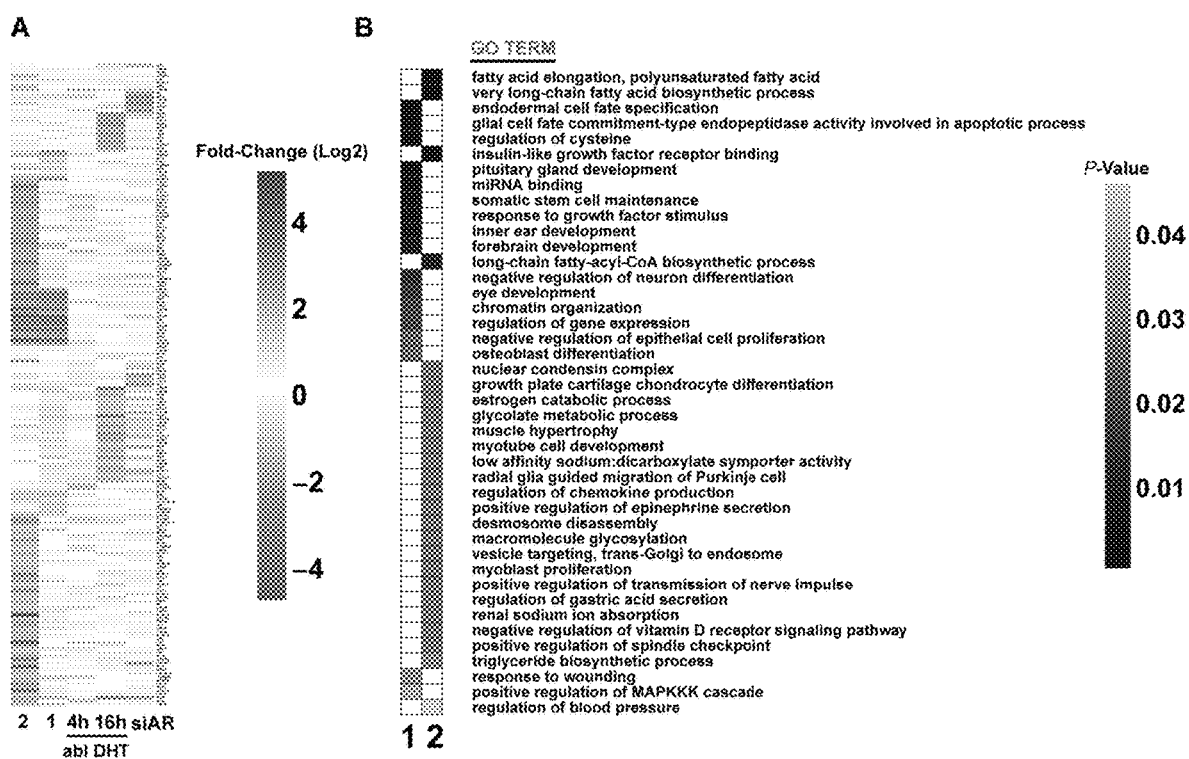
Figure 14:
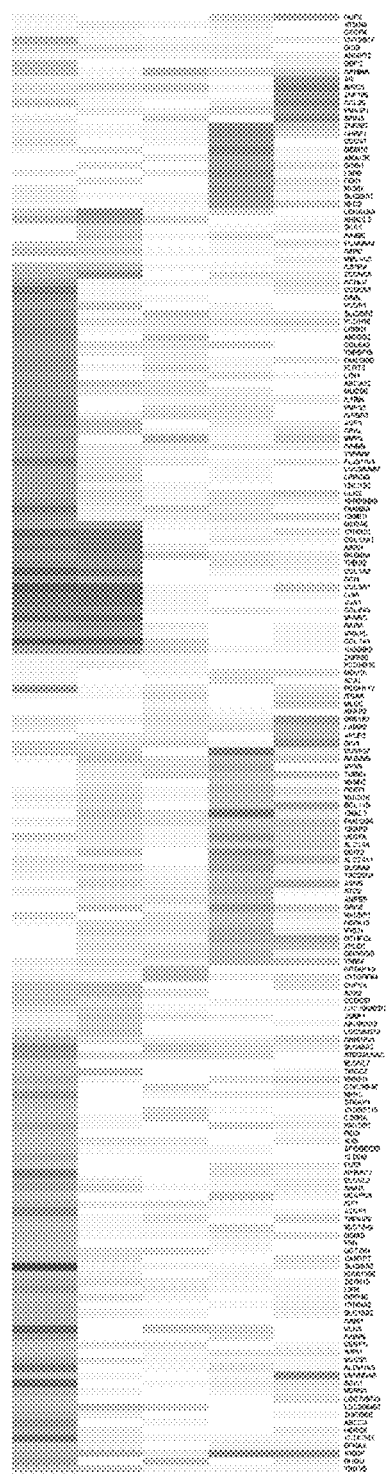

In contrast, a total of 1,086 transcripts (386 up-regulated and 700 down-regulated) were affected upon treatment with oligomer 7, consistent with its ability to promote nuclear localization and co-activator recruitment. In addition, clustering analysis over all of the probed gene transcripts reveals that the expression profiles for LNCaP-abl cells treated with either oligomer 6 or 7 are distinct (FIG. 10A and FIG. 14, 1 is Oligomer 6 and 2 is Oligomer 7). Studies have shown that AR antagonists can alter the expression of androgen induced genes, such as FKBP5, KLK3 (PSA), and AMIGO2.5,[38] In the presence of either oligomer 6 or 7, the inventors observe variations in expression of these genes. In comparing expression profiles of LNCaP-abl cells activated with hormone (DHT) or in a basal AR activity state (siAR), oligomers 6 and 7 can be clearly distinguished (GEO accession number GSE11428).[39]

To gain an overview of the biological processes that oligomer 6 or 7 may modulate, gene ontology (GO) enrichment analysis was performed. Enrichment scores elicited by oligomer 6 or 7 for genes up- or down-regulated by at least 3-fold (P≤0.05) reveal they are distinct, confirming that genome-wide expression is differentially affected by treatment with either oligomer 6 or 7 in LNCaP-abl cells (FIG. 10B). The contrasting patterns in the gene expression and gene ontology enrichment profiles are consistent with oligomer 6 and 2 antagonizing the AR through different mechanisms of action.

Figure 15:
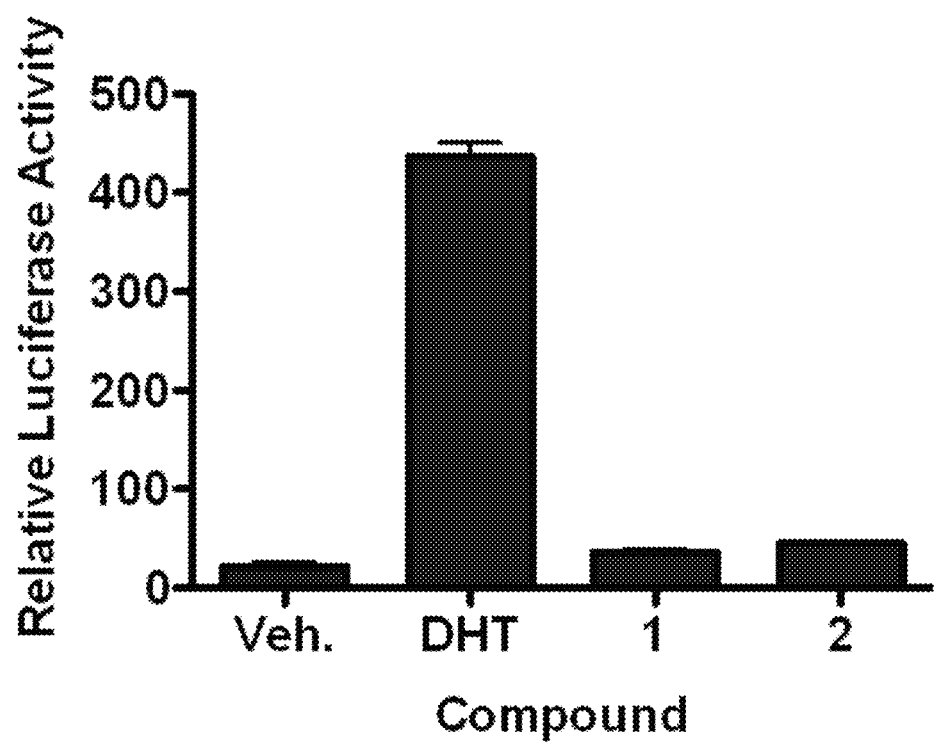

To address the issue of potency, oligomers 6 and 7 were examined for their ability to induce AR-mediated transcriptional activation. The inventors used a LNCaP cell line (androgen dependent) that stably expresses the AR-responsive luciferase reporter gene under the probasin promoter (the rat homologue of PSA).[40] These cells, termed LB1-luc, were treated with oligomers 6 or 7 to a final concentration of 100 nM or 1 µM for 24 h, and AR-mediated transcriptional activation was measured.22 Oligomers 6 and 7 fail to activate AR-mediated transcriptional activation at a concentration of 100 nM (FIG. 15, 1 is Oligomer 6 and 2 is Oligomer 7) but activate AR at 1 µM.22 These data, in combination with cell proliferation data (analyzed at 3 different concentrations in LNCaP-abl cells), reveal that oligomers 6 and 7 are acting in distinctly different manners and that functional variations are not attributable to testing at a concentration for which one compound is more active.

There are currently no curative treatment regimens available for castrate-resistant prostate cancer, creating an urgent need to identify new therapeutic agents that modulate AR activity through unique mechanisms of action. Furthermore, the development of AR modulators that possess distinct mechanisms of AR antagonism has the potential advantage of circumventing drug resistance in AR pharmacology. The ability to mitigate AR nuclear function, thus preventing binding interactions between DNA and co-activator proteins, may address unmet clinical needs for castrate-resistant prostate cancer.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for peptoid oligomers are approximate, and are provided for description.

It is also understood that the synthetic oligomers or compounds of the invention are capped with the appropriate X and Y groups. If not shown then it is understood that the end groups are appropriately H or $NH_2$.

All publications, including but not limited to patents and patent applications, cited in this specification are herein incorporated by reference as if each individual publication were specifically and individually indicated to be incorporated by reference herein as though fully set forth.

REFERENCES

1. Bhasin, S.; Cunningham, G. R.; Hayes, F. J.; Matsumoto, A. M.; Snyder, P. J.; Swerdloff, R. S.; Montori, V. M. *J. Clin. Endocrinol. Metab.* 2010, 95, 2536.
2. Heinlein, C. A.; Chang, C. Endo. Rev. 2004, 25, 276. (3) Jez, J. M.; Flynn, T. G.; Penning, T., M. *Biochem. Pharmacol.*1997, 54, 639.
3. Centenera, M. M.; Harris, J. M.; Tilley, W. D.; Butler, L. M. *Mol. Endocrinol.* 2008, 22, 2373.
4. Gioeli, D.; Ficarro, S. B.; Kwiek, J. J.; Aaronson, D.; Hancock, M.; Catling, A. D.; White, F. M.; Christian, R. E.; Settlage, R. E.; Shabanowitz, J.; Hunt, D. F.; Weber, M. J. *J. Biol. Chem.* 2002, 277,29304.
5. Shaffer, P. L.; Jivan, A.; Dollins, D. E.; Claessens, F.; Gewirth, D. T., *Proc. Natl. Acad. Sci. USA* 2004, 101, 4758.
6. Tannock, I. F.; de Wit, R.; Berry, W. R.; Horti, J.; Pluzanska, A.; Chi, K. N.; Oudard, S.; Theodore, C.; James, N. D.; Turesson, I.; Rosenthal, M. A.; Eisenberger, M. A., *N. Engl. J. Med.* 2004, 351, 1502.
7. McGinley, P. L.; Koh, J. T. *J. Am. Chem. Soc.* 2007, 129, 3822. Chen, C. D.; Welsbie, D. S.; Tran, C.; Baek, S. H.; Chen, R.; Vessella, R.; Rosenfeld, M. G.; Sawyers, C. L. *Nat. Med.* 2004, 10,33.
8. Culig, Z.; Hoffmann, J.; Erdel, M.; Eder, I. E.; Hobisch, A.; Hittmair, A.; Bartsch, G.; Utermann, G.; Schneider, M. R.; Parczyk, K.; Klocker, H. *Br. J. Cancer* 1999, 81, 242. (10b) Tran, C. et al. *Science* 2009, 324, 787.
9. Carlson, C. B. et al. (2007). Selective Tumor Cell Targeting Using Low-*Affinity*, Multivalent Interactions. *ACS Chem. Biol.* 2, 119-127.
10. Xu, X. et al. (2002). MHC/Peptide Tetramer-Based Studies Of T Cell Function. *J Immunol Methods.* 268, 21-28.
11. Puffer, E. B. et al. (2007). Activating B Cell Signaling With Defined Multivalent Ligands. *ACS Chem. Biol.* 2, 252-262.
12. Fowler, A. S. et al. (2009). Structure-Function Relationships In Peptoids: Recent Advances Toward Deciphering The Structural Requirements For Biological Function. *Org. Biomol. Chem.* 7, 1508-1524.
13. Reczec, J. et al. (2009). Multivalent Recognition of Peptides by Modular Self-Assembled Receptors. *JACS.* 131, 2408-2415.
14. Moller, W. et al. (2010). Structural Basis Of Multivalent Binding To Wheat Germ Agglutinin. *J. Am. Chem. Soc.* 132, 8704-8719.
15. Wang, Y. et al. (2005). Monodisperse Protein-Based Glycopolymers via a Combined Biosynthetic and Chemical Approach. *J. Am. Chem. Soc.* 127, 16392-16393.
16. Roitt, I. et al. (2001). Immunology. *Mosby.* 6, 72.
17. Tan, N. C. et al. (2008). High-Throughput Evaluation Of Relative Cell Permeability Between Peptoids And Peptides. *Bioorg. Med. Chem.* 16, 5853-5861.
18. Yu, P. et al. (2005). A High-Throughput Assay For Assessing The Cell Permeability Of Combinatorial Libraries. *Nat. Biotechnol.* 23, 746-751.
19. Zuckermann, R. et al. (1992). "Efficient Method for the Preparation of Peptides [Oligo(N-substituted glycines)] by Submonomer Solid-Phase Synthesis." *J. Am. Chem. Soc.* 114, 10646-10647.
20. Hjelmgaard, T. et al. (2009). Convenient Solution-Phase Synthesis And Conformational Studies Of Novel Linear and Cyclic α,β-Alternating Peptoids. *Organic Letters.* 11, 4100-4103.
21. Holub, J. M. et al. (2007). "Peptoids on Steroids: Precise Multivalent Estradiol-Peptidomimetic Oligomer s Generated via Azide-Alkyne [3+2] Cycloaddition Reactions." *QSAR Comb. Sci.* 26, 1175-1180.
22. Miller, S. M. et al. (1995). Comparison Of The Proteolytic Susceptibilities Of Homologous L-Amino Acid, D-Amino Acid, And N-Substituted Glycine Peptide And Peptoid Oligomers. *Drug Dev. Res.* 35, 20-32.
23. Lee, Y.; Sampson, N. S. *Curr. Opin. Struct. Biol.* 2006, 16, 544.
24. Childs-Disney, J. L.; Tsitovich, P. B.; Disney, M. D. *ChemBioChem* 2011, 12, 2143.
25. Yoo, B; Shin, S. B. Y.; Huang, M. L.; Kirshenbaum, K. *Chem.-Eur. J.* 2010, 16, 5528.
26. Kolb, H. C.; Finn, M. G.; Sharpless, K. B. *Angew. Chem., Int. Ed.* 2001, 40, 2004.
27. Lemus, A. E.; Enriquez, J.; Garcia, G. A.; Grillasca, I.; Perez-Palacios, G., *J. Steroid Biochem.* 1997, 60, 121.
28. Chang, H.-C.; Miyamoto, H.; Marwah, P.; Lardy, H.; Yeh, S.; Huang, K.-E.; Chang, C. *Proc. Natl. Acad. Sci. USA* 1999, 96, 11173.
29. Holub, J. M.; Garabedian, M. J.; Kirshenbaum, K. *QSAR & Comb. Sci.* 2007, 26, 1175.
30. Note that recombinant AR-LBD does not contain N/C terminal interactions that are present in full length AR or AR-LBD mutants. (a) He, B.; Minges, J. T.; Lee, L. W.; Wilson, E. M. *J. Biol. Chem.* 2002, 277, 10226. (b) Bohl, C. E.; Gao, W.; Miller, D. D.; Bell, C. E.; Dalton, J. T. *Proc. Natl. Acad. Sci. USA* 2005, 102, 6201.
31. Zhang, J.; Gao, N.; DeGraff, D. J.; Yu, X.; Sun, Q.; Case, T. C.; Kasper, S.; Matusik, R. J. *The Prostate* 2010, 70, 934.
32. Singh, P.; Hallur, G.; Anchoori, R. K.; Bakare, O.; Kageyama, Y.; Khan, S. R.; Isaacs, J. T. *The Prostate* 2008, 68, 1570.
33. David, A. G. *Biochem. Pharmacol.* 1999, 57, 727.
34. Androgen Receptor Localisation and Turnover in Human Prostate Epithelium Treated with the Antiandrogen, Casodex. *J. Mol. Endocrinol.* 24, 339-351.
35. Jones, J. O., An, W. F., and Diamond, M. I. (2009) ARInhibitors Identified by High-Throughput Microscopy Detection of Conformational Change and Subcellular Localization. *ACS Chem. Biol.* 4, 199-208.
36. Ozers, M. S., Marks, B. D., Gowda, K., Kupcho, K. R., Ervin, K. M., De Rosier, T., Qadir, N., Eliason, H. C., Riddle, S. M., and Shekhani, M. S. (2006) The Androgen Receptor T877A Mutant Recruits LxxLL and FxxLF Peptides Differently than Wild-Type Androgen Receptor in a Time-Resolved Fluorescence Resonance Energy Transfer Assay. *Biochemistry* 46, 683-695.
37. Osguthorpe, D. J., and Hagler, A. T. (2011) Mechanism of Androgen Receptor Antagonism by Bicalutamide in the Treatment of Prostate Cancer. *Biochemistry* 50, 4105-4113.
38. Nickols, N. G., and Dervan, P. B. (2007) Suppression of Androgen Receptor-Mediated Gene Expression by a Sequence-Specific DNA-Binding Polyamide. *Proc. Natl. Acad. Sci. U.S.A.* 104, 10418-10423.
39. Wang, Q., Li, W., Zhang, Y., Yuan, X., Xu, K., Yu, J., Chen, Z., Beroukhim, R., Wang, H., Lupien, M., Wu, T., Regan, M. M., Meyer, C. A., Carroll, J. S., Manrai, A. K., Janne, O. A., Balk, S. P., Mehra, R., Han, B., Chinnaiyan, A. M., Rubin, M. A., True, L., Fiorentino, M., Fiore, C., Loda, M., Kantoff, P. W., Liu, X. S., and Brown, M. (2009) Androgen Receptor Regulates a Distinct Transcription Program in Androgen-Independent Prostate Cancer. *Cell* 138, 245-256.
40. Zhang, J., Gao, N., DeGraff, D. J., Yu, X., Sun, Q., Case, T. C., Kasper, S., and Matusik, R. J. (2010) Characterization of Cis Elements of the Probasin Promoter Necessary for Prostate-Specific Gene Expression. *Prostate* 70, 934-951.
41. Barber, R. D., Harmer, D. W., Coleman, R. A., and Clark, B. J. (2005) GAPDH as a Housekeeping Gene: Analysis of GAPDH mRNA Expression in a Panel of 72 Human Tissues. *Physiol. Genomics* 21, 389-395.

What is claimed is:

1. An antagonist of an androgen receptor, wherein the antagonist is a synthetic oligomer according to formula Ia or Ib:

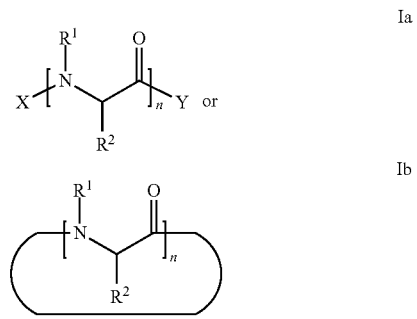

or a pharmaceutically acceptable salt thereof; and stereoisomers, isotopic variants and tautomers thereof;

wherein each $R^1$ is independently a substituted or unsubstituted alkyl, a substituted or unsubstituted alkenyl, a substituted or unsubstituted alkynyl, a substituted or unsubstituted cycloalkyl, a substituted or unsubstituted heterocycloalkyl, a substituted or unsubstituted aryl, or a substituted or unsubstituted heteroaryl; a substituted or unsubstituted cycloalkylalkyl, a substituted or unsubstituted heterocycloalkylalkyl, a substituted or unsubstituted aralkyl, or a substituted or unsubstituted heteroarylalkyl;

each $R^2$ is independently hydrogen, or a substituted or unsubstituted alkyl;

n is an integer between 2-45, when the synthetic oligomer is of formula Ia; and n is an integer between 4-45, when the synthetic oligomer is of formula Ib; and X is H, or a substituted or unsubstituted acyl; Y is $NH_2$, OH, an acylamino, or acyloxy;

provided that two monomers up to 40 monomers comprise an androgen receptor modulator moiety; wherein the monomers comprising an androgen receptor modulator moiety are according to formula II:

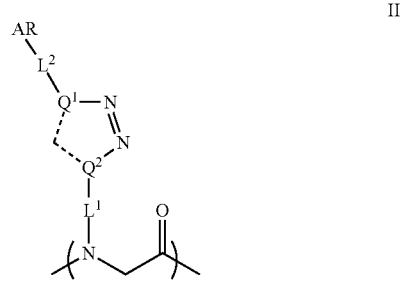

wherein $L^1$ is $-(CH_2)-_{m1}$ wherein the subscript m1 is an integer between 1-10;

$L^2$ is a single bond or $-(CH_2)-_{m2}$ wherein the subscript m2 is an integer between 1-10;

$Q^1$ is N, and $Q^2$ is C; or $Q^1$ is C, and $Q^2$ is N;

one of the dotted bonds is a single bond and the other is a double bond;

AR is

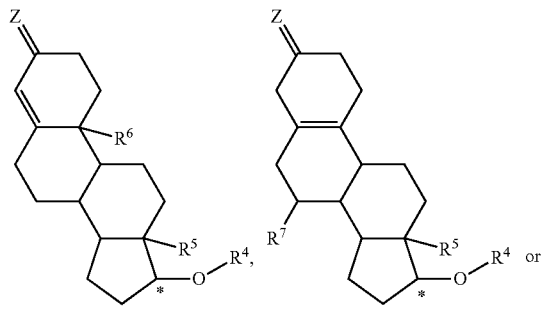

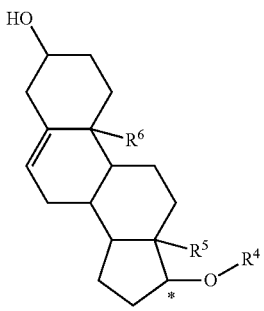

Z is O or N—O—$R^{3a}$; $R^{3a}$ is H or substituted or unsubstituted alkyl;

$R^4$ is H or acyl; $R^5$ is substituted or unsubstituted alkyl; each $R^6$ and $R^7$ is independently H or substituted or unsubstituted alkyl; and * denotes the attachment point; and provided that the oligomer is other than

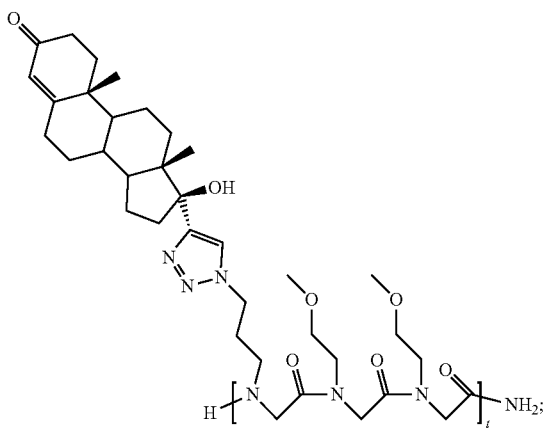

wherein t is 2 or 3.

2. The synthetic oligomer according to claim 1, wherein the synthetic oligomer comprises at least one triazolyl moiety wherein $Q^1$ is N, and $Q^2$ is C.

3. The synthetic oligomer according to claim 1, wherein the monomers comprising an androgen receptor modulator moiety are according to formula IIIa:

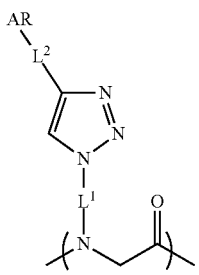

IIIa wherein $L^1$, $L^2$, and AR are as in claim 1.

4. The synthetic oligomer according to claim 1, wherein the monomers are according to formula IVa, IVb, IVc, Va, Vb, or Vc:

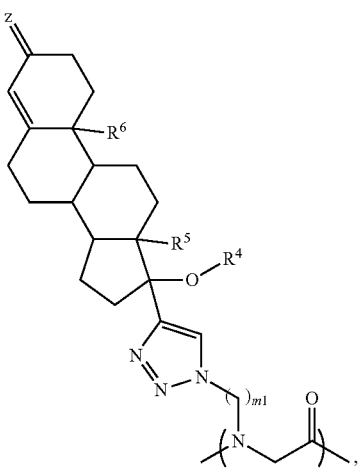

IVa

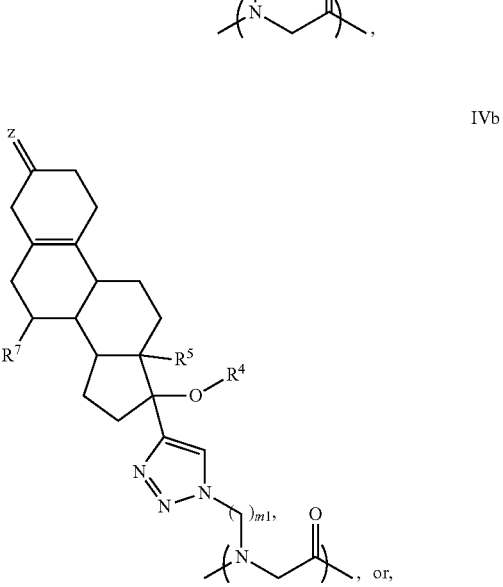

IVb

, or,

-continued

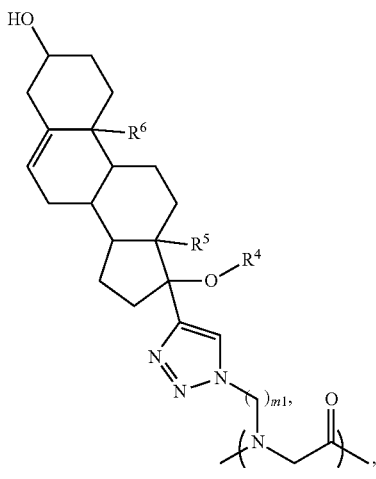

IVc

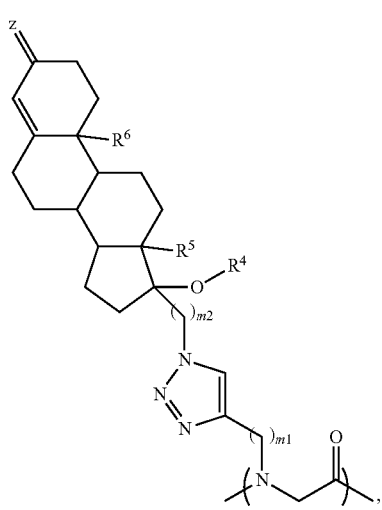

Va

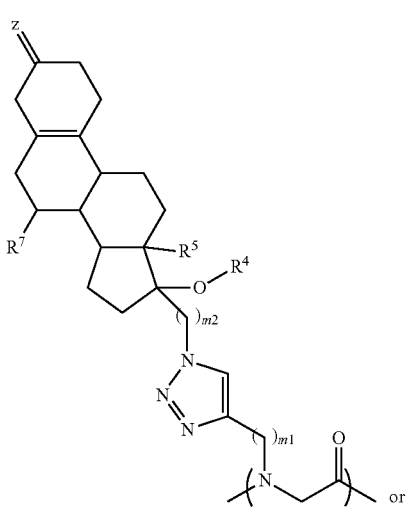

Vb

-continued

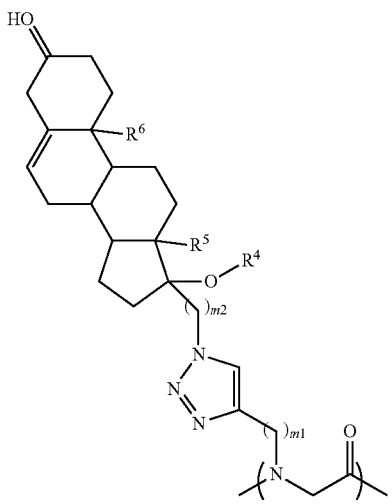

Vc or a pharmaceutically acceptable salt thereof; and stereoisomers, isotopic variants and tautomers thereof;
wherein Z is O or N—O—$R^{3a}$; $R^{3a}$ is H or substituted or unsubstituted alkyl; $R^4$ is H or acyl;
$R^5$ is substituted or unsubstituted alkyl; each $R^6$ and $R^7$ is independently H or substituted or unsubstituted alkyl; the subscript m1 is independently an integer between 1-10, and wherein the subscript m2 is an integer between 1-10.

5. The synthetic oligomer according to claim 1, wherein each $R^1$ is independently selected from unsubstituted alkyl, substituted alkyl, substituted or unsubstituted cycloalkylalkyl, substituted or unsubstituted aryl, substituted or unsubstituted aralkyl, and substituted or unsubstituted heteroarylalkyl.

6. The synthetic oligomer according to claim 5, comprising $R^1$ selected from aminoalkyl, guanidinoalkyl ($H_2N$—C(=NH)—NH-alkyl), N-containing heteroarylalkyl and substituted or unsubstituted diarylalkyl.

7. The synthetic oligomer according to claim 1, wherein X, when present, is H; and Y, when present, is $NH_2$.

8. The synthetic oligomer according to claim 1, wherein the oligomer is according to formula XI:

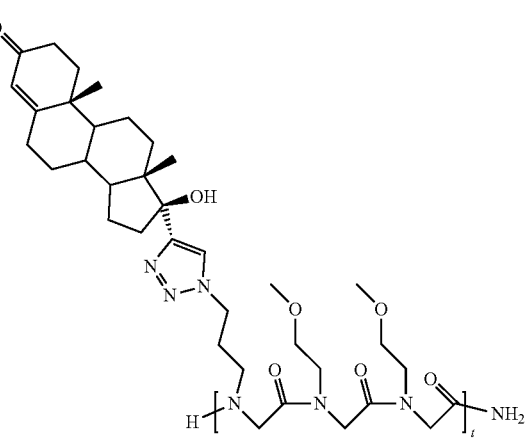

XI or a pharmaceutically acceptable salt thereof; and stereoisomers, isotopic variants and tautomers thereof;
and wherein the subscript t is 6.

9. The synthetic oligomer according to claim 1, wherein the oligomer is according to formula XII:

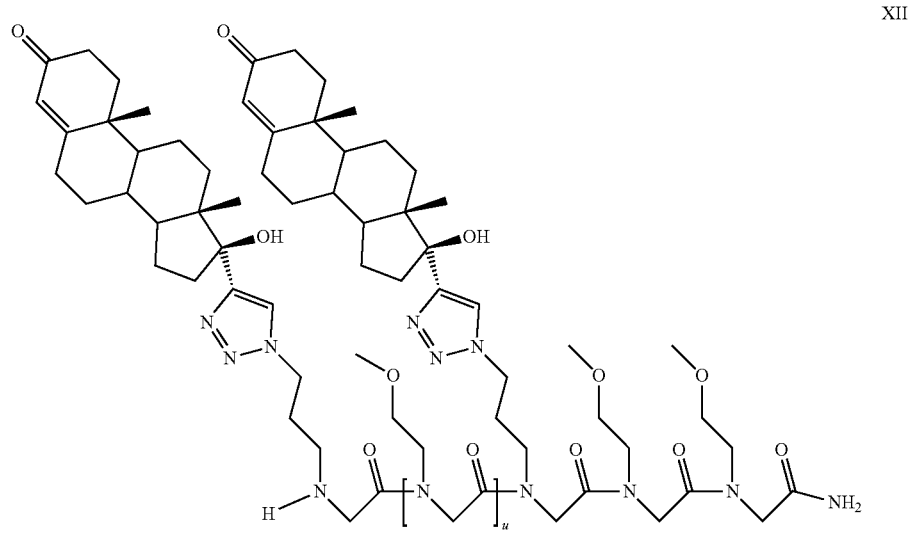

or a pharmaceutically acceptable salt thereof; and stereoisomers, isotopic variants and tautomers thereof;

and wherein the subscript u is 5 or 8.

10. The synthetic oligomer according to claim 1, wherein the oligomer is according to formula XIII:

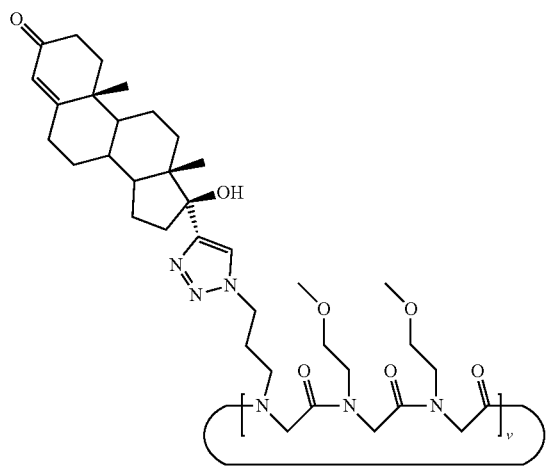

or a pharmaceutically acceptable salt thereof; and stereoisomers, isotopic variants and tautomers thereof;

and wherein the subscript v is 2, 3, 4, 5, or 6.

11. The synthetic oligomer according to claim 1, wherein the synthetic oligomer comprises at least one triazolyl moiety wherein $Q^1$ is C, and $Q^2$ is N.

12. The synthetic oligomer according to claim 6, wherein the monomers comprising an androgen receptor modulator moiety are according to formula IIIb:

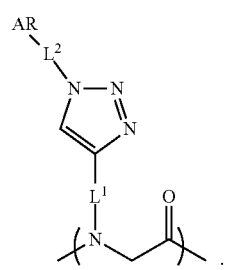

wherein $L^1$, $L^2$ and AR are as in claim 6.

13. A pharmaceutical composition comprising a pharmaceutically acceptable carrier and a pharmaceutically effective amount of synthetic oligomer according to claim 1.

14. A method for inhibiting androgen receptor activity in a human cancer cell in which said receptor is present, wherein said method comprises contacting the cell with an effective amount of an oligomer according to claim 1.

15. The method according to claim 14, wherein said method comprises contacting the cell with an effective amount of an oligomer according to formula Ia or Ib; or a pharmaceutically acceptable salt thereof; and stereoisomers, isotopic variants and tautomers thereof.

16. An antagonist of an androgen receptor, wherein the antagonist is a synthetic oligomer according to formula VII:

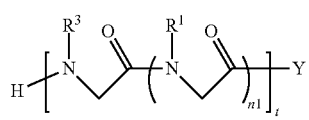

wherein each $R^1$ is independently a substituted or unsubstituted alkyl, a substituted or unsubstituted alkenyl, a substituted or unsubstituted alkynyl, a substituted or unsubstituted cycloalkyl, a substituted or unsubstituted heterocycloalkyl, a substituted or unsubstituted aryl, or a substituted or unsubstituted heteroaryl; a substituted or unsubstituted cycloalkylalkyl, a substituted or unsubstituted heterocycloalkylalkyl, a substituted or unsubstituted aralkyl, or a substituted or unsubstituted heteroarylalkl;

X is H, or a substituted or unsubstituted acyl; Y is $NH_2$, OH, an acylamino, or acyloxy;

the subscript t is an integer between 1 to 15; the subscript n1 is an integer between 1-10; each $R^3$ is

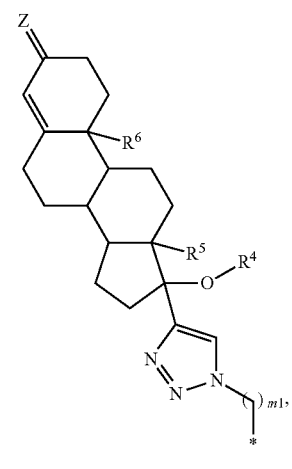

IVa′

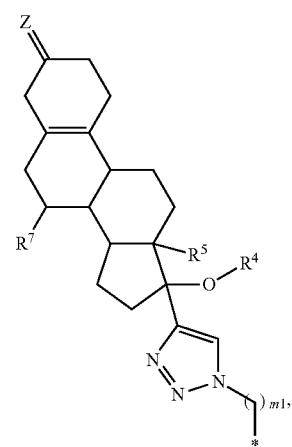

IVb′

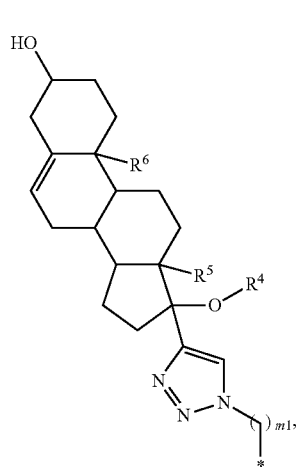

IVc′

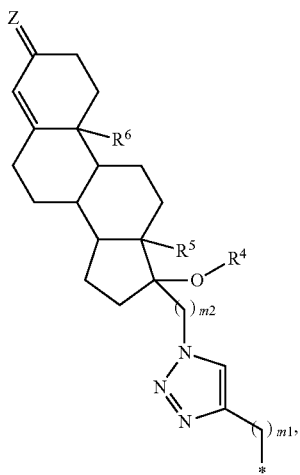

Va′

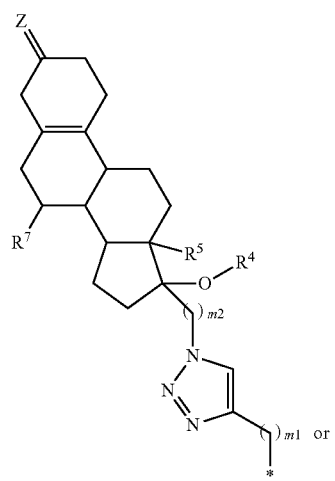

Vb′

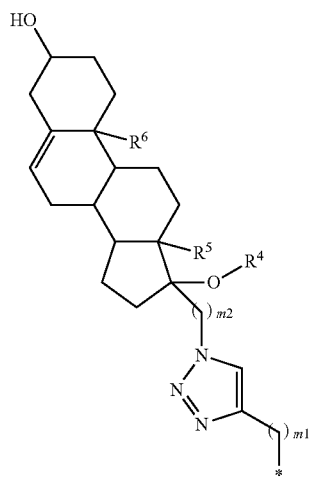

Vc′ wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10 and * denotes the attachment point;

or a pharmaceutically acceptable salt thereof; and stereoisomers, isotopic variants and tautomers thereof.

17. An antagonist of an androgen receipt, wherein the antagonist is a synthetic oligomer according to formula VIII:

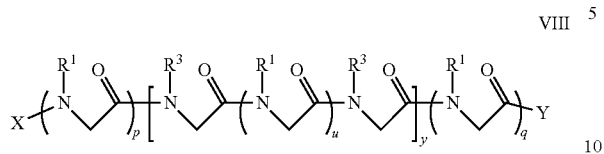

wherein
each $R^1$ is independently a substituted or unsubstituted alkyl, a substituted or unsubstituted alkenyl, a substituted or unsubstituted alkynyl, a substituted or unsubstituted cycloalkyl, a substituted or unsubstituted heterocycloalkyl, a substituted or unsubstituted aryl, or a substituted or unsubstituted heteroaryl; a substituted or unsubstituted cycloalkylalkyl, a substituted or unsubstituted heterocycloalkylalkyl, a substituted or unsubstituted aralkyl, or a substituted or unsubstituted heteroarylalkyl;
X is H, or a substituted or unsubstituted acyl; Y is $NH_2$, OH, an acylamino, or acyloxy;
the subscript u is an integer between 0 to 15; each of the subscripts p, q, and y is an integer between 1-10; each $R^3$ is

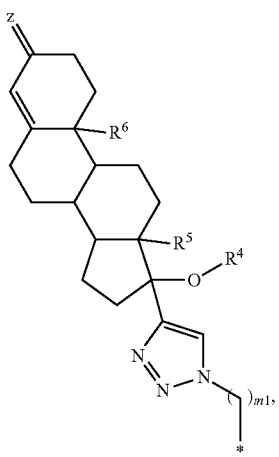

IVa′

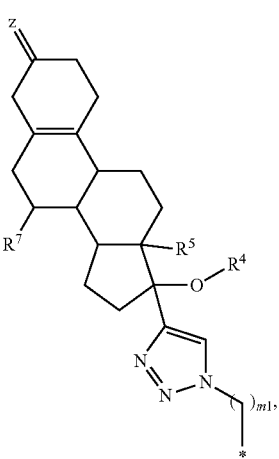

IVb′

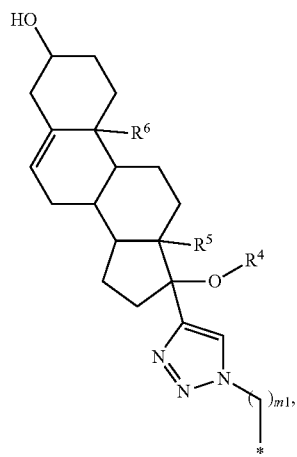

IVc′

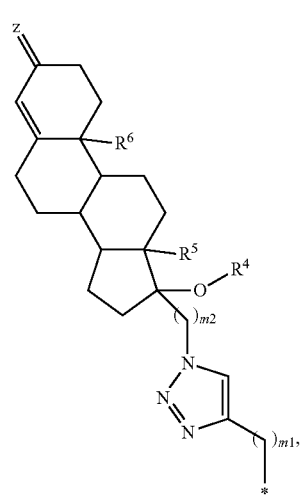

Va′

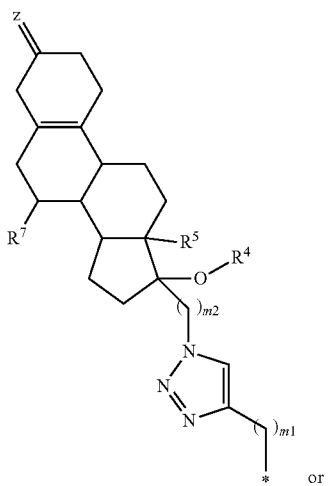

Vb′ or

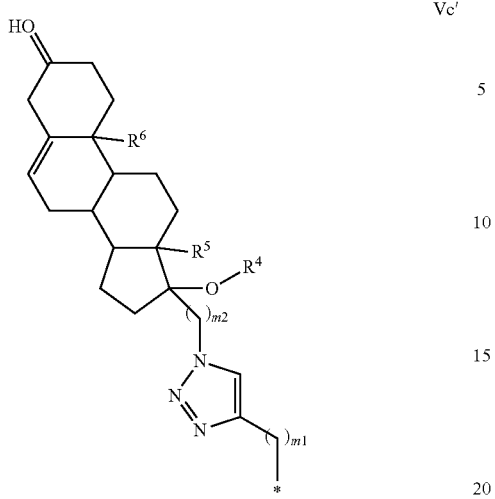

Vc' wherein Z is O or N—O—R$^{3a}$; R$^{3a}$ is H or substituted or unsubstituted alkyl; R$^4$ is H or acyl; R$^5$ is substituted or unsubstituted alkyl; each R$^6$ and R$^7$ is independently H or substituted or unsubstituted alkyl; and the subscript m1 is an integer between 1-10; and the subscript m2 is an integer between 0-10 and * denotes the attachment point;

or a pharmaceutically acceptable salt thereof; and stereoisomers, isotopic variants and tautomers thereof.

18. An antagonist of an androgen receptor, wherein the antagonist is a synthetic oligomer according to formula IX:

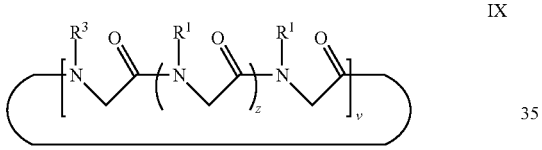

IX wherein
each R$^1$ is independently a substituted or unsubstituted alkyl, a substituted or unsubstituted alkenyl, a substituted or unsubstituted alkynyl, a substituted or unsubstituted cycloalkyl, a substituted or unsubstituted heterocycloalkyl, a substituted or unsubstituted aryl, or a substituted or unsubstituted heteroaryl; a substituted or unsubstituted cycloalkylalkyl, a substituted or unsubstituted heterocycloalkylalkyl, a substituted or unsubstituted aralkyl, or a substituted or unsubstituted heteroarylalkyl;
the subscript v is an integer between 1 to 15; the subscript z is an integer between 1-10; each R$^3$ is

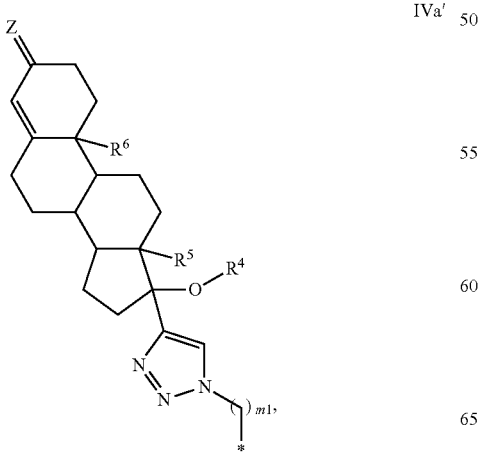

IVa'

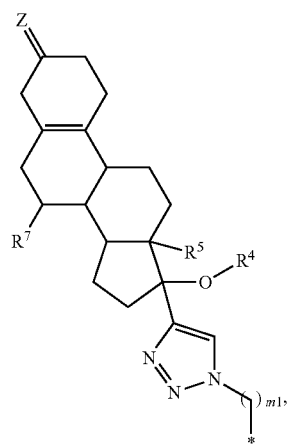

IVb'

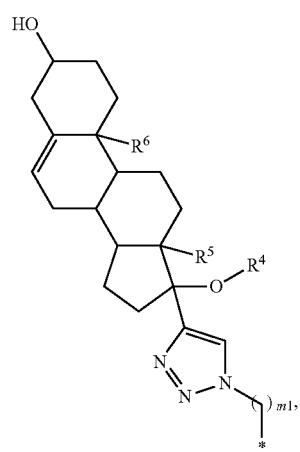

IVc'

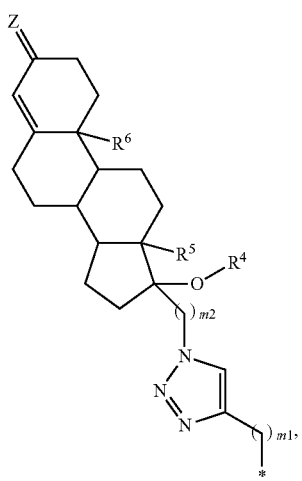

Va'

85
-continued

Vb'

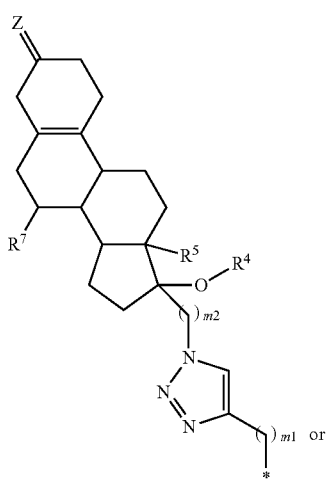

Vc'

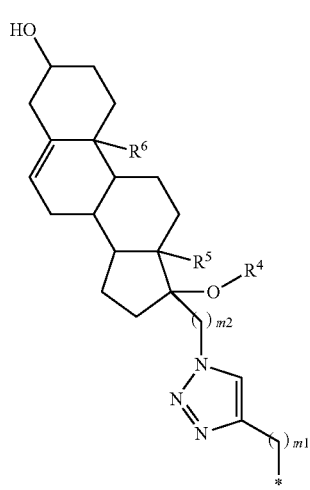

wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10; and * denotes the attachment point;
or a pharmaceutically acceptable salt thereof; and stereoisomers, isotopic variants and tautomers thereof.

19. An antagonist of an androgen receptor, wherein the antagonist is a synthetic oligomer according to formula X:

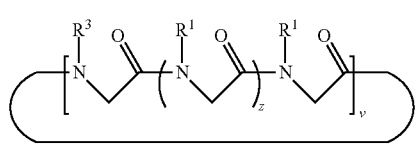

X

86 wherein $R^3$ is

IVa'

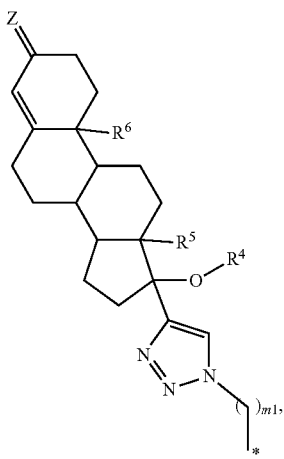

IVb'

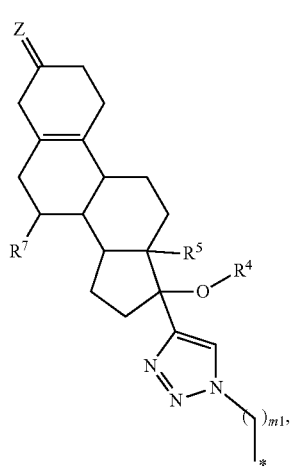

IVc'

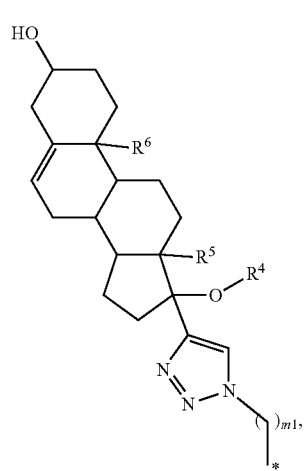

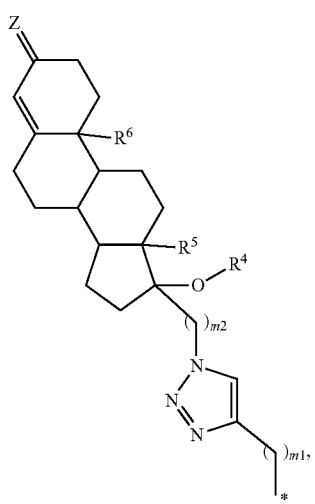

Va'

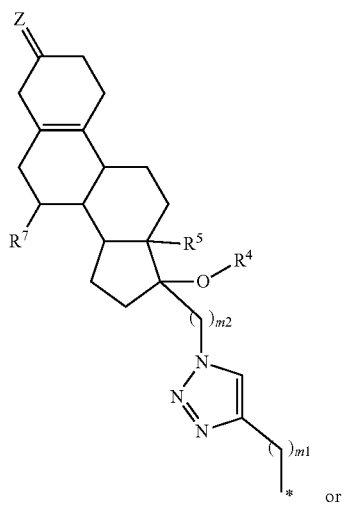

Vb'

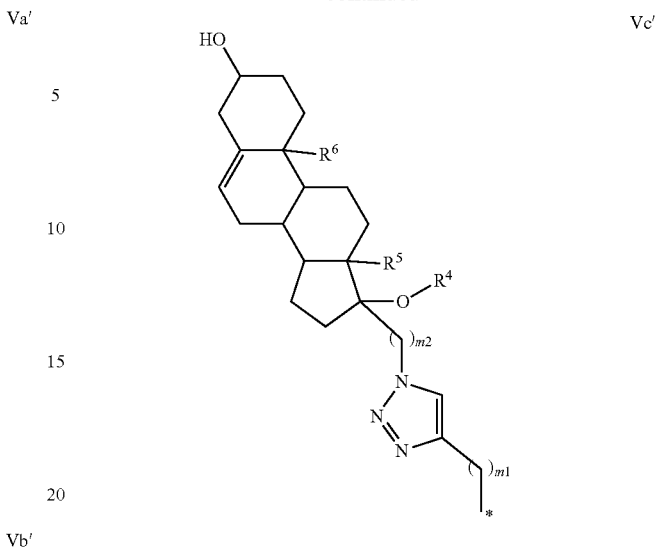

Vc' wherein Z is O or N—O—$R^{3a}$; $R^{3a}$ is H or substituted or unsubstituted alkyl; $R^4$ is H or acyl; $R^5$ is substituted or unsubstituted alkyl; each $R^6$ and $R^7$ is independently H or substituted or unsubstituted alkyl; and the subscript m1 is an integer between 1-10; and the subscript m2 is an integer between 0-10; and * denotes the attachment point;

each $R^1$ is independently unsubstituted alkyl, substituted alkyl, cycloalkylalkyl, or N-containing heteroarylalkyl; the subscript v is an integer between 2 to 15; and the subscript z is an integer between 1-10;

or a pharmaceutically acceptable salt thereof; and stereoisomers, isotopic variants and tautomers thereof.

20. The synthetic oligomer according to claim 19, comprising $R^1$ selected from aminoalkyl and guanidinoalkyl ($H_2N$—C(=NH)—NH-alkyl).

* * * * *